United States Patent
Wang et al.

(10) Patent No.: US 12,419,873 B2
(45) Date of Patent: Sep. 23, 2025

(54) USE OF JAK INHIBITORS IN PREPARATION OF DRUGS FOR TREATING JAK KINASE-RELATED DISEASES

(71) Applicant: ZHUHAI UNITED LABORATORIES CO., LTD., Guangdong (CN)

(72) Inventors: Shuai Wang, Guangdong (CN); Degang Wang, Guangdong (CN); Shouting Wu, Guangdong (CN); Tingting Yu, Guangdong (CN); Miao Fang, Guangdong (CN); Liwei Mu, Guangdong (CN); Liang Fang, Guangdong (CN)

(73) Assignee: ZHUHAI UNITED LABORATORIES CO., LTD., Guangdong (CN)

( * ) Notice: Subject to any disclaimer, the term of this patent is extended or adjusted under 35 U.S.C. 154(b) by 614 days.

(21) Appl. No.: 17/760,233

(22) PCT Filed: Feb. 13, 2020

(86) PCT No.: PCT/CN2020/075024
§ 371 (c)(1),
(2) Date: Aug. 5, 2022

(87) PCT Pub. No.: WO2021/159372
PCT Pub. Date: Aug. 19, 2021

(65) Prior Publication Data
US 2023/0113620 A1 Apr. 13, 2023

(51) Int. Cl.
*A61K 31/437* (2006.01)
*A61K 31/438* (2006.01)
(Continued)

(52) U.S. Cl.
CPC .......... *A61K 31/437* (2013.01); *A61K 31/438* (2013.01); *A61P 1/04* (2018.01); *A61P 17/00* (2018.01); *A61P 29/00* (2018.01)

(58) Field of Classification Search
CPC ....... A61K 31/437; A61K 31/438; A61P 1/04; A61P 17/00; A61P 29/00; A61P 19/02;
(Continued)

(56) References Cited

U.S. PATENT DOCUMENTS 11,919,896 B2 * 3/2024 Mao ...................... C07D 471/04
2009/0220688 A1 9/2009 Morton

FOREIGN PATENT DOCUMENTS

| CN | 104262337 A | 1/2015 |
| CN | 107759587 A | 3/2018 |

(Continued)

OTHER PUBLICATIONS

International Search Report for Corresponding International Application No. PCT/CN2020/075024 dated Nov. 19, 2020 with English Translation (6 Pages).

*Primary Examiner* — Taylor V Oh
(74) *Attorney, Agent, or Firm* — LUCAS & MERCANTI, LLP

(57) ABSTRACT

Disclosed is the use of a JAK inhibitor [1,2,4]-triazolo-[1,5-a]0pyridine compound in the preparation of drugs for treating autoimmune, inflammatory or allergic diseases, or diseases such as transplant rejection. The JAK inhibitor [1,2,4]-triazolo-[1,5-a]-pyridine compound comprises a compound as shown in formula (I), an isomer thereof or a pharmaceutically acceptable salt thereof. The JAK inhibitor has a good efficacy in animal model tests of diseases such as autoimmune, inflammatory or allergic diseases.

16 Claims, 5 Drawing Sheets

(51) Int. Cl.
*A61P 1/04* (2006.01)
*A61P 17/00* (2006.01)
*A61P 29/00* (2006.01)

(58) Field of Classification Search
CPC  A61P 37/06; A61P 37/08; A61P 17/06; A61P 37/00; C07D 471/04
USPC .................................................. 514/210.16
See application file for complete search history.

(56) References Cited

FOREIGN PATENT DOCUMENTS

| | | |
|---|---|---|
| CN | 108341814 A | 7/2018 |
| WO | 2020038457 A1 | 2/2020 |

\* cited by examiner

USE OF JAK INHIBITORS IN PREPARATION OF DRUGS FOR TREATING JAK KINASE-RELATED DISEASES

CROSS-REFERENCE TO RELATED APPLICATION

This application is a 371 of PCT/CN2020/075024, filed Feb. 13, 2020.

TECHNICAL FIELD

The present invention relates to the pharmaceutical field, and, in particular to an application of [1,2,4] triazolo [1,5-α] pyridine compounds in the preparation of drugs for the treatment of JAK kinase related autoimmune, inflammatory, allergic diseases, or graft-versus-host diseases etc.

BACKGROUND ART

JAK belongs to a tyrosine kinase family involved in inflammation, autoimmune diseases, proliferative diseases, transplantation rejection (or graft-versus-host disease), diseases involving impaired cartilage turnover, congenital cartilage malformations and/or diseases related to excess IL6 secretion. Studies have confirmed that inhibition of JAK signaling pathway is considered to regulate multiple signaling pathways related to inflammation, autoimmune diseases, proliferative diseases, transplantation rejection, diseases involving cartilage turnover damage, congenital cartilage malformation and/or diseases related to excess IL6 secretion. The invention also provides a method for producing the compounds, a pharmaceutical composition containing the compounds, and a method for preventing and/or treating inflammation, autoimmune diseases, proliferative diseases, transplant rejection, diseases involving impaired cartilage regeneration, congenital cartilage malformations, and/or diseases related to excess IL6 secretion by administering the compounds of the present application.

Janus kinase (JAK) is a cytoplasmic tyrosine kinase that transduces cytokine signals from membrane receptors to STAT transcription factors. The prior art has described four JAK family members: JAK1, JAK2, JAK3 and TYK2. When cytokines bind to their receptors, JAK family members are autophosphorylated and/or transphosphorylated with each other, then STATs phosphorylated, and then migrate into the nucleus to regulate transcription. JAK-STAT intracellular signal transduction is applicable to interferon, most of interleukins, and a variety of cytokines and endocrine factors, such as EPO, TPO, GH, OSM, LIF, CNTF, GM-CSF and PRL (vainchenker W. et al. (2008)).

The combination study of genetic models and small molecule JAK inhibitors has revealed the therapeutic potential of several JAKs. JAK3 is identified as an immunosuppressive target by mouse and human genetics (O'Shea J. et al. (2004)). JAK inhibitors have been successfully used in clinical development, initially for organ transplantation rejection, but later for other immunoinflammatory indications as well, such as inflammatory bowel disease (IBD), allergic dermatitis (AD), rheumatoid arthritis (RA), psoriasis and Crohn's disease (http://clinicaltrials.gov/). TYK2 is a potential target of immune inflammatory diseases, which has been confirmed by human genetics and mouse knockout studies (levy D. and Loomis C. (2007)). JAK1 is a new target in the field of immune inflammatory diseases, it can be heterodimerized with other JAKs to transduce cytokine driven pro-inflammatory signal transduction. Therefore, inhibition of JAK1 and/or other JAKs is expected to have therapeutic benefits for a range of inflammatory disorders and other diseases driven by JAK mediated signal transduction.

Inflammatory bowel disease is an idiopathic intestinal inflammatory disease involving ileum, rectum and colon. Clinical manifestations include diarrhea, abdominal pain, and even bloody stool. Inflammatory bowel diseases include ulcerative colitis and Crohn's disease. Ulcerative colitis is a continuous inflammation of colonic mucosa and submucosa, and it usually affect the rectum firstly, then gradually spreads to the whole colon. Crohn's disease can affect the whole digestive tract, which is a discontinuous full-thickness inflammation. The most frequently involved parts are the terminal ileum, colon and perianal.

An allergic dermatitis is a skin disease caused by allergens. It mainly refers to skin diseases such as redness, itching, wind mass, peeling, etc., caused by human exposure to certain allergens. Specific allergens include contact allergens, inhalation allergens, ingestion allergens and injection allergens. Each type of allergen can cause corresponding allergic reaction, mainly manifested as a variety of dermatitis, eczema, urticaria and so on.

Psoriasis, commonly known as psoriasis, is a chronic inflammatory skin disease, which has a great impact on the physical health and mental status of patients. The clinical manifestations mainly include erythema and scaly, which can occur all over the body, but generally mainly on the scalp and limbs.

Systemic lupus erythematosus (SLE) is an autoimmune disease with unknown etiology, which is characterized by the damage of different target organs caused by a variety of autoantibodies. Due to the tissue damage caused by a large number of pathogenic autoantibodies and immune complexes in the body, clinical manifestations of various system and organ damage can occur, such as skin, joints, serosa, heart, kidney, central nervous system, blood system, etc.

Graft versus host disease (GVHD) is caused by a series of "cytokine storms" stimulated by T lymphocytes in allogeneic donor grafts after transplantation, which greatly enhance their immune response to recipient antigens.

US2009220688 discloses Filgotinib, which is a drug developed by Galapagos company and currently in phase III clinical use for the treatment of rheumatoid arthritis.

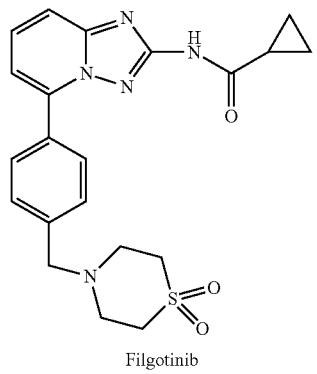 [SMILES: O=C(Nc1nc2cccc(-c3ccc(CN4CCS(=O)(=O)CC4)cc3)n2n1)C1CC1]

Filgotinib

On this basis, it is necessary to develop new JAK inhibitors [1,2,4] triazolo [1,5-a]pyridine compounds and their applications in the preparation of drugs for inflammatory bowel disease, allergic dermatitis, psoriasis, systemic lupus erythematosus or graft-versus-host disease.

SUMMARY

In view of the above technical status, the present invention provides an application of JAK inhibitors [1,2,4]triazolo[1,5-a] pyridine compounds as shown in formula (I), their isomers or their pharmaceutically acceptable salts in the preparation of drugs for the treatment of JAK kinase related diseases:

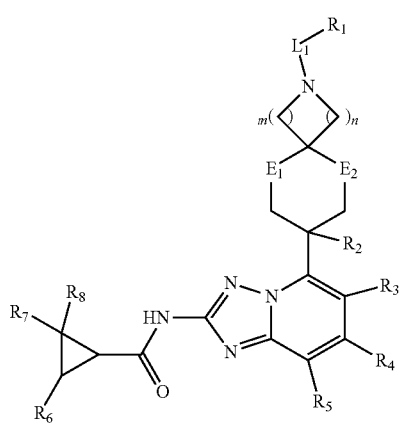

wherein,
$E_1$ and $E_2$ are independently selected from single bond, —$CH_2$— or —$(CH_2)_2$—, respectively;
$L_1$ is selected from single bond, —$(CH_2)_g$—, —C(=O)— or —C(=O)—$(CH_2)_h$—;
m is 1 or 2;
n is 1 or 2;
g is 1, 2 or 3;
h is 1, 2 or 3;
$R_1$ is selected from H, CN, $C_{1-6}$ alkyl or 3- to 6-membered cycloalkyl, wherein the $C_{1-6}$ alkyl and 3- to 6-membered cycloalkyl are optionally substituted by 1, 2 or 3 $R_a$;
$R_2$ is selected from H, F, Cl, Br, I or $C_{1-3}$ alkyl, wherein the $C_{1-3}$ alkyl is optionally substituted by 1, 2 or 3 $R_b$;
$R_3$, $R_4$ and $R_5$ are independently selected from H, F, Cl, Br, I or $C_{1-3}$ alkyl, respectively, wherein the $C_{1-3}$ alkyl is optionally substituted by 1, 2 or 3 Re;
$R_6$, $R_7$ and $R_8$ are independently selected from H, F, Cl, Br, I or $C_{1-3}$ alkyl, respectively, wherein the $C_{1-3}$ alkyl is optionally substituted by 1, 2 or 3 $R_d$;
Each $R_a$ is independently selected from H, F, Cl, Br, I, CN or $C_{1-3}$ alkyl, respectively, wherein the $C_{1-3}$ alkyl is optionally substituted by 1, 2 or 3 R;
Each $R_b$ is independently selected from F, Cl, Br or I, respectively;
Each $R_c$ is independently selected from F, Cl, Br or I, respectively;
Each $R_d$ is independently selected from F, Cl, Br or I, respectively; and
Each R is independently selected from F, Cl, Br or I, respectively.

In the present invention, as one of embodiments, the present invention provides the application of JAK inhibitors [1,2,4]triazolo[1,5-a]pyridine compounds, their isomers or pharmaceutically acceptable salts in the preparation of drugs for the treatment of autoimmune diseases, inflammatory diseases, allergic diseases, or graft-versus-host diseases.

In the present invention, as one of the embodiments, the autoimmune diseases include systemic lupus erythematosus, psoriasis, psoriatic arthritis or lupus nephritis.

In the present invention, as one of the embodiments, the inflammatory diseases include inflammatory bowel disease, ankylosing spondylitis or primary cholangitis, etc.

In the present invention, as one of the embodiments, the allergic diseases include allergic dermatitis, contact dermatitis, allergic purpura or bronchial asthma, etc.

In the present invention, as one of the embodiments, the graft-versus-host disease includes but not limited to anti acute rejection, anti chronic rejection or inducing immune tolerance, etc.

In the present invention, as one of the embodiments, the invention provides an application of JAK inhibitor [1,2,4]triazolo[1,5-a]pyridine compound, its isomer or pharmaceutically acceptable salt in the preparation of drugs for the treatment of inflammatory bowel disease.

In the present invention, as one of the embodiments, the treatment of inflammatory bowel disease includes but not limited to inhibiting colon shortening.

In the present invention, as one of the embodiments, the invention provides an application of JAK inhibitor [1,2,4]triazolo[1,5-a]pyridine compound, its isomer or pharmaceutically acceptable salt in the preparation of drugs for the treatment of allergic dermatitis.

In the present invention, as one of the embodiments, the invention provides an application of JAK inhibitor [1,2,4]triazolo[1,5-a]pyridine compound, its isomer or pharmaceutically acceptable salt in the preparation of drugs for the treatment of psoriasis.

In the present invention, as one of the embodiments, the invention provides an application of JAK inhibitor [1,2,4]triazolo[1,5-a]pyridine compound, its isomer or pharmaceutically acceptable salt in the preparation of drugs for the treatment of systemic lupus erythematosus.

In the present invention, as one of the embodiments, the invention provides an application of JAK inhibitors [1,2,4]triazolo[1,5-a]pyridine compounds, their isomers or pharmaceutically acceptable salts in the preparation of drugs for the treatment of graft-versus-host disease.

As one of the embodiments, the graft-versus-host diseases include but not limited to anti acute rejection, anti chronic rejection or induction of immune tolerance.

As one of the embodiments, the invention is used to prepare drugs for treating inflammatory bowel disease, allergic dermatitis, psoriasis, systemic lupus erythematosus or graft-versus-host disease, such as the JAK inhibitors [1,2,4]triazolo[1,5-a]pyridine compounds of formula (I), their isomers or pharmaceutically acceptable salts thereof.

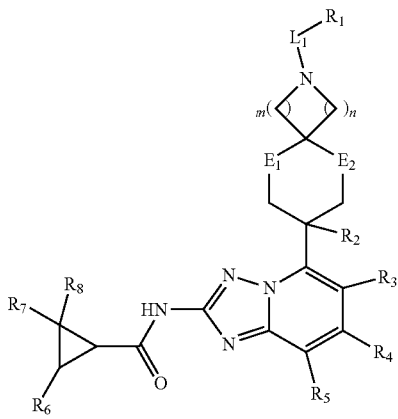

(I)

$E_1$ and $E_2$ are independently selected from single bond, —$CH_2$— or —$(CH_2)_2$—, respectively;
$L_1$ is selected from single bond, —$(CH_2)_g$—, -c(=O)— or -c(=O)—$(CH_2)_h$—;
m is 1 or 2;
n is 1 or 2;
g is 1, 2 or 3;
h is 1, 2 or 3;
$R_1$ is selected from H, CN, $C_{1-6}$ alkyl or 3- to 6-membered cycloalkyl, wherein the $C_{1-6}$ alkyl and 3- to 6-membered cycloalkyl are optionally substituted by 1, 2 or 3 $R_a$;
$R_2$ is selected from H, F, Cl, Br, I or $C_{1-3}$ alkyl, wherein the $C_{1-3}$ alkyl is optionally substituted by 1, 2 or 3 $R_b$;
$R_3$, $R_4$ and $R_5$ are independently selected from H, F, Cl, Br, I or $C_{1-3}$ alkyl, respectively, wherein the $C_{1-3}$ alkyl is optionally substituted by 1, 2 or 3 Re;
$R_6$, $R_7$ and $R_8$ are independently selected from H, F, Cl, Br, I or $C_{1-3}$ alkyl, respectively, wherein the $C_{1-3}$ alkyl is optionally substituted by 1, 2 or 3 $R_d$;
Each $R_a$ is independently selected from H, F, Cl, Br, I, CN or $C_{1-3}$ alkyl, respectively, wherein the $C_{1-3}$ alkyl is optionally substituted by 1, 2 or 3 R;
Each $R_b$ is independently selected from F, Cl, Br or I, respectively;
Each $R_c$ is independently selected from F, Cl, Br or I, respectively;
Each $R_d$ is independently selected from F, Cl, Br or I, respectively; and
Each R is independently selected from F, Cl, Br or I, respectively.

In the present invention, as one of the embodiments, each $R_a$ is independently selected from H, F, Cl, Br, I or CN, respectively, and other variables are defined in the invention.

In the present invention, as one of the embodiments, the $R_1$ is selected from H, CN, $C_{1-3}$ alkyl or 3- to 5-membered cycloalkyl, wherein the $C_{1-3}$ alkyl and 3- to 5-membered cycloalkyl are optionally replaced by 1, 2 or 3 $R_a$, and other variables are defined in the invention.

In the present invention, as one of the embodiments, the $R_1$ is selected from H, CN, $CH_3$,

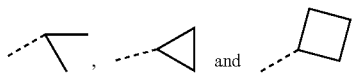

wherein the $CH_3$,

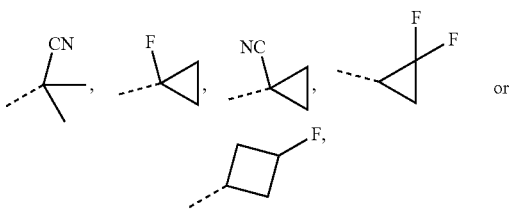

are optionally replaced by 1, 2 or 3 $R_a$, and other variables are defined in the invention.

In the present invention, as one of the embodiments, the $R_1$ is selected from H, CN, $CF_3$, $CHF_2$,

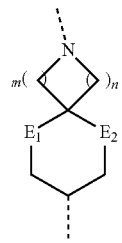

and other variables are defined in the invention.

In the present invention, as one of the embodiments, the $R_2$ is selected from H, F, $C_1$, Br or I, and other variables are defined in the invention.

In the present invention, as one of the embodiments, $R_3$, $R_4$ and $R_5$ are independently selected from H, F, Cl, Br or I, respectively, and other variables are defined in the invention.

In the present invention, as one of the embodiments, $R_6$, $R_7$ and $R_8$ are independently selected from H, F, Cl, Br or I, respectively, and other variables are defined in the invention.

In the present invention, as one of the embodiments, $L_1$ is selected from single bond, —$CH_2$—, —$(CH_2)_2$—, —C(=O)—, or —C(=O)—$(CH_2)$—, and other variables are defined in the invention.

In the present invention, as one of the embodiments, the structural unit

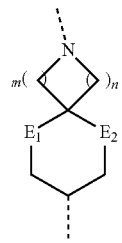

is selected from

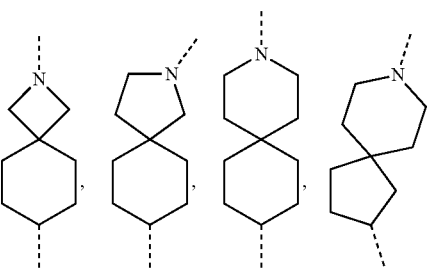

-continued
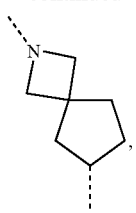
and other variables are defined in the invention.
In the present invention, as one of the embodiments, the structural unit
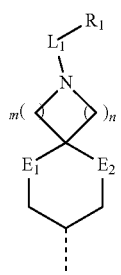
is selected from
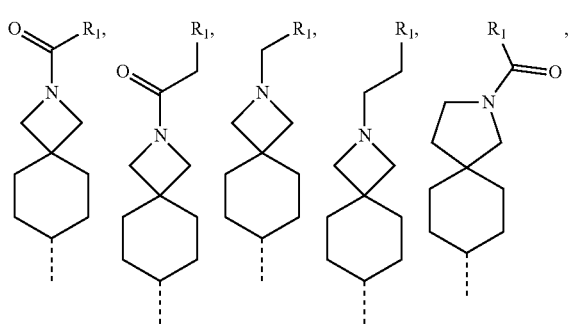
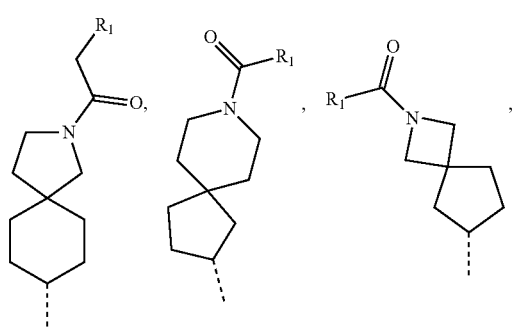
-continued
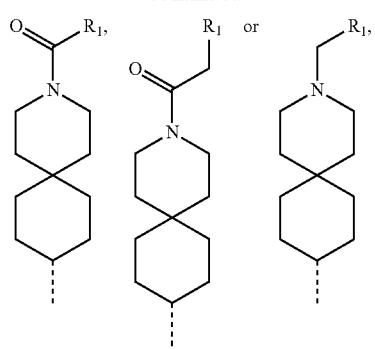
or and other variables are defined in the invention.
In the present invention, as one of the embodiments, the structural unit
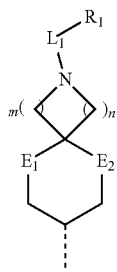
is selected from
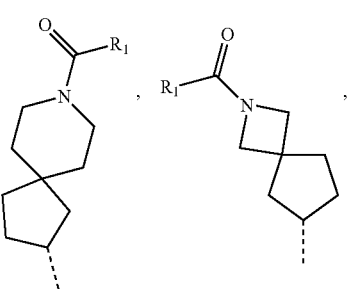

-continued
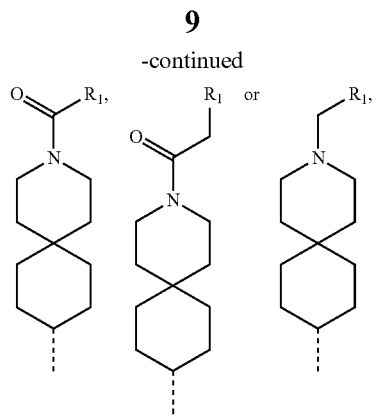
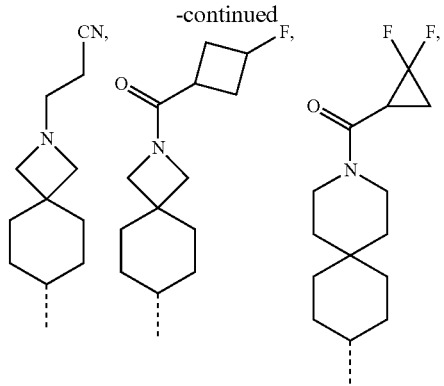
and other variables are defined in the invention.
In the present invention, as one of the embodiments, the structural unit
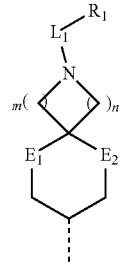
is selected from
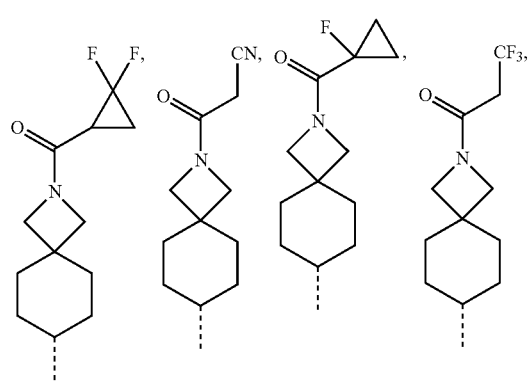
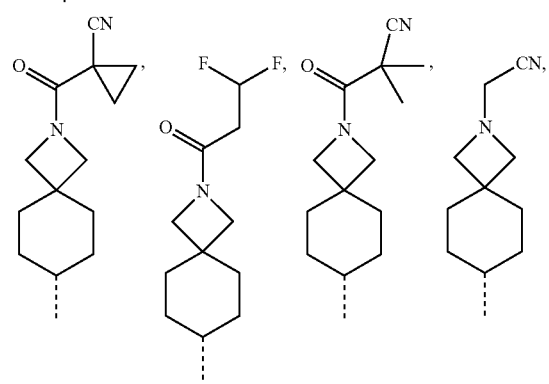
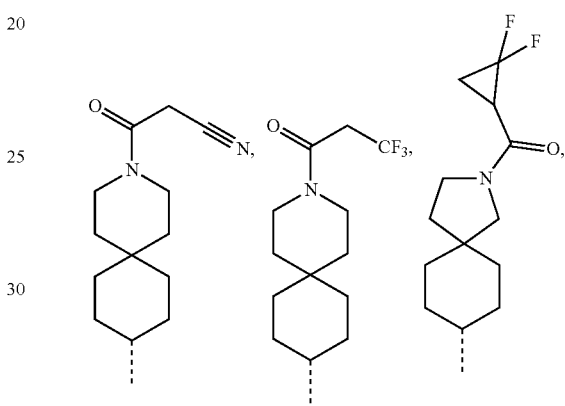
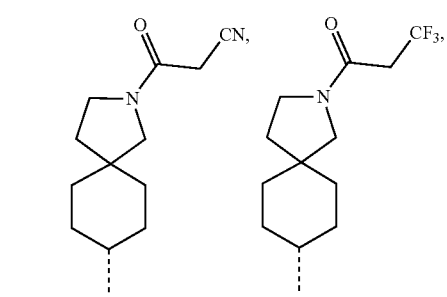
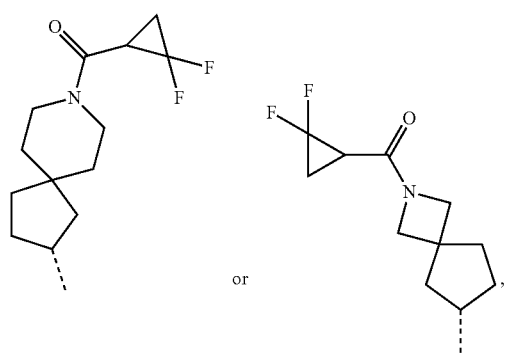 [SMILES: C[C@@H]1CCC2(CCN(C(=O)C3CC3(F)F)CC2)C1 ; C[C@H]1CCC2(C1)CN(C(=O)C1CC1(F)F)C2]

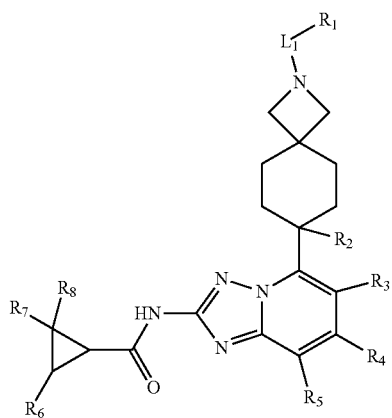 (I-1)
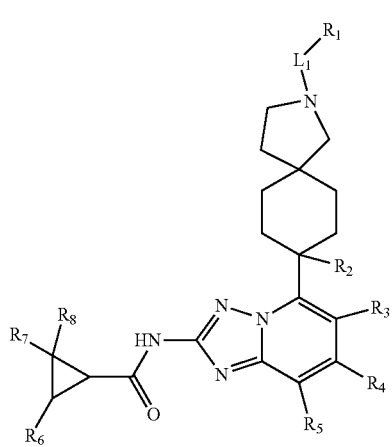 (I-2)
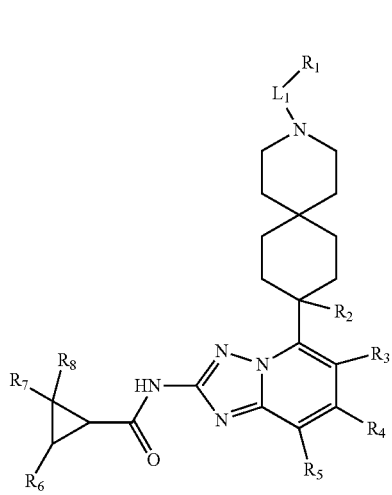 (I-3)
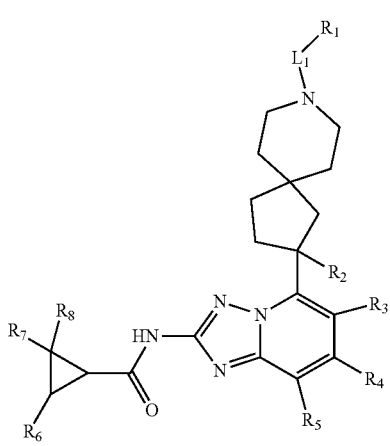 (I-4)
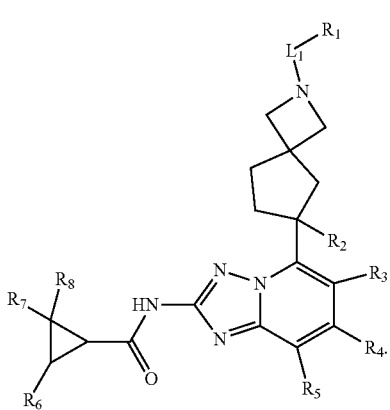 (I-5)
wherein,
$L_1$, $R_1$, $R_2$, $R_3$, $R_4$, $R_5$, $R_6$, $R_7$ and $R_8$ are as defined in the present invention.
In the present invention, as one of the embodiments, the compounds of formula (I), their isomers or its pharmaceutically acceptable salts are selected from
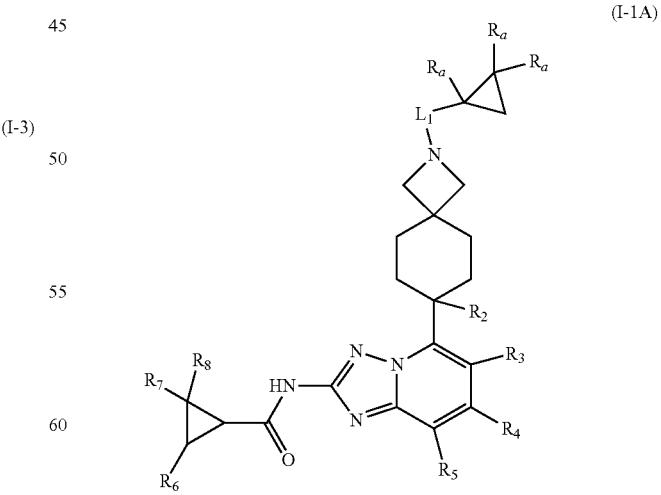 (I-1A)
wherein,
$L_1$, $R_4$, $R_2$, $R_3$, $R_4$, $R_5$, $R_6$, $R_7$ and $R_8$ are as defined in the present invention.

In the present invention, as one of the embodiments, the invention further provides the following compounds, isomers or pharmaceutically acceptable salts thereof:
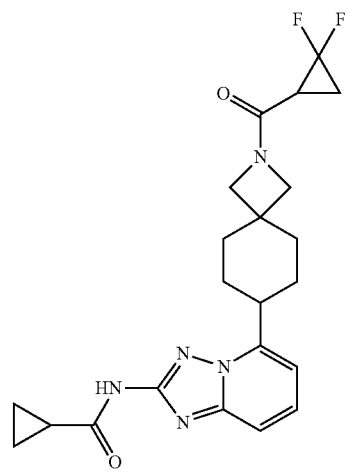
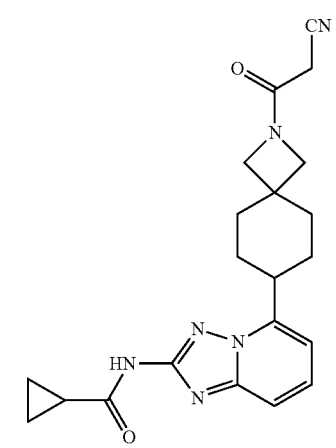
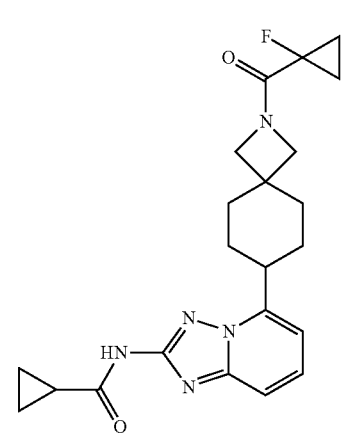
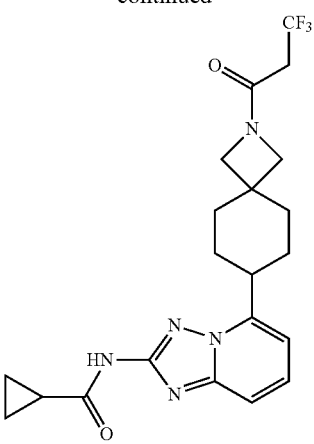
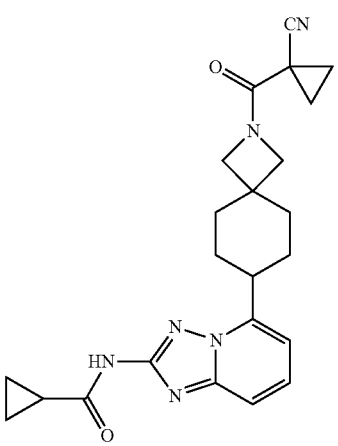
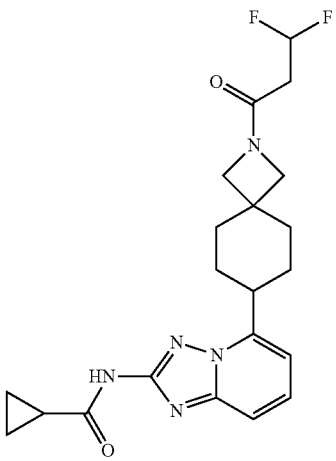

-continued
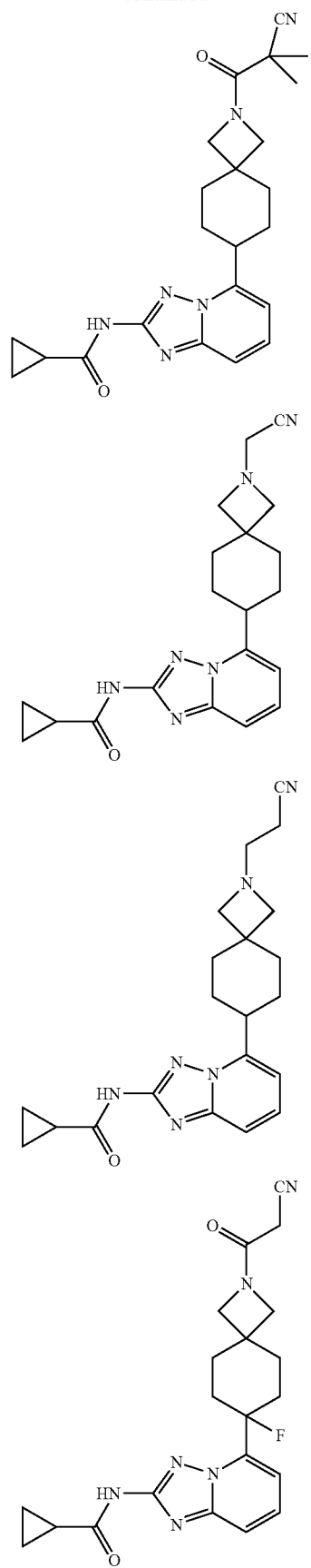
-continued
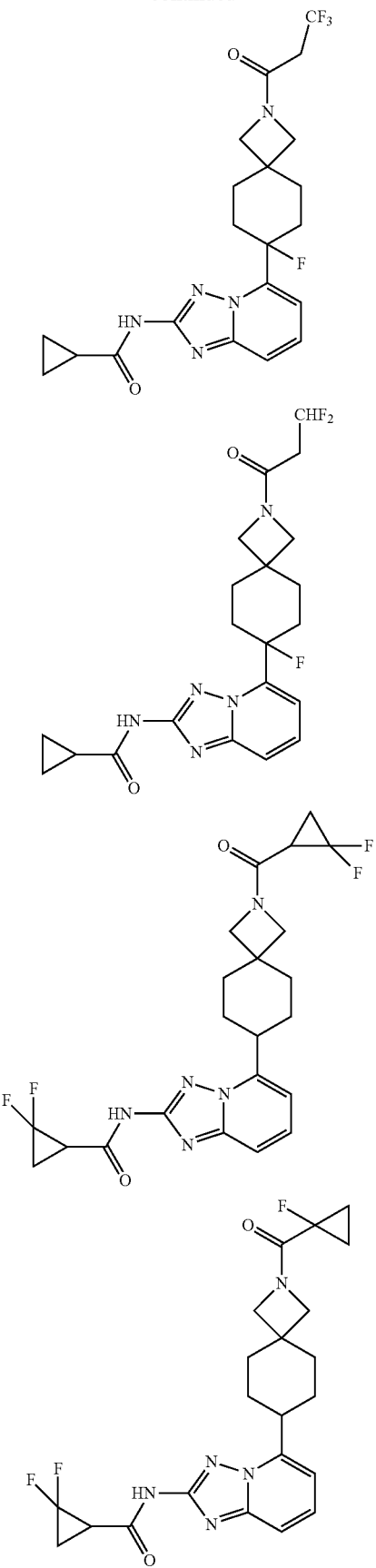

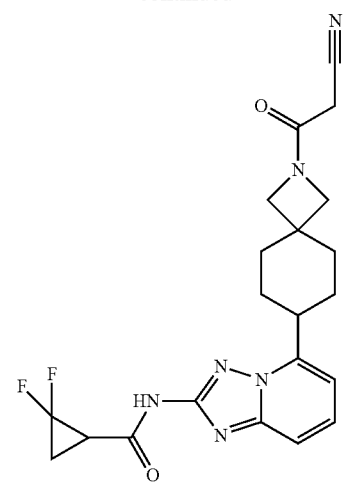
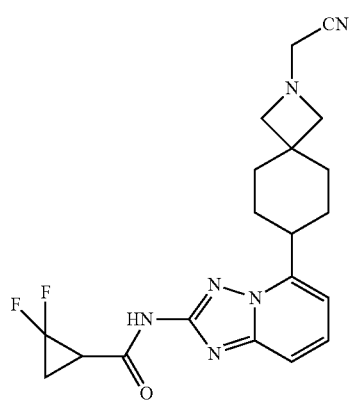
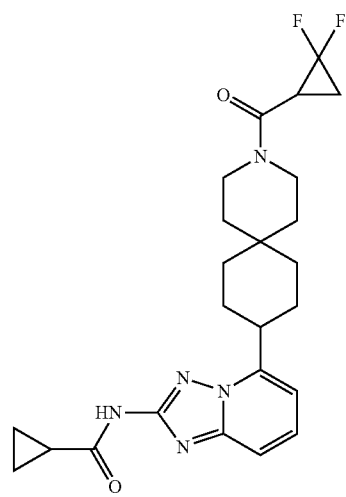
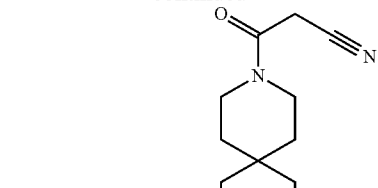
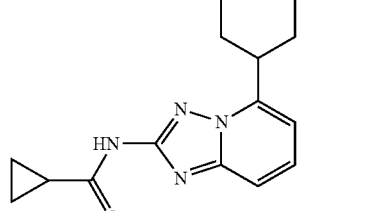
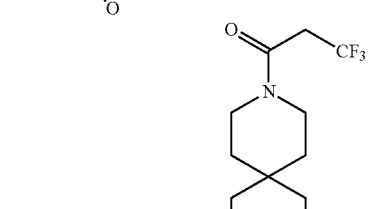
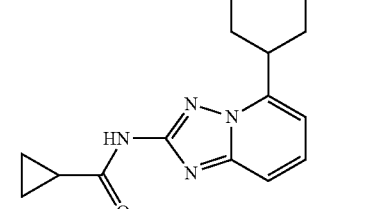
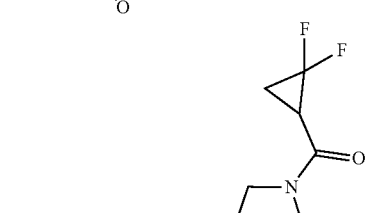

-continued
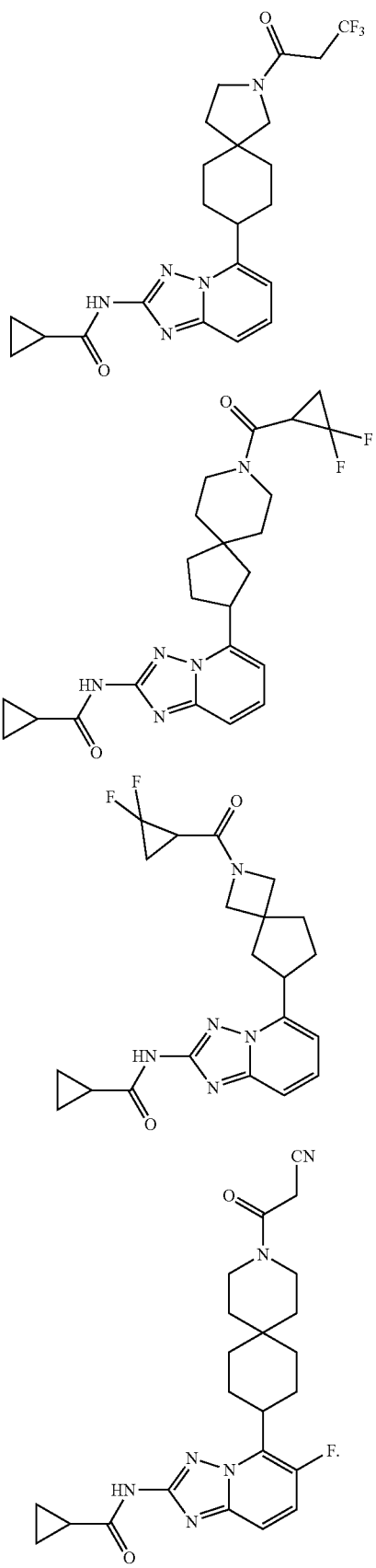
In the present invention, as one of the embodiments, the invention further provides the following compounds, isomers or pharmaceutically acceptable salts thereof:
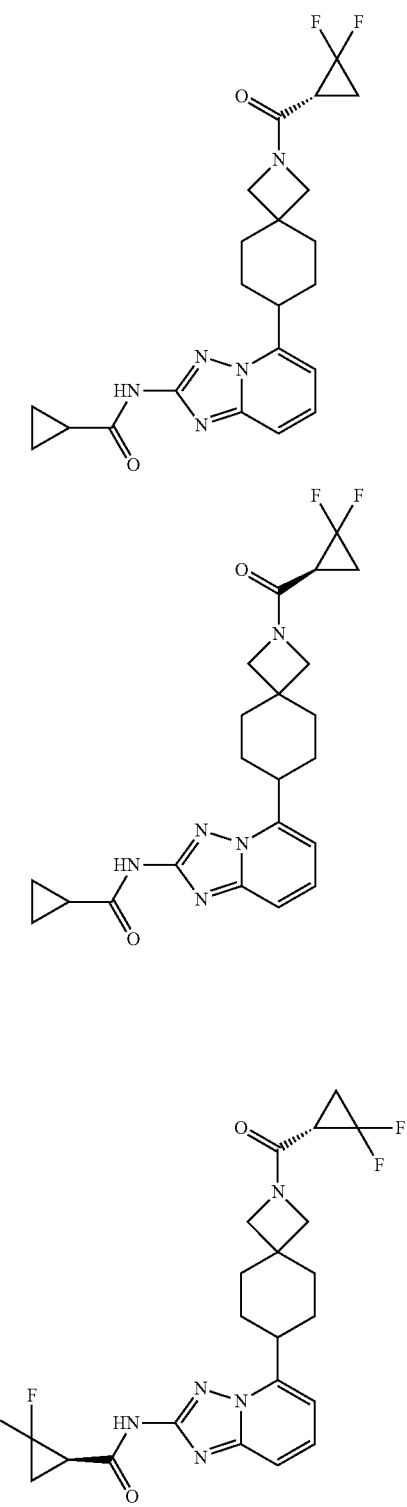

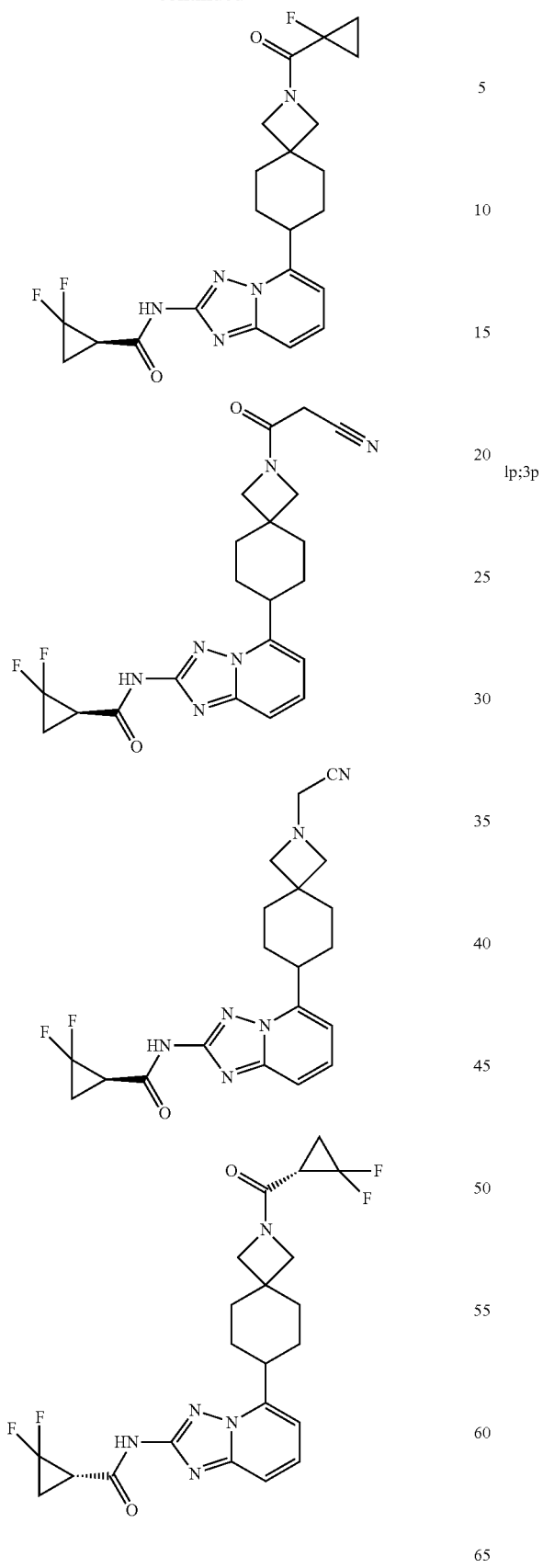
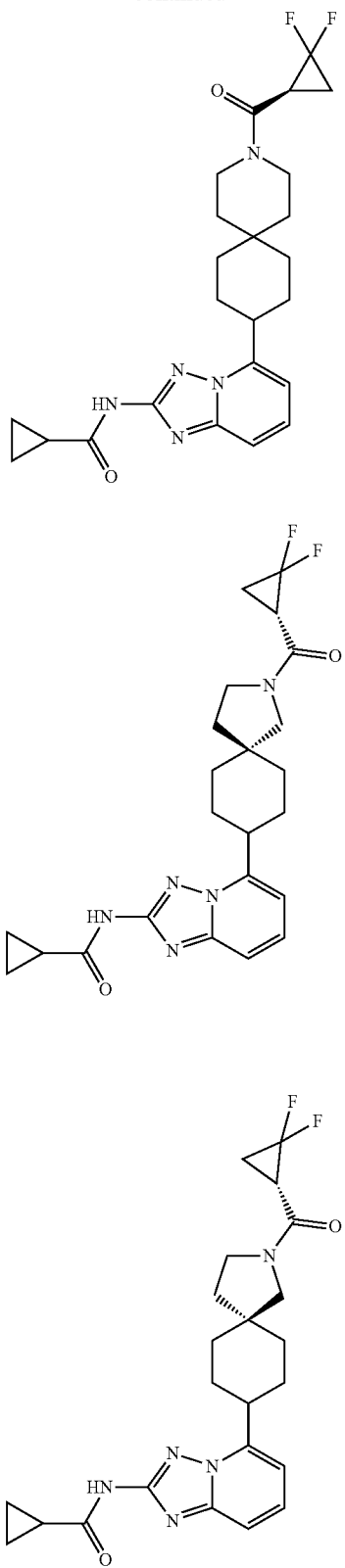

23
-continued
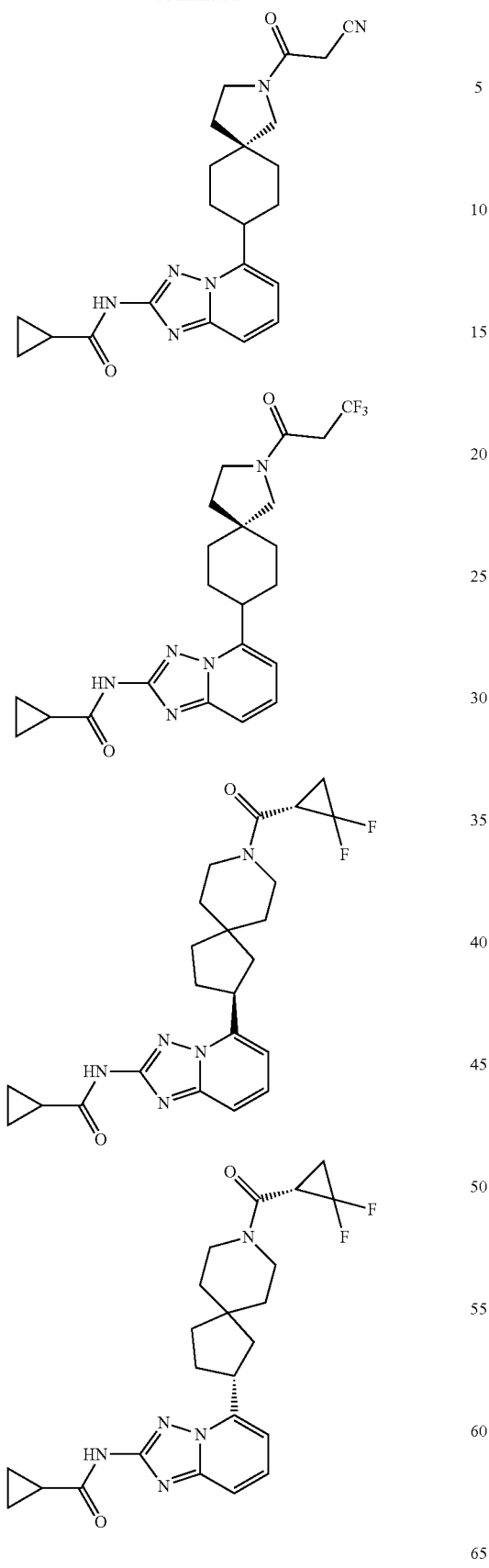
24
-continued
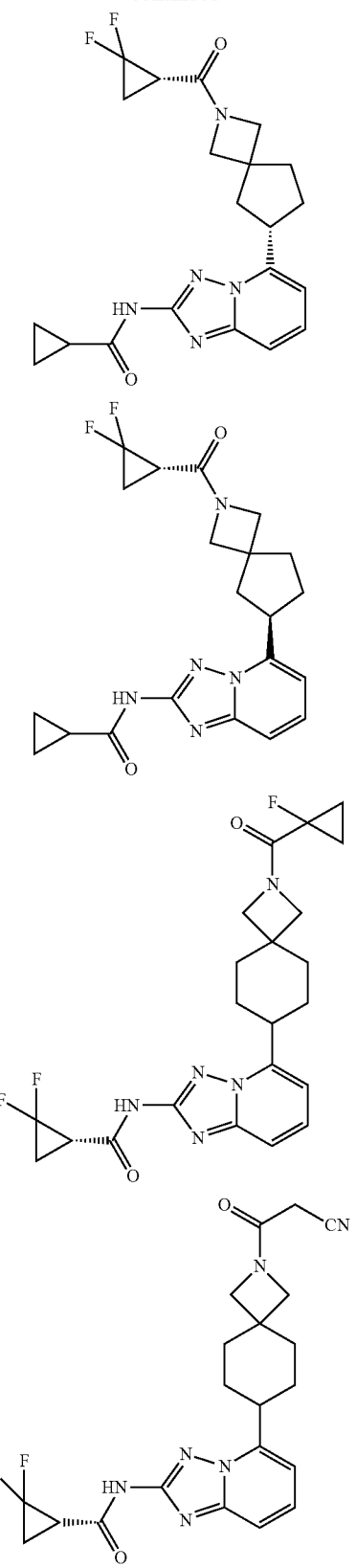

-continued

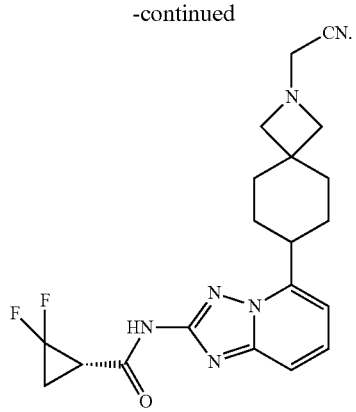

As one of the embodiments, the invention also provides a pharmaceutical composition, including a therapeutically effective amount of a compound of formula (I) as an active ingredient, an isomer thereof or a pharmaceutically acceptable salt thereof, and a pharmaceutically acceptable carrier.

Experiments have proved that, when the JAK inhibitors [1,2,4]triazolo[1,5-a]pyridine compounds of the present invention, such as formula (I), are used in the preparation of drugs for the treatment of autoimmune, inflammatory or allergic diseases, or transplant rejection, a series of compounds involved in the present invention show a good selective inhibition to JAK1 and/or TYK2 in the in vitro activity experiments of the four subtypes of JAK kinase (JAK1, JAK2, JAK3 and TYK2), and these compounds show high exposure and good oral bioavailability in pharmacokinetic experiments in mice. They have good efficacy in animal model tests of autoimmune, inflammatory or allergic diseases, especially in animal in vivo efficacy evaluation tests of inflammatory bowel disease and allergic dermatitis. The experiments show that compound 1-13 in the invention has the same or even better effect on treating inflammatory bowel disease at half the dose of Filgotinib, and compounds 1-8, 1-11, 1-13 and 9-3 have significant effect on treating allergic dermatitis, which is equivalent to the effect of Alonson.

Definition and Description

Unless otherwise stated, the following terms and phrases used herein are intended to have the following meanings. A specific phrase or term should not be considered uncertain or unclear without a special definition, but should be understood according to an ordinary meaning. When a trade name appears herein, it is intended to refer to its corresponding commodity or its active ingredients.

The term "pharmaceutically acceptable" used here refers to those compounds, materials, compositions and/or dosage forms that are suitable for use in contact with human and animal tissues within the scope of reliable medical judgment, without excessive toxicity, irritation, allergic reaction or other problems or complications, commensurate with a reasonable benefit/risk ratio.

The term "pharmaceutically acceptable salt" refers to a salt of a compound of the present invention, which is prepared from a compound with a specific substituent found in the present invention and a relatively non-toxic acid or base. When the compounds of the present invention contain relatively acidic functional groups, alkali addition salts can be obtained by contacting an sufficient amount of bases with the neutral form of such compounds in a pure solution or a suitable inert solvent. Pharmaceutically acceptable alkali addition salts include sodium, potassium, calcium, ammonium, organic amine or magnesium salt or similar salts. When the compounds of the present invention contain relatively basic functional groups, acid addition salts can be obtained by contacting a sufficient amount of acid with the neutral form of such compounds in a pure solution or a suitable inert solvent. Examples of pharmaceutically acceptable acid addition salts include salts of inorganic acids such as hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphite, etc; and salts of organic acid including similar acids such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluene sulfonic acid, citric acid, tartaric acid and methanesulfonic acid; and salts of amino acids (such as arginine) and organic acids such as glucuronic acid as well. Certain specific compounds of the present invention contain basic and acidic functional groups, and thus can be converted to any base or acid addition salt.

The pharmaceutically acceptable salt of the present invention can be synthesized by a conventional chemical method from a parent compound containing acid or basic group. Generally, such salts are prepared by reacting these compounds in the form of free acids or bases with stoichiometric appropriate bases or acids in water or organic solvents or mixtures of both.

The compounds of the present invention may exist in specific geometric or stereoisomeric forms. The present invention envisages all such compounds, including cis and trans isomers, (−)- and (+)-enantiomers, (R)- and (S)-enantiomers, diastereomers, (D)-isomers, (L)-isomers, racemic mixtures and other mixtures, such as enantiomers or diastereomer enriched mixtures, all of which fall within the scope of the present invention. Other asymmetric carbon atoms may exist in substituents such as alkyl groups. All these isomers and their mixtures are within the scope of the present invention.

Unless otherwise specified, the term "enantiomer" or "optically active isomer" refers to stereoisomers that are mirror images of each other.

Unless otherwise specified, the term "cis and trans isomer" or "geometric isomer" is caused by the fact that a double bond or a single bond of a ring forming carbon atom cannot rotate freely.

Unless otherwise specified, the term "diastereomer" refers to a stereoisomer in which a molecule has two or more chiral centers and the relationship between molecules is non mirror image.

Unless otherwise specified, "(D)" or "(+)" indicates dextral rotation, "(L)" or "(−)" indicates sinistral rotation, and "(DL)" or "(±)" indicates racemization.

Unless otherwise specified, the wedge-shaped solid key ( ) and the wedge-shaped dashed key ( ) are used to represent an absolute configuration of a stereocenter, the straight solid key ( ) and the straight dashed key ( ) are used to represent the relative configuration of the stereocenter, the wavy line ( ) is used to represent the wedge-shaped solid key ( ) or the wedge-shaped dashed key ( ), or the wavy line ( ) is used to represent the straight solid key ( ) and the straight dashed key ( ).

Unless otherwise specified, when there is a double bond in the compound, such as carbon carbon double bond, carbon nitrogen double bond and nitrogen nitrogen double bond, and each atom on the double bond is connected with two different substituents (in the double bond containing nitrogen atom, a pair of lone pair electrons on the nitrogen atom is regarded as a substituent connected), if the atom on the double bond in the compound is connected with its substituent by a wavy line ), Represents the (Z) isomer, (E) isomer or a mixture of two isomers of the compound. For example, the following formula (A) indicates that the compound exists as a single isomer of formula (A-1) or formula (A-2) or as a mixture of two isomers of formula (A-1) and formula (A-2); and the following formula (B) indicates that the compound exists as a single isomer of formula (B-1) or formula (b-2) or as a mixture of two isomers of formula (B-1) and formula (B-2). The following formula (C) indicates that the compound exists as a single isomer of formula (C-1) or formula (C-2) or as a mixture of two isomers of formula (C-1) and formula (C-2).

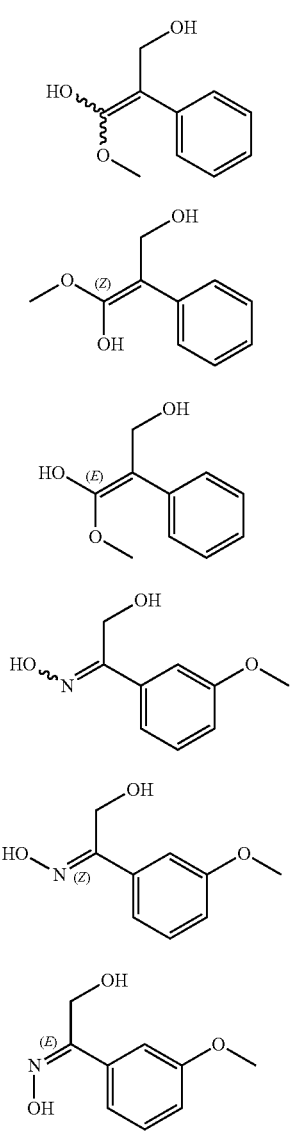

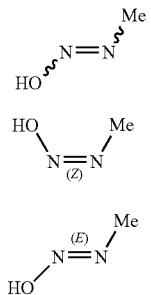

Unless otherwise specified, the term "tautomer" or "tautomer form" means that isomers of different functional groups are in dynamic equilibrium at room temperature and can be quickly converted to each other. If tautomers are possible (e.g. in solution), a chemical equilibrium of the tautomers can be achieved. For example, proton tautomer (also known as prototropic tautomer) includes interconversion through proton migration, such as keto-enol isomerization and imine-enamine isomerization. Valence tautomer includes the conversion of some bonding electrons by recombination. A specific example of keto-enol tautomerism is the tautomerism between pentane-2,4-dione and 4-hydroxypenta-3-ene-2-one tautomer.

Unless otherwise specified, the terms "rich in one isomer", "rich in isomer", "rich in one enantiomer" or "rich in enantiomer" mean that the content of one isomer or enantiomer is less than 100%, and the content of such isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "excessive isomer" or "excessive enantiomer" refers to the difference between the relative percentages of two isomers or two enantiomers. For example, if the content of one isomer or enantiomer is 90% and the content of the other isomer or enantiomer is 10%, the excess of isomer or enantiomer (ee value) is 80%.

Optically active (R)- and (S)-isomers and D and L isomers can be prepared by chiral synthesis or chiral reagents or other conventional techniques. If an enantiomer of a compound of the present invention is desired, it can be prepared by asymmetric synthesis or by derivatization with a chiral promoter, in which the resulting diastereomeric mixture is separated and the auxiliary group is split to provide a pure desired enantiomer. Alternatively, when the molecule contains an alkaline functional group (such as amino group) or an acidic functional group (such as carboxyl group), a salt of the diastereomer is formed with an appropriate optically active acid or base, and then the diastereomer is resolved by a conventional method known in the art, and then the pure enantiomer is recovered. In addition, the separation of enantiomers and diastereomers is usually accomplished by chromatography using a chiral stationary phase and optionally in combination with chemical derivatization (for example, the formation of carbamates from amines). The compounds of the present invention may contain atomic isotopes in unnatural proportions on one or more atoms. For example, radioisotopes may be used to label compounds such as tritium ($^3H$), iodine-125 ($^{125}I$), or C-14 ($^{14}C$). For another example, deuterated drugs can be formed by replacing hydrogen with deuterium. The bond between deuterium and carbon is stronger than that between hydrogen and carbon. Compared with non deuterated drugs, deuterated drugs have the advantages of reducing toxic and side effects, increasing drug stability, enhancing curative effect and prolonging the biological half-life of drugs. The transformation of all isotopic compositions of the compounds of the present invention, whether radioactive or not, is included in the scope of the present invention. "Optional" or "optionally" means that an event or condition described subsequently may, but not necessarily, occur, and the description includes the circumstances in which the event or condition occurs and the circumstances in which the event or condition does not occur.

The term "substituted" means that any one or more hydrogen atoms on a particular atom are substituted by a substituent, which may include deuterium and hydrogen variants, as long as the valence state of the particular atom is normal and the substituted compound is stable. When the substituent is oxygen (i.e. =o), it means that two hydrogen atoms are substituted. Oxygen substitution does not occur on aromatic groups. The term "optionally substituted" means that it may or may not be substituted. Unless otherwise specified, the type and number of substituents may be arbitrary on the basis that they are chemically achievable.

When any variable (such as R) appears more than once in the composition or structure of a compound, its definition in each case is independent. Thus, for example, if one group is replaced by 0-2 R, the group can optionally be replaced by at most two R, and in each case R has an independent option. In addition, combinations of substituents and/or variants thereof are permitted only if such combinations result in stable compounds.

When the number of a connecting group is 0, such as —(CRR)$_0$—, it means that the connecting group is a single bond.

When one of the variables is selected from the single bond, it means that the two groups are connected with each other directly. For example, when L represents the single bond in A-L-Z, it means that the structure is actually A-Z.

When a substituent is a vacancy, it means that the substituent does not exist. For example, when X in A-X is a vacancy, it means that the structure is actually A. When it is not indicated in the listed substituents which atom they are connected to the substituted group, such substituents can be bonded through any atom. For example, as a substituent, a pyridine group can be connected to the substituted group through any carbon atom on the pyridine ring.

When it is not indicated that what connection direction the listed connecting groups are connected in, the connecting direction is arbitrary. For example, the middle connecting group L in

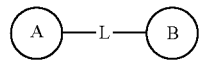

is -M-W—, then -M-W- can connect ring A and ring B in the same direction as the reading sequence from left to right to form

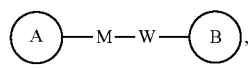

or connect ring A and ring B in the opposite direction as the reading sequence from left to right to form

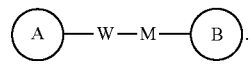

Combinations of the linking groups, substituents and/or variants thereof are permitted only if such combinations result in stable compounds.

Unless otherwise specified, the number of atoms on a ring is usually defined as the number of elements of the ring. For example, "5-7 element ring" refers to a "ring" with 5-7 atoms arranged around it.

Unless otherwise specified, "5- to 6-membered ring" represents cycloalkyl, heterocycloalkyl, cycloalkenyl, heterocycloalkenyl, cycloalkynyl, heterocycloalkynyl, aryl or heteroaryl composed of 5 to 6 ring atoms. The ring comprises a single ring and a double ring system such as a helical ring, a union ring and a bridge ring. Unless otherwise specified, the ring optionally comprises 1, 2 or 3 heteroatoms independently selected from O, S and N. The 5- to 6-membered ring includes 5-membered ring, 6-membered ring, etc. "5- to 6-membered ring" includes, for example, phenyl, pyridyl, piperidinyl, etc. On the other hand, the term "5- to 6-membered heterocycloalkyl" includes piperidinyl and the like, but does not include phenyl.

The term "ring" also includes a ring system containing at least one ring, each of which independently conforms to the above definition.

Unless otherwise specified, the term "$C_{1-6}$ alkyl" is used to denote a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl. It can be monovalent (e.g. methyl), divalent (e.g. methylene), or multivalent (e.g. methylene). Examples of $C_{1-6}$ alkyl include, but not limited to, methyl (Me), ethyl (Et), propyl (including n-propyl and isopropyl), butyl (including n-butyl, isobutyl, s-butyl and t-butyl), amyl (including n-amyl, isopentyl and neopentyl), hexyl, and the like.

Unless otherwise specified, the term "$C_{1-3}$ alkyl" is used to denote a linear or branched saturated hydrocarbon group consisting of 1 to 3 carbon atoms. The $C_{1-3}$ alkyl group includes $C_{1-2}$ and $C_{2-3}$ alkyl groups. It can be monovalent (e.g. methyl), divalent (e.g. methylene), or multivalent (e.g. methylene). Examples of $C_{1-3}$ alkyl groups include, but not limited to, methyl (Me), ethyl (Et), propyl (including n-propyl and isopropyl), and the like.

Unless otherwise specified, "$C_{3-6}$ cycloalkyl" refers to a saturated cyclic hydrocarbon group composed of 3 to 6 carbon atoms, which is a monocyclic and bicyclic system. The $C_{3-6}$ cycloalkyl includes $C_{3-5}$, $C_{4-5}$ and $C_{5-6}$ cycloalkyl. It can be monovalent, bivalent or multi-valent. Examples of $C_{3-6}$ cycloalkyl include, but not limited to, cyclopropyl, cyclobutyl, cyclopentyl, cyclohexyl, and the like.

Unless otherwise specified, $C_{n-n+m}$ or $C_n$—$C_{n+m}$ includes any specific case of n to n+m carbon, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$. Similarly, n to n+m membered ring means that the number of atoms on the ring is n to n+m, for example, the 3- to 12-membered ring includes 3-membered ring, 4-membered ring, 5-membered ring, 6-membered ring, 7-membered ring, 8-membered ring, 9-membered ring, 10-membered ring, 11-membered ring and 12-membered ring, and also includes any range from n to n+m, for example, the 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring, etc.

The compounds of the present invention can be prepared by a variety of synthesis methods well known to those skilled in the art, including the specific embodiments listed below, the embodiments formed by its combination with other chemical synthesis methods, and the equivalent replacement methods well known to those skilled in the art. The preferred embodiments include but not limited to the embodiments of the present invention.

The solvent used in the invention can be commercially available. The invention adopts the following abbreviations: aq stands for water; HATU stands for O-(7-azabenzotriazole-1-yl)-N, N, N',N'-tetramethylurea hexafluorophosphate; EDC stands for N-(3-dimethylaminopropyl)-N'-ethyl carbodiimide hydrochloride; m-CPBA stands for 3-chloroperoxybenzoic acid; eq stands for equivalent and equivalent quantity; CDI stands for carbonyldiimidazole; DCM stands for methylene chloride; PE stands for petroleum ether; DIAD stands for diisopropyl azodicarboxylate; DMF stands for N,N-dimethylformamide; DMSO stands for dimethyl sulfoxide; EtOAc stands for ethyl acetate; EtOH stands for ethanol; MeOH stands for methanol; CBz stands for benzyloxycarbonyl, which is an amine protective group; Boc stands for tert butoxycarbonyl, which is an amine protective group; HOAc stands for acetic acid; NaCNBH$_3$ stands for sodium cyanobohydride; r. t. represents room temperature; O/N stands for overnight; THF stands for tetrahydrofuran; Boc$_2$O stands for di-tert butyl dicarbonate; TFA stands for trifluoroacetic acid; DIPEA stands for diisopropyl ethyl amine; SOCl$_2$ stands for thionyl chloride; CS$_2$ stands for carbon disulfide; TsOH stands for p-toluenesulfonic acid; NFSI stands for N-fluoro-N-(benzenesulfonyl) benzenesulfonamide; NCS stands for 1-chloropyrro-lidine-2,5-dione; n-Bu4NF stands for tetrabutylammonium fluoride; i-PrOH stands for 2-propanol; mp stands for melting point; LDA stands for diisopropylaminolithium; Pd(dppf)Cl$_2$—CH$_2$Cl$_2$ represents the dichloromethane complex of [1,1'-bis(diphenylphosphino)ferrocene]palladium dichloride; EDCI stands for N-(3-dimethylaminopropyl)-N'-ethyl carbodiimide hydrochloride; DIEA stands for N,N-Diisopropyl ethylamine; IPA stands for isopropanol; HOBt stands for 1-hydroxybenzotriazole; LiHMDS stands for hexamethyldisilicylaminolithium; TEA stands for triethylamine; HEPES stands for 4-hydroxyethyl piperazine ethanesulfonic acid; LiHMDS stands for hexamethyl disilicyl aminolithium; Pd/C stands for palladium carbon; METHANOL stands for methanol; KOAc stands for potassium acetate; and K$_2$CO$_3$ stands for potassium carbonate.

Compounds are named manually or by ChemDraw® software, and the name of the supplier's catalog shall be used for the commercial compounds.

DETAILED DESCRIPTION

Figure 1:
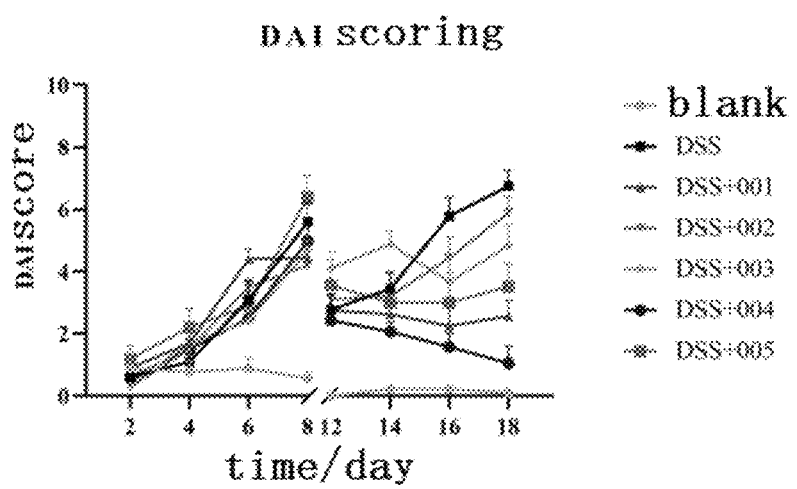
FIG. 1: curve diagram of DAI scoring results in experimental example 3.

The present invention will be described in detail below by way of examples, but does not imply any adverse limitation to the present invention. The present invention has been described in detail herein, and specific embodiments thereof have also been disclosed. It will be apparent to those skilled in the art to make various changes and improvements to the specific embodiments of the present invention without departing from the spirit and scope of the present invention.

Example 1

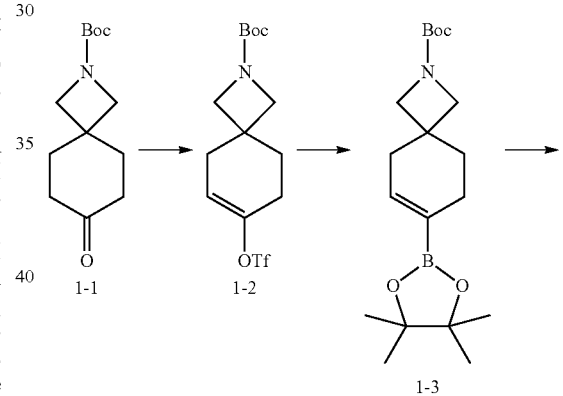

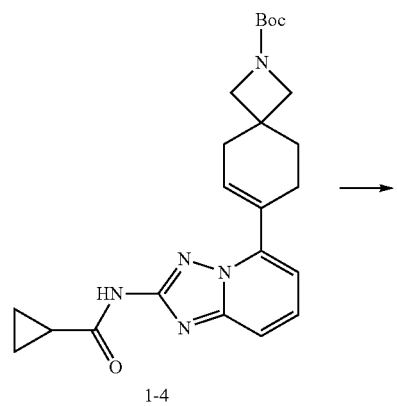

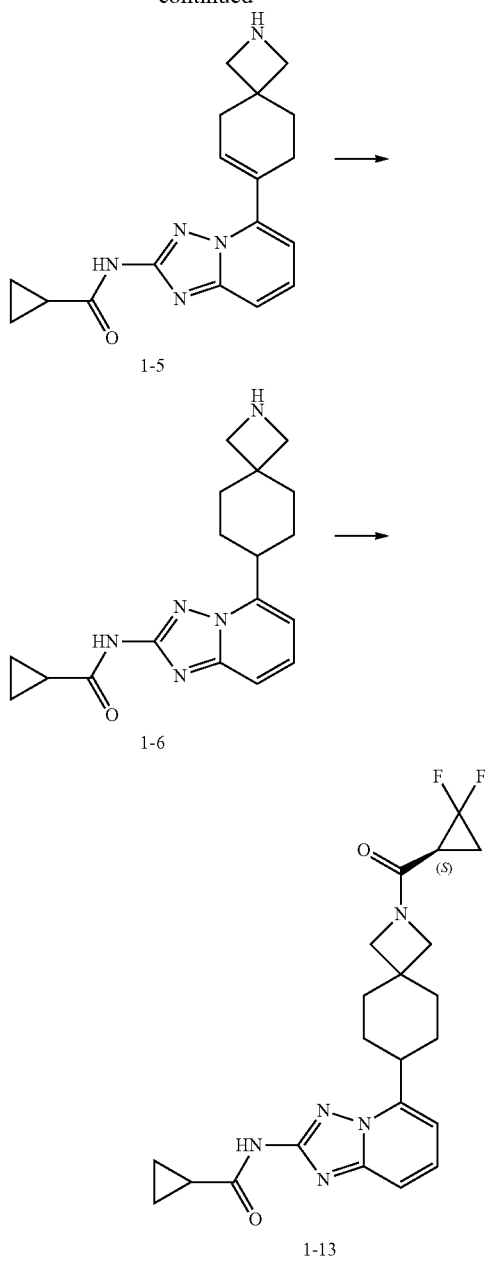

¹H NMR (400 MHz, CDCl₃) δ 5.63 (br s, 1H), 3.50-3.65 (m, 4H), 2.34 (br s, 4H), 1.88 (br t, J=5.90 Hz, 2H), 1.37 (s, 9H).

Step 2: a DMF (100 mL) solution containing Compound 1-2 (16.0 g, 43.1 mmol) and pinacol borate (12.0 g, 47.4 mmol) was added with potassium acetate (12.7 g, 129.3 mmol) and Pd (dppf)Cl₂CH₂Cl₂ (3.5 g, 4.3 mmol), replaced with nitrogen for 3 times and stirred at 70° C. in nitrogen atmosphere for 3 hours. TLC showed that raw materials were consumed completely and new points were generated. The reaction solution was dispersed in a mixture of 300 mL of water and 400 mL of ethyl acetate. The organic phase was separated and washed with saturated salt water, dried with sodium sulfate, then filtered and concentrated to obtain a crude product. The crude product was purified by silica gel chromatography to obtain Compound 1-3. ¹H NMR (400 MHz, CDCl₃) δ6.46 (br s, 1H), 3.71-3.53 (m, 4H), 2.31 (br d, J=3.0 Hz, 2H), 2.24-2.16 (m, 2H), 1.74 (t, J=6.3 Hz, 2H), 1.44 (s, 9H), 1.26 (s, 12H).

Step 3: potassium carbonate (3.8 g, 27.3 mmol) and Pd(dppf)Cl₂·CH₂Cl₂ (744 mg, 911.0 μmol) were added to a dioxane (60 mL) and water (15 mL) solution containing Compound 1-3 (3.5 g, 10.0 mmol) and N-(5-bromo-[1,2,4]triazolo[1,5-a]pyridin-2-yl) cyclopropane formamide (2.6 g, 9.1 mmol) in nitrogen atmosphere. The reaction solution was stirred at 90° C. for 3 hours. LCMS showed that the raw materials were completely consumed and the target molecular ion peak was monitored. The reaction solution was concentrated, and the obtained crude product was separated and purified by column chromatography to obtain Compound 1-4. LCMS (ESI) m/z: 424.3[M+H]⁺.

Step 4: hydrochloric acid/ethyl acetate (4.0 M, 30 mL) was added to a dichloromethane (10 mL) solution containing Compound 1-4 (3.5 g, 8.2 mmol), and the mixture was stirred at 25° C. for 0.5 hours. LCMS showed that the raw material was consumed and the target molecular ion peak was monitored. The solid was precipitated, then filtered and dried to obtain Compound 1-5 (3.3 g hydrochloride, crude product), which was not purified and used for the next reaction directly. LCMS (ESI) m/z: 324.1[M+H]⁺.

Step 5: Pd/C (1.0 g, 10%) was added to a methanol (100 mL) solution containing Compound 1-5 (3.0 g, 8.34 mmol, hydrochloride) in nitrogen atmosphere. The suspension was replaced with hydrogen for 3 times and then stirred for 12 hours at 30° C. in hydrogen atmosphere (30 psi). LCMS showed that the raw material was consumed and the target molecular ion peak was monitored. The reaction solution was filtered and concentrated to obtain Compound 1-6 (3.0 g hydrochloride, crude product), which was not purified and used for the next reaction directly. LCMS (ESI) m/z: 326.2 [M+H]⁺.

Step 6: Compound 1-6 (0.87 g, 2.40 mmol, hydrochloride) was dissolved in N, N-dimethylformamide (10 mL), HOBt (487 mg, 3.6 mmol,) and EDCI (691 mg, 3.6 mmol) were added, and then (1S)-2,2-difluorocyclopropyl formic acid (323 mg, 2.6 mmol) and diisopropyl ethylamine (621 mg, 4.8 mmol) were added into the reaction solution. The reaction solution was reacted at 15° C. for 12 hours. LC-MS showed the reaction was complete. The reaction solution was concentrated under reduced pressure, and a residue was subjected to preparative HPLC (neutral system) to obtain Compound 1-13: ¹H NMR (400 MHz, METHANOL-d₄) δ7.32-7.73 (m, 2H), 6.95 (br s, 1H), 3.62-4.22 (m, 4H), 3.45 (br s, 1H), 3.18-3.37 (m, 1H), 2.61 (br s, 1H), 1.45-2.27 (m, 10H), 0.78-1.17 (m, 4H). LCMS (ESI) m/z: 430.0[M+H]⁺.

Compound 1-6 was used as the common intermediate, the following compounds were obtained by the same synthesis and separation method as compound 1-13 (i.e. replacing the carboxylic acid of compound 1-13 with the corresponding carboxylic acid in the following target molecules in the acid amine condensation reaction step). The characterization data are as follows:
1-7
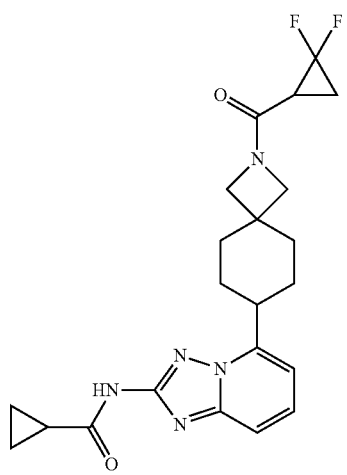
1-8
1-9
1-10
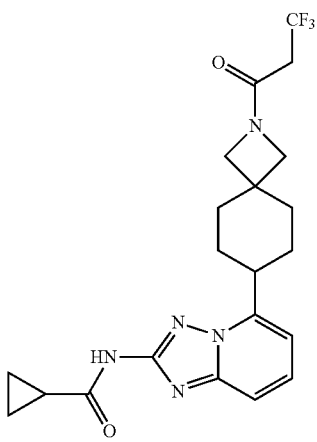
1-11
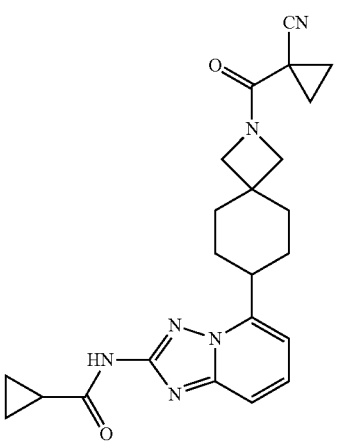
1-12
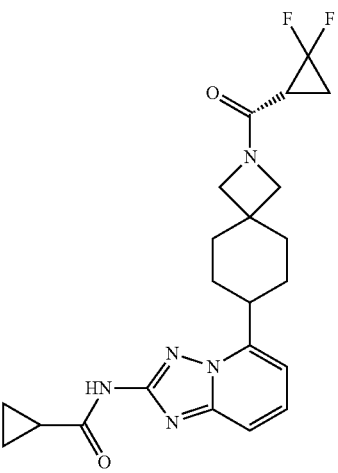

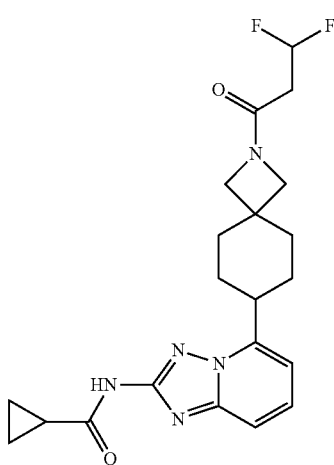

1-14

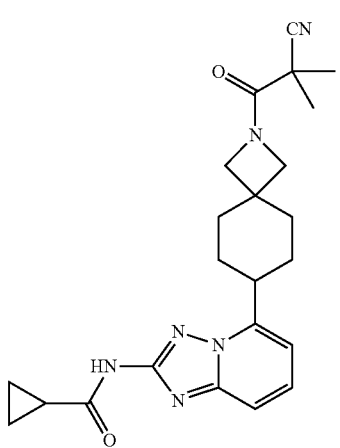

1-15

Compound 1-7: ¹H NMR (400 MHz, DMSO-d₆) δ 11.08 (br s, 1H), 7.48-7.78 (m, 2H), 7.03 (d, J=7.0 Hz, 1H), 3.86-4.25 (m, 2H), 3.61-3.80 (m, 2H), 3.29-3.38 (m, 1H), 2.69-2.88 (m, 1H), 1.85-2.19 (m, 7H), 1.51-1.79 (m, 4H), 0.83-0.96 (m, 4H). LCMS (ESI) m/z: 430.0[M+H]⁺.

Compound 1-8: ¹H NMR (400 MHz, DMSO-d₆) δ 11.14 (br s, 1H), 7.52-7.66 (m, 2H), 7.00 (d, J=7.03 Hz, 1H), 3.54-3.83 (m, 6H), 3.29 (br t, J=11.54 Hz, 1H), 1.94-2.09 (m, 5H), 1.41-1.70 (m, 4H), 0.77-0.90 (m, 4H). LCMS (ESI) m/z: 393.1[M+H]⁺.

Compound 1-9: ¹H NMR (400 MHz, DMSO-d₆) δ 10.99 (br s, 1H), 7.49-7.65 (m, 2H), 6.99 (br d, J=7.03 Hz, 1H), 4.02-4.20 (m, 2H), 3.61-3.78 (m, 2H), 1.94-2.13 (m, 5H), 1.48-1.72 (m, 4H), 1.14-1.32 (m, 4H), 0.77-0.87 (m, 4H). LCMS (ESI) m/z: 412.1[M+H]⁺.

Compound 1-10: ¹H NMR (400 MHz, METHANOL-d₄) δ 7.77-7.87 (m, 1H), 7.62 (d, J=8.78 Hz, 1H), 7.20 (dd, J=7.28, 11.80 Hz, 1H), 4.08 (s, 1H), 3.96 (s, 1H), 3.83 (s, 1H), 3.72 (s, 1H), 3.43-3.56 (m, 1H), 3.22 (dq, J=6.90, 10.75 Hz, 2H), 2.06-2.23 (m, 4H), 1.94 (br s, 1H), 1.56-1.84 (m, 3H), 1.56-2.00 (m, 1H), 0.94-1.14 (m, 4H). LCMS (ESI) m/z: 436.1[M+H]⁺.

Compound 1-11: ¹H NMR (400 MHz, METHANOL-d₄) δ 7.56-7.67 (m, 1H), 7.50 (d, J=8.78 Hz, 1H), 7.00 (t, J=7.15 Hz, 1H), 4.26-4.48 (m, 2H), 3.70-3.90 (m, 2H), 3.42-3.59 (m, 1H), 2.08-2.24 (m, 4H), 1.48-1.99 (m, 9H), 0.87-1.10 (m, 4H). LCMS (ESI) m/z: 419.1[M+H]⁺.

Compound 1-12: ¹H NMR (400 MHz, METHANOL-d₄) δ 7.56-7.64 (m, 1H), 7.48 (d, J=9.03 Hz, 1H), 6.97 (d, J=7.28 Hz, 1H), 3.91-4.17 (m, 2H), 3.78-3.86 (m, 1H), 3.67-3.75 (m, 1H), 3.40-3.54 (m, 1H), 2.53-2.69 (m, 1H), 1.92-2.21 (m, 6H), 1.72-1.85 (m, 3H), 1.50-1.69 (m, 2H), 0.86-1.08 (m, 4H). LCMS (ESI) m/z: 430.1[M+H]⁺.

Compound 1-14: ¹H NMR (400 MHz, METHANOL-d₄) δ 7.57-7.66 (m, 1H), 7.50 (d, J=8.78 Hz, 1H), 6.95-7.03 (m, 1H), 6.01-6.38 (m, 1H), 4.62 (s, 1H), 3.65-4.10 (m, 4H), 3.43-3.58 (m, 1H), 2.76-2.93 (m, 2H), 2.04-2.21 (m, 4H), 1.51-1.87 (m, 4H), 1.01-1.07 (m, 2H), 0.93 (qd, J=3.74, 7.34 Hz, 2H). LCMS (ESI) m/z: 418.1[M+H]⁺.

Compound 1-15: ¹H NMR (400 MHz, DMSO-d₆) δ 11.01 (br s, 1H), 7.48-7.66 (m, 2H), 7.00 (dd, J=7.53, 9.79 Hz, 1H), 4.11-4.33 (m, 2H), 3.60-3.81 (m, 2H), 3.25-3.32 (m, 1H), 2.03 (br t, J=9.03 Hz, 5H), 1.53-1.73 (m, 4H), 1.49 (d, J=4.77 Hz, 6H), 0.76-0.88 (m, 4H). LCMS (ESI) m/z: 421.1[M+H]⁺.

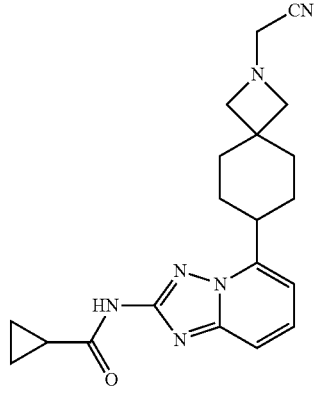

1-16

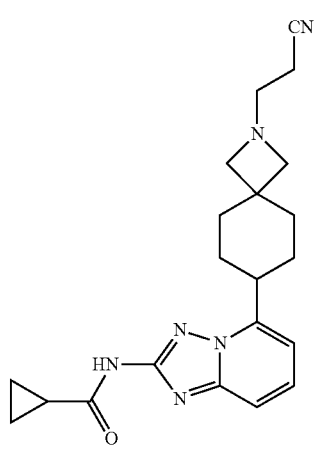

1-17

Synthesis of compound 1-16: Compound 1-6 (100 mg, 227.6 μmol, TFA) was dissolved in N,N-dimethylformamide (5 mL), potassium carbonate (94 mg, 682.7 μmol) and 2-bromoacetonitrile (30 mg, 250.3 μmol) were added, and it was stirred at 10° C. for 12 hours. LC-MS showed the reaction was complete. The reaction solution was diluted with water (5 mL), and extracted with dichloromethane/methanol (10/1, 10 mL). The organic phase was washed with saturated salt water (10 mL), dried with anhydrous sodium sulfate, then filtered and concentrated under reduced pressure. The residue was purified by preparative HPLC (neutral system) to obtain Compound 1-16. ¹H NMR (400 MHz, METHANOL-d₄) δ 7.83 (t, J=8.03 Hz, 1H), 7.64 (br d, J=8.78 Hz, 1H), 7.21 (d, J=7.53 Hz, 1H), 4.51 (s, 2H), 4.23 (s, 2H), 4.08 (s, 2H), 3.49 (br t, J=11.92 Hz, 1H), 2.14-2.30

(m, 4H), 1.79-1.97 (m, 3H), 1.59-1.74 (m, 2H), 0.95-1.12 (m, 4H). LCMS (ESI) m/z: 365.0[M+H]⁺.

Compounds 1-6 was used as a common intermediate, the following compounds were obtained by the same synthesis and separation methods as for Compound 1-16 (replacing bromoacetonitrile with corresponding bromopropiononitrile in the target molecule).

Compound 1-17: ¹H NMR (400 MHz, DMSO-d$_6$) δ11.00 (br s, 1H), 7.50-7.63 (m, 2H), 6.96 (d, J=6.27 Hz, 1H), 3.33-3.34 (m, 2H), 3.23-3.30 (m, 1H), 2.95 (s, 2H), 3.05 (s, 2H), 2.58-2.69 (m, 2H), 1.99 (br d, J=10.29 Hz, 5H), 1.40-1.65 (m, 4H), 0.74-0.88 (m, 4H). LCMS (ESI) m/z: 379.0[M+H]⁺.

Example 2

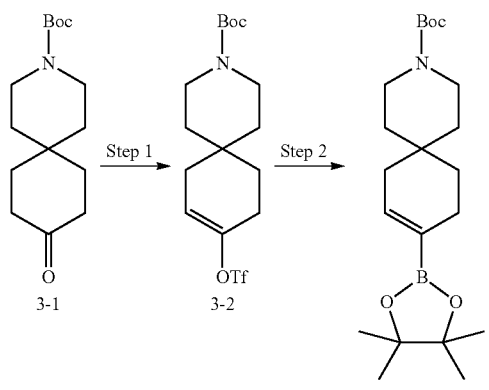

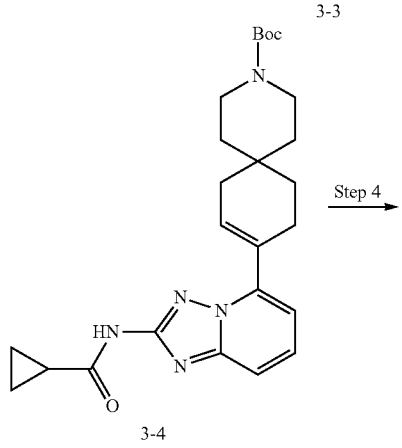

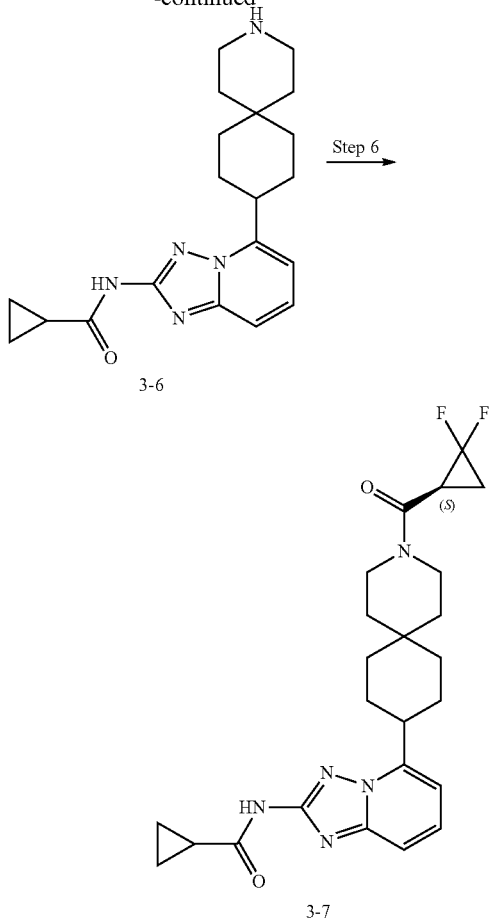

Step 1: tert butyl 9-oxygen-3-azaspiro[5.5] undecane-3-carboxylic acid (3-1) (5 g, 18.7 mmol) was dissolved in anhydrous tetrahydrofuran (150 mL) at −78° C. under the protection of nitrogen, dropped with bis(trimethylsilyl) lithium amino (1 M, 22.4 mL) slowly, and reaction solution was stirred at −78° C. for 1 hour. Then, the reaction solution was added with anhydrous tetrahydrofuran (50 mL) solution of 1,1,1-trifluoro-N-phenyl-N-((trifluoromethyl) sulfonyl) methanesulfonamide (7.35 g, 20.6 mmol), and the reaction solution was stirred at 15° C. for 12 hours. TLC showed the reaction was complete. The reaction solution was quenched with saturated ammonium chloride (50 mL) and extracted with ethyl acetate (200 mL*2). The combined organic phases were washed with saturated salt water (50 mL), dried with anhydrous sodium sulfate, then filtered and concentrated under reduced pressure to obtain Compound 3-2, which was directly used in the next step without purification.

Step 2: Compound 3-2 (8 g, 20.0 mmol) and pinacol diboroate (5.59 g, 22.0 mmol) were dissolved in N, N-dimethylformamide (100 mL), potassium acetate (5.90 g, 60.1 mmol) and [1,1-bis(diphenylphosphine)ferrocene]palladium dichloride dichloromethane (1.64 g, 2.0 mmol) were added, and stirred at 70° C. for 3 hours. TLC showed the reaction was complete. The reaction solution was diluted with water (300 mL) and extracted with ethyl acetate (200 mL*2). The combined organic phases were washed with saturated salt water (150 mL), dried with anhydrous sodium sulfate, then filtered and concentrated under reduced pressure. The residue was separated by rapid silica gel column (0~10% ethyl acetate/petroleum ether) to obtain compound 3-3. ¹H NMR (400 MHz, CDCl₃) δ6.41 (br s, 1H), 6.34-6.47 (m, 1H), 3.32-3.44 (m, 2H), 3.14-3.29 (m, 2H), 2.00-2.10 (m, 2H), 1.90 (br d, J=3.01 Hz, 2H), 1.38 (s, 9H), 1.28 (br t, J=5.52 Hz, 4H), 1.19 (s, 12H).

Step 3: under the protection of nitrogen, N-(5-bromo-[1,2,4]triazole[1,5-a] pyridin-2-yl) cyclopropylformamide (2 g, 7.1 mmol) was dissolved in mixed solution of dioxane (40 mL) and water (10 mL), Compound 3-3 (3.49 g, 9.3 mmol), potassium carbonate (2.95 g, 21.3 mmol), and [1,1-bis (diphenylphosphine) ferrocene] palladium dichloride dichloromethane (581 mg, 711.5 µmol) were added into the solution. It was replaced with nitrogen for 3 times, and heated to 90° C. to react for 3 hours. LC-MS showed the reaction was complete. The reaction solution was concentrated under reduced pressure, and the residue was separated by rapid silica gel column (0~4% methanol/dichloromethane) to obtain Compound 3-4. LCMS (ESI) m/z: 452.4[M+H]⁺.

Step 4: Compound 3-4 (3.5 g, 7.8 mmol) was dissolved in dichloromethane (15 mL), hydrochloric acid/ethyl acetate (4 M, 30 mL) was added, and the reaction solution was stirred at 20° C. for 30 minutes. LC-MS showed the reaction was complete. The solid was precipitated, filtered and dried to obtain Compounds 3-5. LCMS (ESI) m/z: 352.2[M+H]⁺.

Step 5: under the protection of N₂, Compound 3-5 (2.9 g, 7.4 mmol, hydrochloride) was dissolved in methanol (100 mL) solution, catalyst dry palladium/carbon (1 g, 10%) was added, and the reaction solution was replaced with hydrogen for 3 times. The reaction solution was stirred for 12 hours under hydrogen pressure (30 psi) and reaction temperature of 25° C. LC-MS showed the reaction was complete. The solid was filtered using diatomite and the filtrate was concentrated under reduced pressure to obtain Compound 3-6 (2.6 g hydrochloride). LCMS (ESI) m/z: 354.7[M+H]⁺.

Step 6: Compound 3-6 (1 g, 2.6 mmol, hydrochloride) was dissolved in N, N-dimethylformamide (20 mL), HOBt (573 mg, 4.2 mmol) and EDCI (813 mg, 4.2 mmol) were added, and then (ES)-2,2-difluorocyclopropyl carboxylic acid (380 mg, 3.1 mmol) and diisopropyl ethylamine (731 Mg, 5.7 mmol) were added. The reaction solution was reacted at 15° C. for 12 hours. LC-MS showed the reaction was complete. The reaction solution was diluted with water (100 mL), and extracted with dichloromethane/methanol (10/1, 150 mL*2). The combined organic phase was washed with saturated salt water (100 mL), dried with anhydrous sodium sulfate, then filtered and concentrated under reduced pressure. The residue was subjected to a preparative HPLC (neutral system) to obtain Compound 3-7.

¹H NMR (400 MHz, METHANOL-d₄) δ 7.57-7.64 (m, 1H), 7.48 (d, J=8.78 Hz, 1H), 7.02 (d, J=7.28 Hz, 1H), 3.63-3.77 (m, 3H), 3.41-3.61 (m, 2H), 2.93 (dt, J=8.28, 11.80 Hz, 1H), 1.36-2.06 (m, 15H), 1.04 (quin, J=3.76 Hz, 2H), 0.93 (qd, J=3.66, 7.34 Hz, 2H). LCMS (ESI) m/z: 458.1[M+H]⁺.

Compound 3-6 was used as a common intermediate, the following compounds were obtained by the same synthesis and separation method as Compound 3-7 (i.e. replacing the carboxylic acid of compound 3-7 with the corresponding carboxylic acid in the following target molecules in the acid amine condensation reaction step),

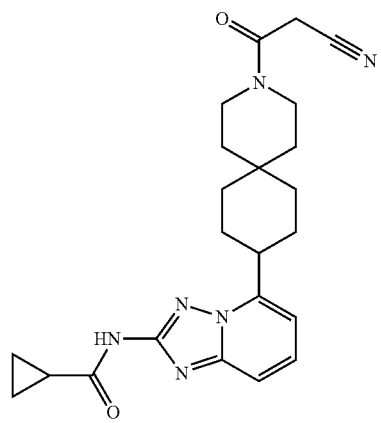

3-8

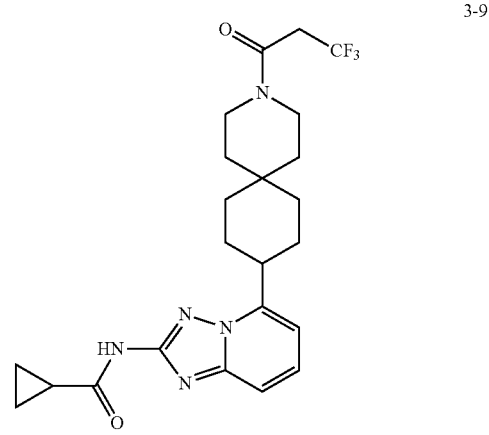

3-9

The characterization data are as follows:

Compound 3-8: ¹H NMR (400 MHz, METHANOL-d₄) δ7.57-7.67 (m, 1H), 7.49 (d, J=8.53 Hz, 1H), 7.03 (dd, J=3.76, 6.78 Hz, 1H), 4.61 (s, 1H), 3.83-3.91 (m, 1H), 3.62 (td, J=3.76, 7.53 Hz, 2H), 3.42-3.54 (m, 3H), 1.68-2.08 (m, 9H), 1.40-1.56 (m, 4H), 1.05 (quin, J=3.76 Hz, 2H), 0.88-0.97 (m, 2H). LCMS (ESI) m/z: 421.1[M+H]⁺.

Compound 3-9: ¹H NMR (400 MHz, METHANOL-d₄) δ 7.61 (dd, J=7.28, 8.78 Hz, 1H), 7.49 (d, J=8.78 Hz, 1H), 7.02 (dd, J=4.52, 6.78 Hz, 1H), 3.63 (td, J=3.83, 7.40 Hz, 2H), 3.43-3.58 (m, 5H), 1.67-2.07 (m, 9H), 1.39-1.54 (m, 4H), 1.01-1.08 (m, 2H), 0.93 (qd, J=3.68, 7.28 Hz, 2H). LCMS (ESI) m/z: 464.1[M+H]⁺.

Example 3

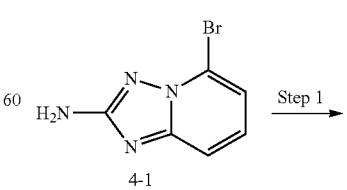

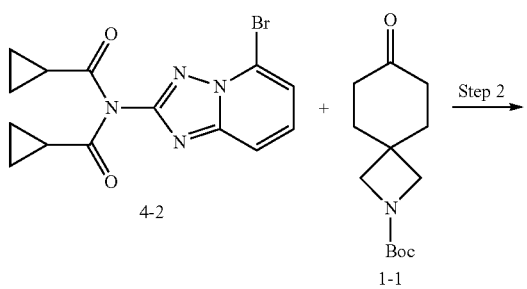

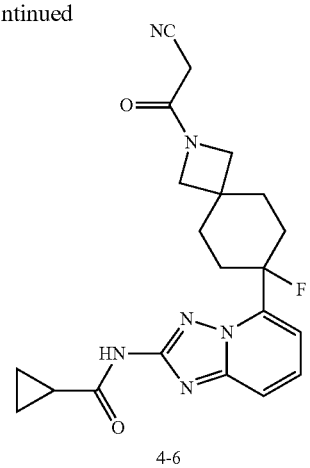

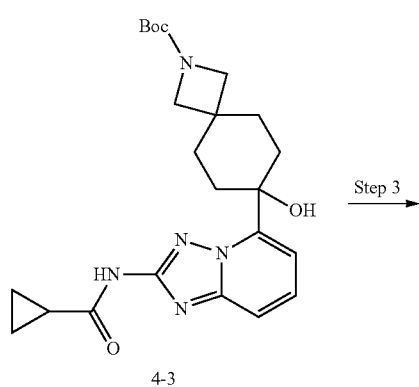

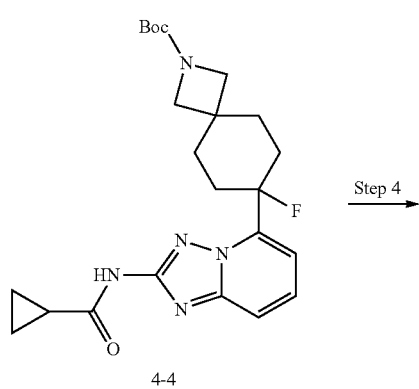

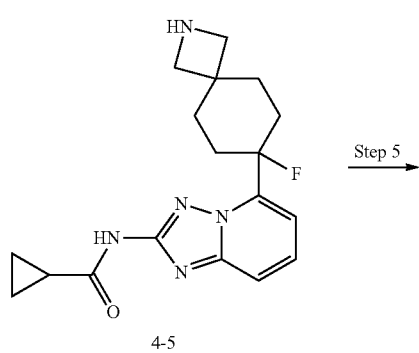

Step 1: 5-bromo-[1,2,4]triazole[1,5-a]pyridin-2-amino(4-1)(5 g, 23.5 mmol) was dissolved in acetonitrile (50 mL) at 0° C., triethylamine (11.87 g, 117.4 mmol) and cyclopropyl formyl chloride (6.13 g, 58.7 mmol) were added, and reaction solution reacted at 25° C. for 12 hours. TLC showed the reaction was complete. The acetonitrile was removed by vacuum concentration, and the residue was separated by rapid silica gel column (0-5% methanol/dichloromethane) to obtain Compound 4-2. LCMS (ESI) m/z: 350.8[M+H]$^+$.

Step 2: under the protection of $N_2$, Compound 4-2 (1.99 g, 5.7 mmol) and Compound 1-1 (1.5 g, 6.3 mmol) were dissolved in anhydrous tetrahydrofuran (30 mL), n-butyl lithium (2.5 m, 5.7 mL) solution was added at −70° C. slowly, and reaction solution was stirred at 10° C. for 30 minutes. LC-MS showed the reaction was complete. The reaction solution was quenched with saturated ammonium chloride (50 mL) at 0° C., and extracted with ethyl acetate (150 mL*2). The combined organic phases were washed with saturated salt water (10 mL), dried with anhydrous sodium sulfate, then filtered and concentrated under reduced pressure. The residue was separated by rapid silica gel column (0-3% methanol/dichloromethane) to obtain Compound 4-3. LCMS (ESI) m/z: 442.3[M+H]$^+$.

Step 3: Compound 4-3 (0.8 g, 1.81 mmol) was dissolved in anhydrous dichloromethane (10 mL) at 0° C., diethylamino sulfur trifluoride (DAST) (351 mg, 2.17 mmol) was added and reacted at 0° C. for 15 minutes, and then heated to 25° C. to react for 1 hour. LC-MS showed the reaction was complete. The reaction solution was quenched with saturated sodium bicarbonate aqueous solution (5 mL) at 0° C., diluted with water (10 mL), and extracted with dichloromethane (50 mL*3). The combined organic phases were washed with saturated salt water (20 mL), dried with anhydrous sodium sulfate, then filtered and concentrated under reduced pressure. The residue was separated by rapid silica gel column (0-100% ethyl acetate/petroleum ether) to obtain Compound 4-4. LCMS (ESI) m/z: 444.3[M+H]$^+$.

Step 4: Compound 4-4 (410 mg, 924.4 μmol) was dissolved in dichloromethane (5 mL), hydrochloric acid/ethyl acetate (4 M, 10 mL) was added, and reaction solution reacted at 20° C. for 30 minutes. LC-MS showed the reaction was complete. The solid was precipitated, filtered and dried to obtain Compound 4-5 (390 mg hydrochloride). LCMS (ESI) m/z: 344.2[M+H]$^+$.

Step 5: Compound 4-5 (130 mg, 342.2 μmol, hydrochloride) was dissolved in N,N-dimethylformamide (10 mL), HOBt (77 mg, 567.9 μmol) and EDCI (109 mg, 567.9 μmol)

were added, then 2-cyanoacetic acid (35 mg, 416.4 μmol) and diisopropyl ethylamine (98 mg, 757.1 μmol) were added, and reaction solution reacted at 15° C. for 12 hours. LC-MS showed the reaction was complete. The reaction solution was concentrated under reduced pressure and the residue was subjected to preparative HPLC (neutral condition) to obtain Compounds 4-6. $^1$H NMR (400 MHz, METHANOL-d$_4$) δ 7.66-7.72 (m, 1H), 7.56-7.62 (m, 1H), 7.25 (t, J=7.28 Hz, 1H), 4.29 (s, 1H), 4.03 (s, 1H), 3.97 (s, 1H), 3.76 (s, 1H), 3.26-3.30 (m, 2H), 2.97-3.28 (m, 2H), 1.74-2.08 (m, 7H), 0.89-1.13 (m, 4H). LCMS (ESI) m/z: 411.1[M+H]$^+$.

Compound 4-5 was used as the common intermediate, Compounds 4-7 and 4-8 were prepared by the same synthesis and separation method of acid amine condensation as Compound 4-6 (added with carboxylic acid compounds with different substitutions from Compound 4-6). The characterization data of compounds 4-7 and 4-8 are as follows:

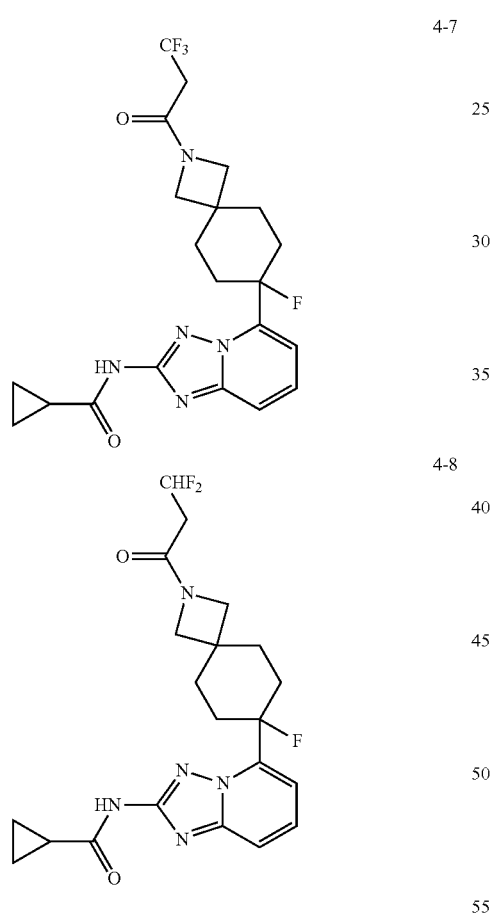

Compound 4-7: $^1$H NR (400 MHz, METHANOL-d$_4$) δ=7.65-7.73 (m, 1H), 7.59 (dt, J=1.13, 9.72 Hz, 1H), 7.20-7.29 (m, 1H), 4.33 (s, 1H), 4.01 (d, J=11.29 Hz, 2H), 3.76 (s, 1H), 2.99-3.30 (m, 4H), 1.74-2.10 (m, 7H), 0.88-1.12 (m, 4H). LCMS (ESI) m/z: 454.1[M+H]$^+$.

Compound 4-8: $^1$H NMR (400 MHz, METHANOL-d$_4$) δ=7.64-7.73 (m, 1H), 7.59 (dt, J=1.25, 9.16 Hz, 1H), 7.20-7.28 (m, 1H), 6.01-6.44 (m, 1H), 4.30 (s, 1H), 3.99 (d, J=11.80 Hz, 2H), 3.73 (s, 1H), 2.99-3.27 (m, 2H), 2.76-2.99 (m, 2H), 1.75-2.10 (m, 7H), 0.89-1.10 (m, 4H). LCMS (ESI) m/z: 436.1[M+H]$^+$.

Example 4

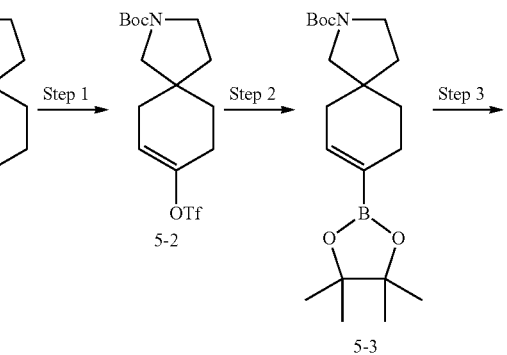

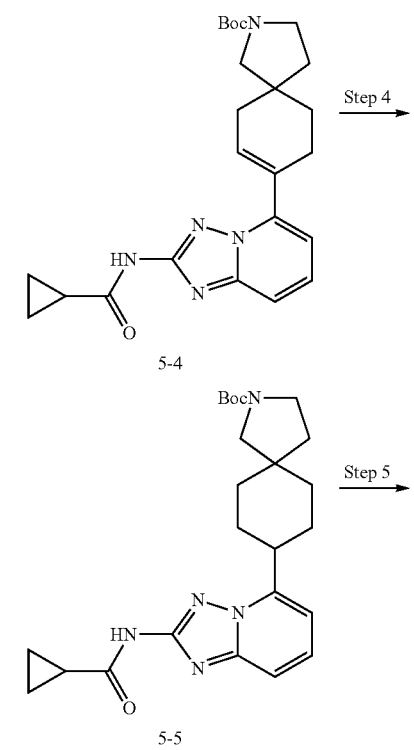

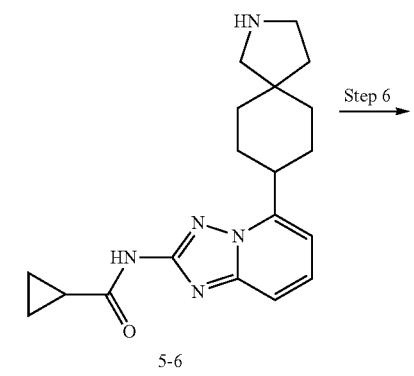

-continued

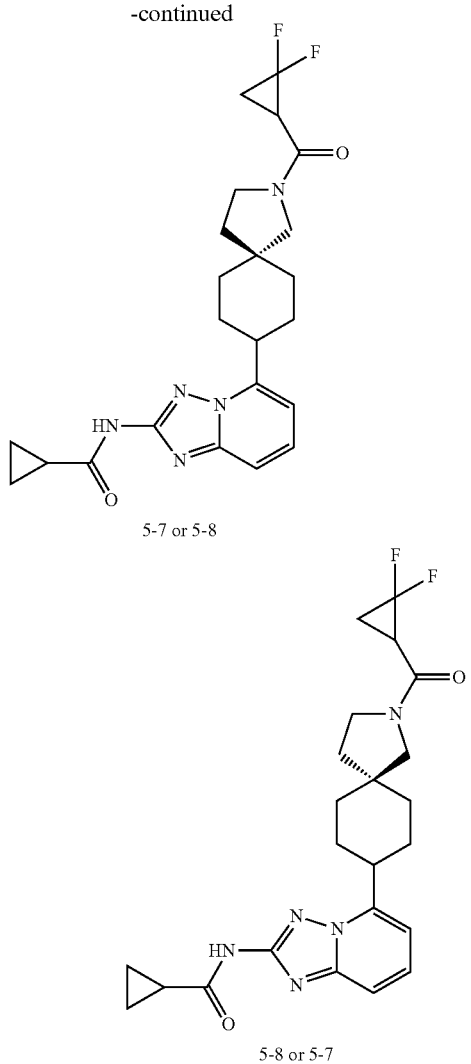

5-7 or 5-8

5-8 or 5-7

Step 1: THF (8 mL) solution of Compound 5-1 (0.15 g, 592.1 μmol) was dropped with LiHMDS (1 M, 770 μL) at −78° C. The mixture was stirred at −78° C. for 1 hour. The reaction solution was added with tetrahydrofuran (4 mL) solution of 1,1,1-trifluoro-N-phenyl-N-(trifluoromethylsulfonyl) methanesulfonamide (233 mg, 651 μmol) dropwise at −78° C. μmol) and stirred at 15° C. for 12 hours. TLC (PE:EA=5:1) showed that the reaction of raw materials was complete and new points were formed. The reaction was quenched with 10 mL of saturated ammonium chloride solution, then 20 mL of water was added, and extract with ethyl acetate (30 mL*3). The organic phases were combined and washed with saturated salt water (40 mL), dried with anhydrous sodium sulfate, then filtered and concentrated to obtain Compound 5-2, which was directly used in the next reaction without purification.

Step 2: DMF (10 mL) solution of Compound 5-2 (0.25 g, 648.7 μmol) and pinacol borate (165 mg, 648.7 μmol) was added with KOAc (191 mg, 2.0 mmol) and Pd (dppf)Cl$_2$ (48 mg, 64.9 μmol). The reaction solution was stirred at 70° C. for 12 hours. TLC (PE:EA=5:1) showed that the reaction of raw materials was complete, and new points were detected. The reaction solution was added with 20 mL of water and extracted with ethyl acetate (30 mL*3). The organic phases were combined, washed with saturated salt water (40 mL), dried with anhydrous sodium sulfate, filtered and concentrated to obtain a crude product, and then it was separated and purified by column chromatography (SiO$_2$, PE:EA=50: 0-20:1) to obtain colorless oily Compound 5-3. $^1$H NMR (400 MHz, METHANOL-d$_4$) δ6.50 (br s, 1H), 3.35-3.49 (m, 2H), 3.07-3.15 (m, 2H), 2.02-2.22 (m, 4H), 1.54-1.81 (m, 4H), 1.47 (s, 9H), 1.27 (s, 12H).

Step 3: Compound 5-3 (0.13 g, 357.8 μmol) was dissolved in dioxane (4 mL) and water (1 mL) solution, N-(5-bromo-[1,2,4]triazolo[1,5-a] pyridin-2-yl) cyclopropane formamide (101 mg, 357.8 μmol), K$_2$CO$_3$ (149 mg, 1.1 mmol), Pd(dppf)Cl$_2$ (26 mg, 35.8 μmol) were added, it was replaced with nitrogen for 3 times. The mixture was stirred at 90° C. for 12 hours in a nitrogen atmosphere. LCMS showed that the raw materials were consumed and a target molecular ion peak was monitored. The reaction solution was concentrated to remove the solvent, then dispersed in 10 mL of water and extracted with DCM/MeOH (10:1, 30 mL*3). The organic phases were combined, washed with saturated salt water (40 mL), dried with anhydrous sodium sulfate, and filtered, with the filtrate being distilled under reduced pressure. Compound 5-4 was purified by silica gel chromatography (SiO$_2$, DCM:MeOH=1:0 to 20:1). LCMS (ESI) m/z: 438.3[M+H]$^+$.

Step 4: methanol (10 mL) solution of Compound 5-4 (0.2 g, 457.1 μmol) was added with Pd/C (10%, 50 mg) in argon atmosphere. It was replaced with hydrogen 3 times and then stirred at 25° C. in hydrogen atmosphere (15 psi) for 2 hours. LCMS showed that the raw material was consumed and the target molecular ion peak was monitored. The reaction solution was filtered and concentrated to obtain Compound 5-5, which was directly used in the next step without purification. LCMS (ESI) m/z: 440.4[M+H]$^+$.

Step 5: Compound 5-5 (150 mg, 341.3 μmol) and trifluoroacetic acid (4 mL) were dissolved in dichloromethane (10 mL), it was replaced with nitrogen for 3 times, and then the reaction solution was stirred at 25° C. for 30 minutes. LCMS showed that the raw material was consumed and the target molecular ion peak was monitored. The reaction solution was concentrated to remove the solvent to obtain Compound 5-6 (0.15 g, trifluoroacetate), which was directly used in the next step without purification. LCMS (ESI) m/z: 340.2[M+H]$^+$.

Step 6: DMF (4 mL) solution of (1S)-2,2-difluorocyclopropyl formic acid (44 mg, 360.7 μmol) was added with EDCI (104 mg, 541.1 μmol), HOBt (73 mg, 541.1 μmol) and DIEA (140 mg, 1.1 mmol, 189 μL). It was stirred at 25° C. for 5 minutes, then Compound 5-6 (122 mg, 270 μmol, trifluoroacetate) was added, and it was stirred at 25° C. for 16 hours. LCMS showed that the raw materials were consumed and the target molecular ion peak was monitored. Crude product was obtained by preparative HPLC (neutral separation condition, chromatographic column: Waters XBridge 150 mm*25 mm 5 μm; Mobile phase: [H$_2$O (10 mM NH$_4$HCO$_3$)-ACN]; B (CH$_3$CN) %: 25%-55%, 7 min) and SFC chiral separation (chromatographic column: DAICEL CHIRALCEL OD-H (250 mm*30 mm, 5 μm); Mobile phase: [0.1% NH$_3$H$_2$O EtOH]; B (C$_{O2}$)%: 40%) to obtain Compound 5-7, SFC retention time: 3.685 min. $^1$H NMR (400 MHz, METHANOL-d$_4$) δ 7.48-7.55 (m, 1H), 7.39 (d, J=8.78 Hz, 1H), 6.92 (dd, J=6.90, 3.39 Hz, 1H), 3.35-3.76 (m, 5H), 2.66-2.94 (m, 1H), 1.51-2.10 (m, 13H), 0.94 (br s, 2H), 0.78-0.88 (m, 2H). LCMS (ESI) m/z: 444.1[M+H]$^+$. Compound 5-8, SFC retention time: 4.283 min. $^1$H NMR (400 MHz, METHANOL-d$_4$) δ 7.48-7.59 (m, 1H), 7.40 (br d, J=8.53 Hz, 1H), 6.94 (br d, J=6.78 Hz, 1H), 3.23-3.78 (m, 5H), 2.65-2.81 (m, 1H), 1.54-2.06 (m, 13H), 0.95 (br s, 2H), 0.77-0.87 (m, 2H). LCMS (ESI) m/z: 444.2[M+H]$^+$.

Compound 5-6 was used as a common intermediate, the following compounds were prepared by the same synthesis and separation method of acid amine condensation as Compound 5-7 (added with carboxylic acids different from Compound 5-7). The characterization data are as follows:

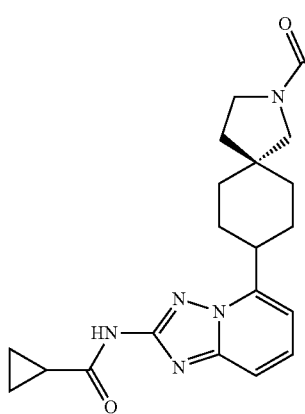

5-9

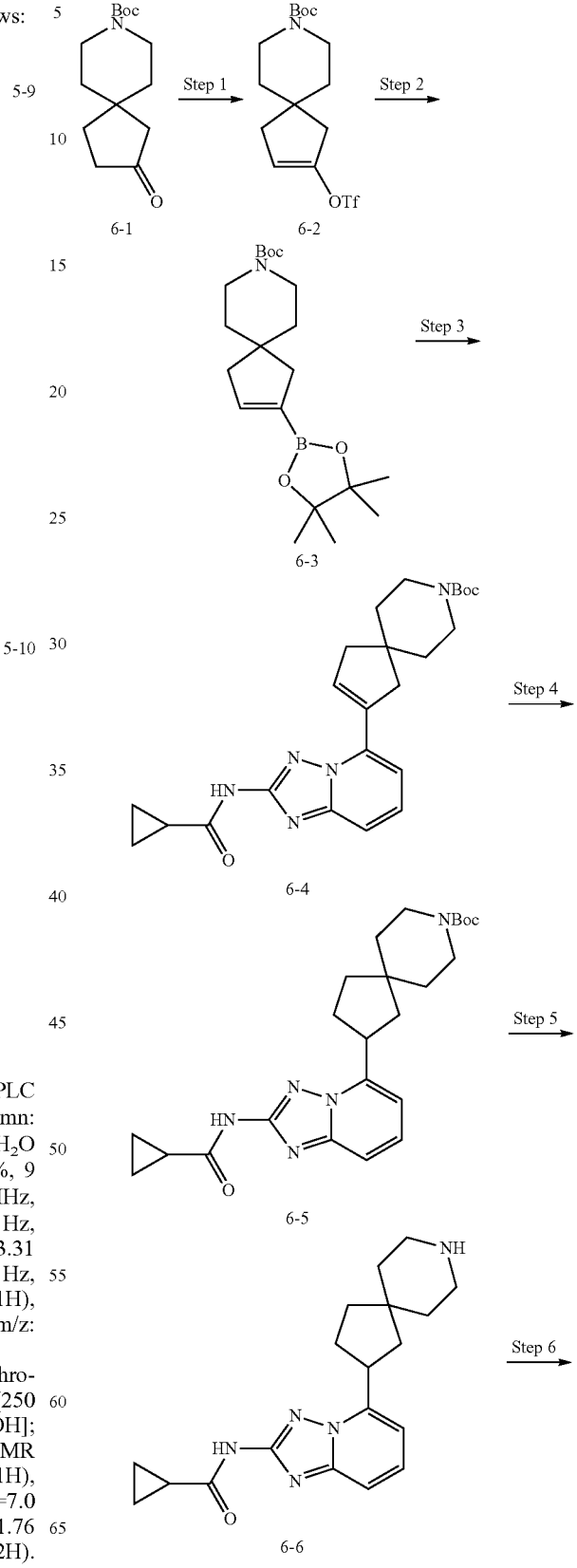

5-10

Compound 5-9: It was separated by preparative HPLC (neutral separation condition, chromatographic column: Waters XBridge 150 mm*25 mm 5 μm; Mobile phase: [H$_2$O (10 mM NH$_4$HCO$_3$)-ACN]; B (CH$_3$CN) %: 18%-32%, 9 min), retention time 2.117 min. $^1$H NMR (400 MHz, METHANOL-d$_4$) δ 7.60-7.68 (m, 1H), 7.52 (d, J=8.6 Hz, 1H), 7.05 (dd, J=3.4, 6.8 Hz, 1H), 3.44-3.73 (m, 4H), 3.31 (br s, 2H), 2.11 (td, J=7.6, 14.9 Hz, 3H), 2.01 (br t, J=7.3 Hz, 1H), 1.96 (br s, 1H), 1.66-1.88 (m, 6H), 1.31 (br s, 1H), 1.02-1.10 (m, 2H), 0.91-0.99 (m, 2H). LCMS (ESI) m/z: 407.2[M+H]$^+$.

Compound 5-10: SFC chiral separation conditions, chromatographic column: DAICEL CHIRALCEL OD-H (250 mm*30 mm, 5 μm); Mobile phase: [0.1% NH$_3$H$_2$O EtOH]; B(CO$_2$)%: 40%-40%, retention time 4.114 min. $^1$H NMR (400 MHz, METHANOL-d$_4$) δ=7.52 (br d, J=8.0 Hz, 1H), 7.40 (br d, J=8.8 Hz, 1H), 6.89-6.98 (m, 1H), 3.57 (t, J=7.0 Hz, 1H), 3.25-3.51 (m, 6H), 1.78-2.09 (m, 5H), 1.51-1.76 (m, 6H), 0.94 (br d, J=3.8 Hz, 2H), 0.79-0.88 (m, 2H). LCMS (ESI) m/z: 450.2[M+H]$^+$.

Example 5

-continued

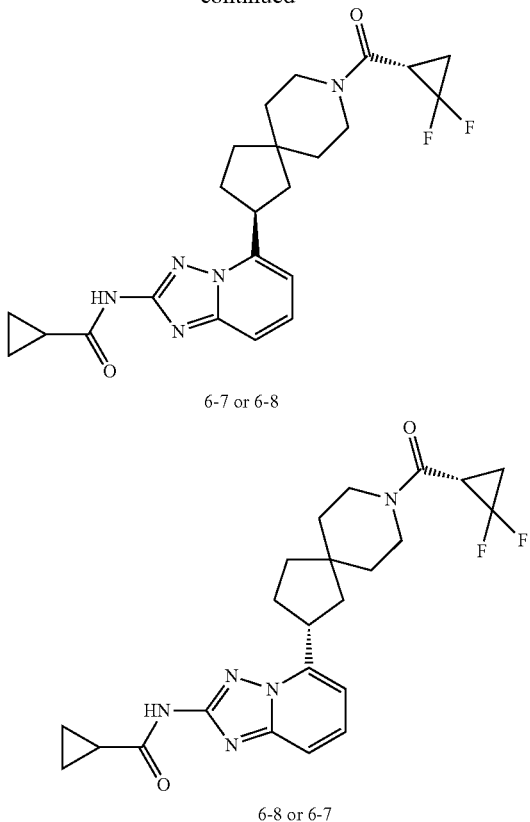

6-7 or 6-8

6-8 or 6-7

Step 1: THF (8 mL) solution of Compound 6-1 (250 mg, 986.8 μmol) was added with LiHMDS (1 M, 1.3 mL) dropwise. The mixture was stirred at −78° C. for 1 hour. The reaction solution was added with tetrahydrofuran (4 mL) solution of 1,1,1-trifluoro-N-phenyl-N-(trifluoromethylsulfonyl) methanesulfonamide (388 mg, 1.1 mmol) dropwise at −78° C., and then stirred at 25° C. for 12 hours. TLC (PE:EA=5:1) showed that the reaction of raw materials were complete and new points were formed. The reaction was quenched with 10 mL of saturated ammonium chloride solution, then 20 mL of water was added and extracted with ethyl acetate (30 mL*3). The organic phases were combined, washed with saturated salt water (40 mL), dried with anhydrous sodium sulfate, then filtered and concentrated to obtain the crude product, and it was separated and purified by column chromatography (SiO$_2$, PE:EA=20:1-10:1) to obtain Compound 6-2.

Step 2: DMF (5 mL) solution of Compound 6-2 (386 mg, 1.0 mmol) and pinacol borate (254 mg, 1.0 mmol) was added with KOAc (295 mg, 3.0 mmol) and Pd(dppf) Cl$_2$·CH$_2$Cl$_2$ (82 mg, 100 μmol). The reaction solution was stirred at 70° C. for 12 hours. TLC (PE:EA=5:1) showed that the reaction of raw material was complete, and new points were detected. The solution was added with 20 mL of water and extracted with ethyl acetate (30 mL*3). The organic phases were combined, washed with saturated salt water (40 mL), dried with anhydrous sodium sulfate, then filtered and concentrated to obtain the crude product, and then separated and purified by column chromatography (SiO$_2$, PE:EA=50: 0-20:1) to obtain Compound 6-3.

Step 3: Compound 6-3 (186 mg, 512 μmol) was dissolved in dioxane (4 mL) and water (1 mL) solution, N-(5-bromo-[1,2,4]triazolo[1,5-a]pyridin-2-yl) cyclopropane formamide (144 mg, 512 μmol), K$_2$CO$_3$ (212 mg, 1.5 mmol), and Pd(dppf)Cl$_2$·CH$_2$Cl$_2$ (42 mg, 51.2 μmol) were added, it was replaced with nitrogen for 3 times. The mixture was stirred at 90° C. for 12 hours in nitrogen atmosphere. LCMS showed that the raw materials were consumed and the target molecular ion peak was monitored. The reaction solution was concentrated to remove the solvent, then dispersed in 10 mL of water and extracted with DCM:MeOH (10:1, 30 mL*3). The organic phases were combined, washed with saturated salt water (40 mL), dried with anhydrous sodium sulfate, and filtered. The filtrate was distilled under reduced pressure to obtain a crude product, which was purified by silica gel chromatography (SiO$_2$, DCM:MeOH=1:0-20:1) to obtain Compound 6-4. LCMS (ESI) m/z: 438.7[M+H]$^+$.

Step 4: Methanol (10 mL) solution of Compound 6-4 (196 mg, 448 μmol) was added with Pd/C (10%, 50 mg). It was replaced with hydrogen for three times and stirred for 16 hours at 25° C. in a hydrogen atmosphere (15 psi). LCMS showed that the raw materials were consumed and the target molecular ion peak was monitored. The reaction solution was filtered and concentrated to obtain Compound 6-5, which was directly used in the next step without purification. LCMS (ESI) m/z: 440.3[M+H]$^+$.

Step 5: Compound 6-5 (130 mg, 296 μmol) and trifluoroacetic acid (4 mL) were dissolved in dichloromethane (10 mL) solution, it was replaced with nitrogen for three times, and then the reaction solution was stirred at 25° C. for 30 minutes. LCMS showed that the raw materials were consumed and the target molecular ion peak was monitored. The reaction solution was concentrated to remove the solvent to obtain Compound 6-6 (134 mg, trifluoroacetate), which was directly used in the next step reaction without purification. LCMS (ESI) m/z: 340.2[M+H]$^+$.

Step 6: DMF (4 mL) solution of (1S)-2,2-difluorocyclopropyl formic acid (36 mg, 295.5 μmol) was added with EDCI (85 mg, 443.3 μmol), HOBt (60 mg, 443.3 μmol), and DIEA (115 mg, 886.5 μmol, 154.4 μL), it was stirred at 25° C. for 5 minutes, then Compound 6-6 (134 mg, 295.5 μmol, trifluoroacetate) was added, and the mixture was stirred at 25° C. for 16 hours. LCMS showed that the raw materials were consumed and the target molecular ion peak was monitored. Crude product was subjected to preparative separation (neutral condition. Waters Xbridge 150*25 5 μm; Mobile phase: [water (10 mM NH$_4$HCO$_3$)-ACN];B %: 30%-50%, 7 min) and SFC chiral separation (chromatographic column: YMC CHIRAL Amylose-C (250 mm*30 mm, 10 μm; Mobile phase: [0.1% NH$_3$H$_2$O EtOH];B %: 50%). Compound 6-7 was obtained. SFC retention time: 2.339 min. $^1$H NMR (400 MHz, DMSO-d$_6$) δ 11.01 (br s, 1H), 7.51-7.63 (m, 2H), 7.08 (br d, J=6.78 Hz, 1H), 3.83 (br s, 1H), 3.41-3.66 (m, 4H), 3.15 (br d, J=5.02 Hz, 1H), 2.14-2.35 (m, 2H), 2.06 (br s, 1H), 1.75-1.95 (m, 4H), 1.40-1.73 (m, 6H), 0.84 (br s, 4H). LCMS (ESI) m/z: 444.1[M+H]$^+$. Compound 6-8: SFC retention time: 4.142 min. $^1$H NMR (400 MHz, DMSO-d$_6$) δ 11.01 (br s, 1H), 7.54-7.65 (m, 2H), 7.08 (br s, 1H), 3.80-3.90 (m, 1H), 3.45-3.66 (m, 4H), 3.09-3.22 (m, 1H), 2.18-2.36 (m, 2H), 2.06 (br s, 1H), 1.75-1.95 (m, 4H), 1.68 (br d, J=7.28 Hz, 3H), 1.50 (br d, J=4.77 Hz, 3H), 0.77-0.88 (m, 4H). LCMS (ESI) m/z: 444.1[M+H]$^+$.

Example 6

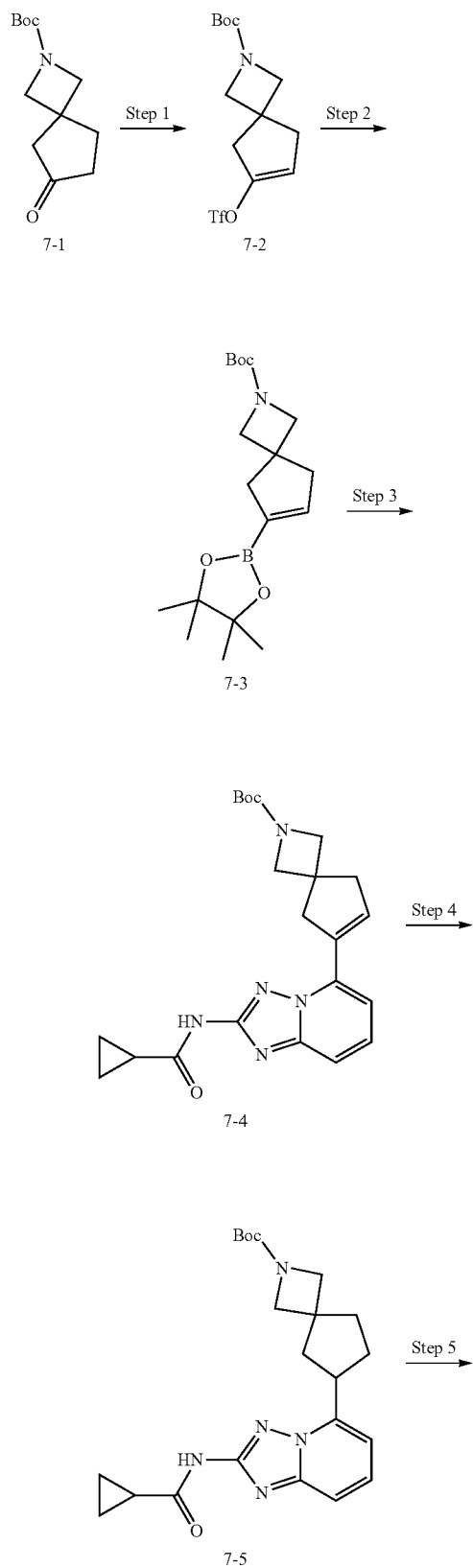

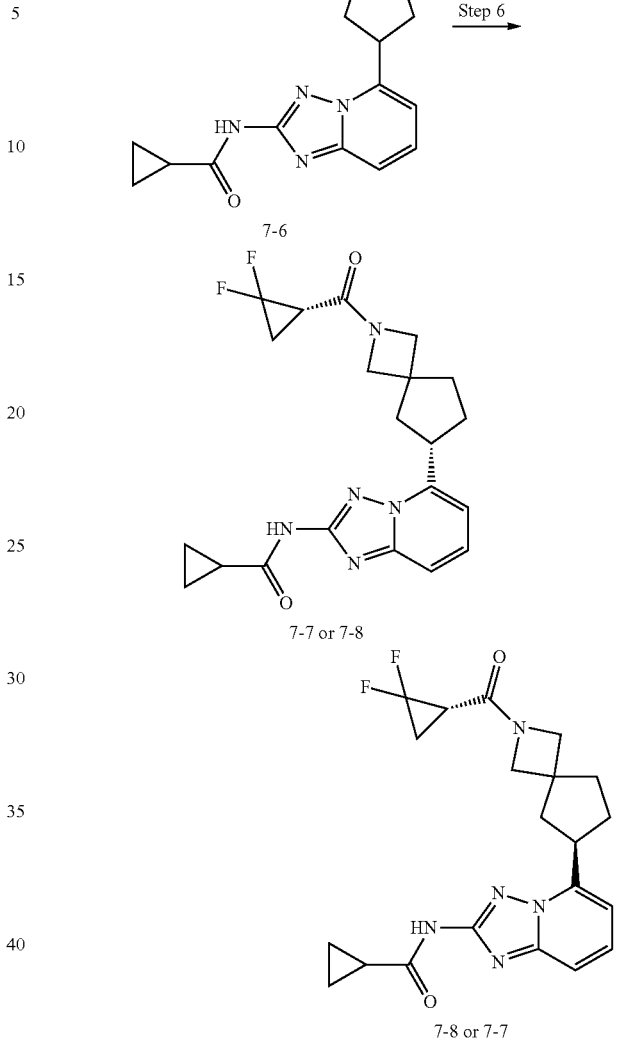

Step 1: THF (8 mL) solution of Compound 7-1 (0.3 g, 1.33 mmol) was added with LiHMDS (1 M, 1.7 mL) dropwise at −78° C. The mixture was stirred at −78° C. for 1 hour, tetrahydrofuran (4 mL) solution of 1,1,1-trifluoro-N-phenyl-N-(trifluoromethylsulfonyl) methanesulfonamide (523 mg, 1.46 mmol) was added dropwise, and then the mixture was stirred at 25° C. for 12 hours. TLC (PE:EA=5:1) showed that the reaction of raw materials was complete and new points were formed. The reaction solution was quenched with saturated ammonium chloride (10 mL) solution, then 20 mL of water was added and it was extracted with ethyl acetate (30 mL*3). The organic phases were combined, washed with saturated salt water (40 mL), dried with anhydrous sodium sulfate, filtered and concentrated to obtain the crude product, and then separated and purified by column chromatography (SiO$_2$, PE:EA=20:1-10:1) to obtain Compound 7-2. $^1$H NMR (400 MHz, CDCl$_3$) δ 5.72 (s, 1H), 3.86-3.92 (m, 2H), 3.76-3.82 (m, 2H), 2.53-2.61 (m, 2H), 2.18-2.25 (m, 2H), 1.37 (s, 9H).

Step 2: DMF (5 mL) solution of Compound 7-2 (0.46 g, 1.3 mmol) and pinacol borate (327 mg, 1.3 mmol) was added with KOAc (379 mg, 3.9 mmol) and Pd(dppf)

Cl$_2$·CH$_2$Cl$_2$ (105 mg, 128.7 µmol). The reaction solution was stirred at 70° C. for 12 hours. TLC (PE:EA=5:1) showed that the reaction of raw materials was complete, and new points were detected. The reaction solution was quenched with 20 mL of water and extracted with ethyl acetate (30 mL*3). The organic phases were combined, washed with saturated salt water (40 mL), dried with anhydrous sodium sulfate, filtered and concentrated to obtain the crude product, and then it was separated and purified by column chromatography (SiO$_2$, PE:EA=50:0-20:1) to obtain Compound 7-3. $^1$H NMR (400 MHz, CDCl$_3$) δ 6.45 (t, J=1.88 Hz, 1H), 3.83-3.88 (m, 2H), 3.73-3.78 (m, 2H), 2.36-2.42 (m, 2H), 2.04 (t, J=7.03 Hz, 2H), 1.37 (s, 9H), 1.21 (s, 12H).

Step 3: Compound 7-3 (0.15 g, 447.43 µmol) was dissolved in dioxane (4 mL) and water (1 mL) solution, N-(5-bromo-[1,2,4]triazolo[1,5-a] pyridin-2-yl) cyclopropane formamide (126 mg, 447.43 µmol), K$_2$CO$_3$ (186 mg, 1.34 mmol), and Pd(dppf)Cl$_2$·CH$_2$Cl$_2$ (37 mg, 44.7 µmol) were added, it was replaced with nitrogen for 3 times. The mixture was stirred at 90° C. for 12 hours in a nitrogen atmosphere. LCMS showed that the raw materials were completely consumed and the target molecular ion peak was monitored. The reaction solution was concentrated to remove the solvent, then dispersed in 10 mL of water and extracted with DCM:MeOH (10:1, 30 mL*3). The organic phases were combined, washed with saturated salt water (40 mL), dried with anhydrous sodium sulfate, and filtered. The filtrate was distilled under reduced pressure to obtain a crude product. The crude product was purified by silica gel chromatography (SiO$_2$, DCM:MeOH=1:0-20:1) to obtain Compound 7-4. LCMS (ESI) m/z: 410.2[M+H]$^+$.

Step 4: Methanol (10 mL) solution of Compound 7-4 (0.15 g, 366.3 µmol) was added with Pd/C (10%, 0.05 g). The mixture was replaced with hydrogen for three times and stirred in a hydrogen atmosphere (15 psi) at 25° C. for 16 hours. LCMS showed that the raw materials were completely consumed and the target molecular ion peak was monitored. The reaction solution was filtered and concentrated to obtain Compound 7-5, which was directly used in the next step without purification. LCMS (ESI) m/z: 412.2 [M+H]$^+$.

Step 5: Compound 7-5 (0.13 g, 315.9 µmol) and trifluoroacetic acid (4 mL) were dissolved in dichloromethane (10 mL) solution, it was replaced with nitrogen for three times, and then the reaction solution was stirred at 25° C. for 30 minutes. LCMS showed that the raw materials were completely consumed and the target molecular ion peak was monitored. The reaction solution was concentrated to remove the solvent to obtain Compound 7-6 (130 mg, trifluoroacetate), which was directly used in the next step without purification. LCMS (ESI) m/z: 312.1[M+H]$^+$.

Step 6: DMF (4 mL) solution of (1S)-2,2-difluorocyclopropyl formic acid (37 mg, 305.6 µmol) was added with EDCI (88 mg, 458.4 µmol), HOBt (62 mg, 458.4 µmol), DIEA (119 mg, 916.8 µmol, 160 µL). The mixture was stirred at 25° C. for 5 minutes, then Compound 7-6 (0.13 g, 305.6 µmol, trifluoroacetate) was added, and it was stirred at 25° C. for 16 hours. LCMS showed that the raw materials were completely consumed and the target molecular ion peak was monitored. The crude product was subjected to preparative HPLC separation (chromatographic column: Waters Xbridge 150*25 5 µm; Mobile phase: [H$_2$O (10 mM NH$_4$HCO$_3$)-ACN]; B (CH$_3$CN) %: 20%-50%, 7 min) and chiral separation (chromatographic column: DAICEL CHIRALPAK AD (250 mm*30 mm, 10 µm; Mobile phase, A % (0.1% NH$_3$H$_2$O EtOH); B(CO$_2$)%: (40%-40%) to obtain Compound 7-7, SFC retention time: 3.714 min. $^1$H NMR (400 MHz, CDCl$_3$) δ=9.59 (br d, J=12.05 Hz, 1H), 7.34-7.57 (m, 2H), 6.70-6.84 (m, 1H), 4.06-4.21 (m, 2H), 3.92-3.99 (m, 1H), 3.74-3.92 (m, 2H), 1.81-2.38 (m, 8H), 1.59 (dtd, J=11.36, 7.62, 7.62, 3.76 Hz, 1H), 1.08-1.24 (m, 2H), 0.79-0.96 (m, 2H). LCMS (ESI) m/z: 416.0[M+H]$^+$.

Compounds 7-8 was isolated and the SFC retention time was 4.468 min. $^1$H NMR (400 MHz, CDCl$_3$) δ=9.48 (br s, 1H), 7.34-7.54 (m, 2H), 6.76 (br d, J=7.03 Hz, 1H), 4.03-4.25 (m, 2H), 3.73-3.99 (m, 3H), 2.50 (ddd, J=16.81, 13.18, 8.16 Hz, 1H), 1.80-2.40 (m, 8H), 1.53-1.66 (m, 1H), 1.05-1.23 (m, 2H), 0.80-0.95 (m, 2H). LCMS (ESI) m/z: 416.0 [M+H]$^+$.

Example 7

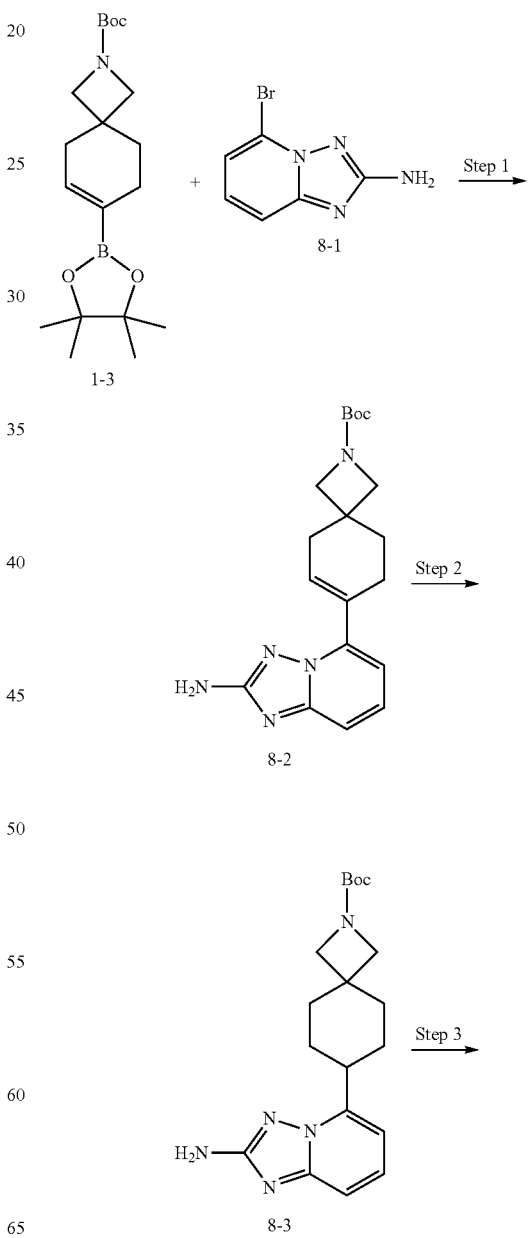

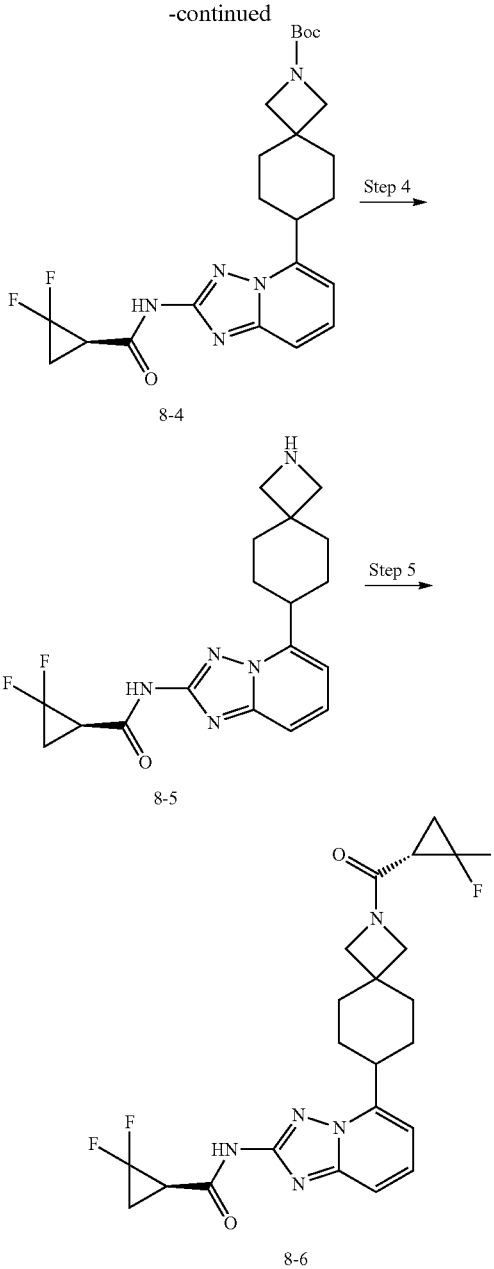

8-4

8-5

8-6

Step 1: under the protection of nitrogen Compound 8-1 (1.11 g 5.6 mmol) and Compound 1-3 were dissolved in dioxane (40 mL) and water (10 mL) solution, potassium carbonate (2.16 g, 15.6 mmol) and [1,1-bis(diphenylphosphine) ferrocene]palladium dichloride dichloromethane (425 mg, 520.6 mol) were added, it was replaced with nitrogen for 3 times, and reaction solution was heated to 90° C. for 3 hours. LC-MS showed the reaction was complete. The reaction solution was concentrated under reduced pressure, and the residue was subjected to rapid silica gel column separation (0~4% methanol/dichloromethane) to obtain Compound 8-2. LCMS (ESI) m/z: 356.3[M+H]⁺.

Step 2: under the protection of nitrogen, Compound 8-2 (2 g, 5.6 mmol) was dissolved in methanol (100 mL) solution, catalyst dry palladium/carbon (0.5 g, 10%) was added, and it was replaced with hydrogen for 3 times. Under hydrogen pressure (30 psi) and reaction temperature of 30° C., the reaction solution was stirred for 12 hours. LC-MS showed that 50% of raw materials were remained. The catalyst was filtered out and replaced with new catalyst dry palladium/carbon (1 g). The reaction continued for 3 hours, and LCMS showed that the reaction was complete. The solid was filtered by diatomite and the filtrate was concentrated under reduced pressure to obtain Compound 8-3. LCMS (ESI) m/z: 358.2[M+H]⁺.

Step 3: (1R)-2,2-difluorocyclopropyl carboxylic acid (282 mg, 2.3 mmol) was dissolved in pyridine (10 mL), EDCI (4.0 g, 21.0 mmol) and Compound 8-3 (0.75 g, 2.1 mmol) were added, and reaction solution was stirred at 10° C. for 12 hours. LC-MS showed the reaction was complete. The reaction solution was diluted with water (30 mL), extracted with dichloromethane/methanol (10/1, 50 mL*3), washed with saturated salt water (30 mL), dried with anhydrous sodium sulfate, filtered and concentrated under reduced pressure. The residue was subjected to rapid silica gel column separation (0-3% methanol/dichloromethane), and then purified by beating with ethyl acetate to obtain Compound 8-4. LCMS (ESI) m/z: 462.3[M+H]⁺.

Step 4: Compound 8-4 (300 mg, 650.1 μmol) was dissolved in dichloromethane (5 mL), hydrochloric acid/ethyl acetate (4 M, 10 mL) was added, and reacted at 15° C. for half an hour. LC-MS showed the reaction was complete. The reaction solution was concentrated to obtain Compound 8-5 (hydrochloride). LCMS (ESI) m/z: 362.2[M+H]⁺.

Step 5: Compound 8-5 (100 mg, 251.4 μmol, HCl) was dissolved in N,N-dimethylformamide (5 mL), HOBt (51 mg, 377.0), EDCI (72.28 mg, 377.0 μmol), (1S)-2,2-difluorocyclopropyl carboxylic acid (34 mg, 276.5 μmol) and diisopropyl ethylamine (65 mg, 502.7 μmol) were added, and reaction solution reacted at 15° C. for 12 hours. LC-MS showed the reaction was complete. The reaction solution was concentrated under reduced pressure and the residue was subjected to preparative HPLC (neutral condition) to obtain Compound 8-6. ¹H NMR (400 MHz, METHANOL-d₄) δ7.59-7.67 (m, 1H), 7.51 (d, J=8.78 Hz, 1H), 7.01 (br d, J=7.53 Hz, 1H), 3.92-4.20 (m, 2H), 3.79-3.88 (m, 1H), 3.67-3.77 (m, 1H), 3.43-3.57 (m, 1H), 2.81 (br s, 1H), 2.62 (dq, J=7.78, 11.96 Hz, 1H), 2.07-2.24 (m, 5H), 1.52-2.05 (m, 7H). LCMS (ESI) m/z: 466.2[M+H]⁺.

Compound 8-5 was used as a common intermediate, Compounds 8-7 and 8-8 were prepared by the same synthesis and separation method as Compound 8-6 by acid amine condensation (added with carboxylic acids substituted differently from Compound 8-6). The characterization data of Compounds 8-7 and 8-8 are as follows:

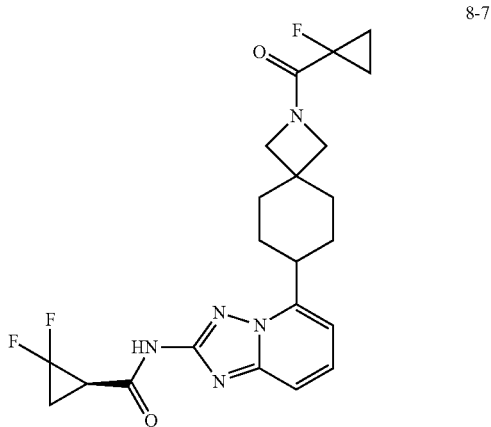

8-7

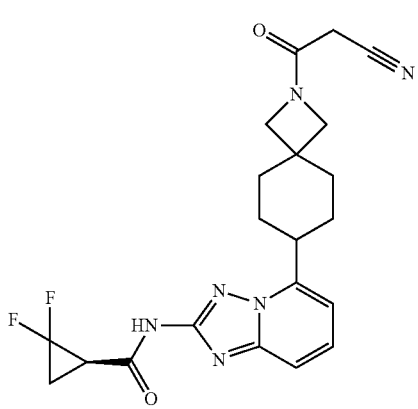

8-8

Compounds 8-7, crude product was purified by preparative HPLC (neutral condition). ¹H NMR (400 MHz, METHANOL-$d_4$) δ 7.59-7.66 (m, 1H), 7.51 (d, J=8.78 Hz, 1H), 6.97-7.04 (m, 1H), 4.30 (d, J=4.27 Hz, 1H), 4.18 (d, J=4.27 Hz, 1H), 3.87 (s, 1H), 3.76 (s, 1H), 3.49 (br t, J=11.80 Hz, 1H), 2.81 (br s, 1H), 2.05-2.28 (m, 5H), 1.74-1.96 (m, 3H), 1.53-1.70 (m, 2H), 1.23-1.33 (m, 4H). LCMS (ESI) m/z: 448.2[M+H]⁺.

Compounds 8-8, crude product was purified by preparative HPLC (neutral condition). ¹H NMR (400 MHz, METHANOL-$d_4$) δ7.59-7.67 (m, 1H), 7.51 (d, J=8.78 Hz, 1H), 7.00 (t, J=7.40 Hz, 1H), 4.61 (s, 2H), 3.69-4.11 (m, 4H), 3.41-3.54 (m, 1H), 2.82 (br s, 1H), 2.04-2.26 (m, 5H), 1.72-1.93 (m, 3H), 1.61 (q, J=11.80 Hz, 2H). LCMS (ESI) m/z: 429.0[M+H]⁺.

8-9

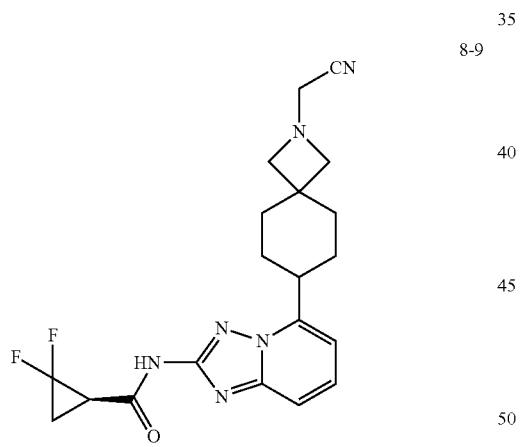

Synthesis of compound 8-9: intermediate 8-5 (100 mg, 227.6 μmol, TFA) was dissolved in N,N-dimethylformamide (5 mL), potassium carbonate (94 mg, 682.7 μmol) and 2-bromoacetonitrile (30 mg, 250.3 μmol) were added, and it was stirred at 10° C. for 12 hours. LC-MS showed the reaction was complete. The reaction solution was diluted with water (5 mL), and extracted with dichloromethane/methanol (10/1, 10 mL). The organic phase was washed with saturated salt water (10 mL), dried with anhydrous sodium sulfate, filtered and concentrated under reduced pressure. The residue was purified by preparative HPLC (neutral condition) to obtain Compound 8-9. ¹H NMR (400 MHz, METHANOL-$d_4$) δ 7.59-7.66 (m, 1H), 7.50 (d, J=8.78 Hz, 1H), 6.99 (d, J=7.53 Hz, 1H), 3.62 (s, 2H), 3.46 (br t, J=12.05 Hz, 1H), 3.33 (s, 2H), 3.21 (s, 2H), 2.80 (br s, 1H), 2.14 (br d, J=9.79 Hz, 5H), 1.82-1.95 (m, 1H), 1.52-1.77 (m, 4H). LCMS (ESI) m/z: 401.0[M+H]⁺.

Example 8

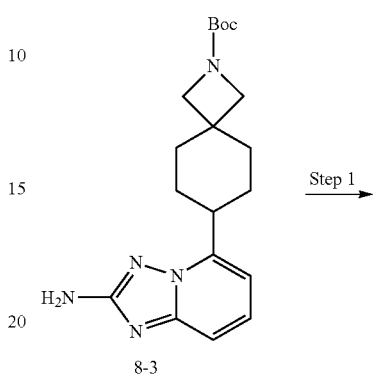

Step 1

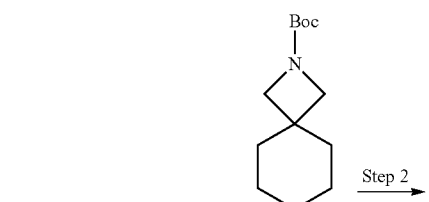

Step 2

9-1

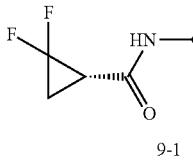

Step 3

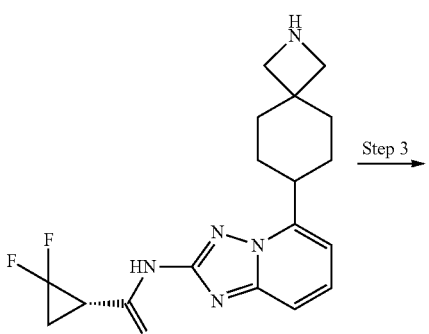

9-2

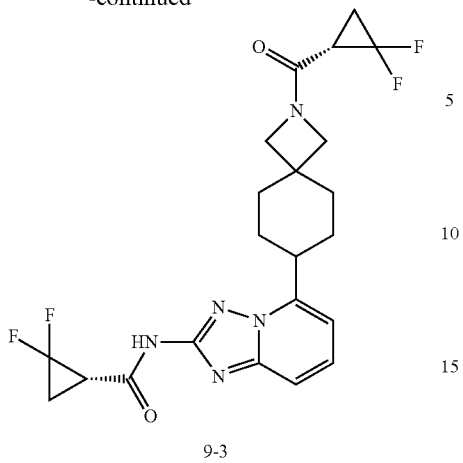

9-3

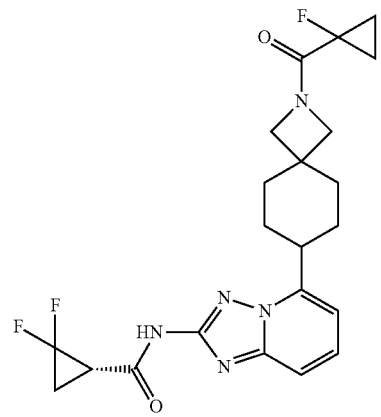

9-4

Step 1: (S)-2,2-difluorocyclopropyl carboxylic acid (1.13 g, 9.2 mmol) was dissolved in pyridine (150 mL), EDCI (16.1 g, 84 mmol) and Compound 8-3 (3 G, 8.4 mmol) were added, and reaction solution was stirred at 10° C. for 12 hours. LC-MS showed the reaction was complete. The reaction solution was diluted with water (100 mL), extracted with dichloromethane/methanol (10/1, 100 mL*3), washed with saturated salt water (30 mL), dried with anhydrous sodium sulfate, filtered and concentrated under reduced pressure. The residue was subjected to rapid silica gel column separation (0-3% methanol/dichloromethane), and then purified by beating with ethyl acetate to obtain Compound 9-1. LCMS (ESI) m/z: 462.3[M+H]$^+$.

Step 2: Compound 9-1 (2.3 g, 4.9 mmol) was dissolved in dichloromethane (5 mL), hydrochloric acid/ethyl acetate (4 M, 20 mL) was added, and it was stirred at 15° C. for half an hour. LC-MS showed that the reaction was complete and the target molecular ion peak was detected. The precipitated solid was filtered and dried to obtain Compound 9-2 (hydrochloride). LCMS (ESI) m/z: 362.2[M+H]$^+$.

Step 3: Compound 9-2 (1.23 g, 3.1 mmol, HCl) was dissolved in N,N-dimethylformamide (20 mL), HOBt (626 mg, 4.6 mmol) and EDCI (889 mg, 4.6 mmol) were added, then (1S)-2,2-difluorocyclopropyl carboxylic acid (414.92 mg, 3.40 mmol) and diisopropyl ethylamine (798.70 mg, 6.18 mmol) were added. The reaction solution was stirred at 15° C. for 12 hours. LC-MS showed the reaction was complete. The reaction solution was diluted with water (10 mL), and extracted with dichloromethane/methanol (10/1, 50 mL). The organic phase was washed with saturated salt water (10 mL), dried with anhydrous sodium sulfate, filtered and concentrated under reduced pressure. The residue was subjected to preparative HPLC (neutral condition) to obtain Compound 9-3. $^1$H NMR (400 MHz, METHANOL-d$_4$) δ 7.63 (dd, J=7.53, 8.78 Hz, 1H), 7.51 (d, J=8.78 Hz, 1H), 7.01 (br d, J=7.28 Hz, 1H), 3.92-4.19 (m, 2H), 3.79-3.87 (m, 1H), 3.67-3.76 (m, 1H), 3.44-3.55 (m, 1H), 2.52-2.92 (m, 2H), 1.53-2.25 (m, 12H). LCMS (ESI) m/z: 466.1[M+H]$^+$.

Compound 9-2 was used as a common intermediate, Compounds 9-4 and 9-5 were prepared by the same synthesis and separation method as Compound 9-3 by acid amine condensation (added with carboxylic acids substituted differently from Compound 9-3). The characterization data are as follows:

Compound 9-4: $^1$H NMR (400 MHz, METHANOL-d$_4$) δ 7.58-7.68 (m, 1H), 7.51 (d, J=8.78 Hz, 1H), 6.97-7.05 (m, 1H), 4.30 (d, J=4.02 Hz, 1H), 4.18 (d, J=4.27 Hz, 1H), 3.87 (s, 1H), 3.76 (s, 1H), 3.49 (br t, J=11.80 Hz, 1H), 2.82 (br s, 1H), 2.07-2.25 (m, 5H), 1.73-1.95 (m, 3H), 1.51-1.70 (m, 2H), 1.24-1.35 (m, 4H). LCMS (ESI) m/z: 448.2[M+H]$^+$.

Compound 9-5: $^1$H NMR (400 MHz, METHANOL-d$_4$) δ 7.58-7.68 (m, 1H), 7.51 (d, J=9.03 Hz, 1H), 7.00 (t, J=7.53 Hz, 1H), 4.61 (s, 2H), 3.69-4.10 (m, 4H), 3.43-3.55 (m, 1H), 2.82 (br s, 1H), 2.05-2.25 (m, 5H), 1.72-1.97 (m, 3H), 1.51-1.69 (m, 2H). LCMS (ESI) m/z: 429.0[M+H]$^+$.

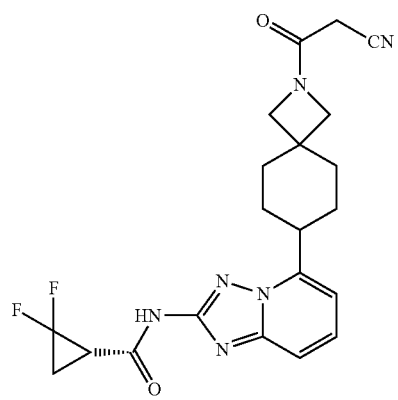

9-5

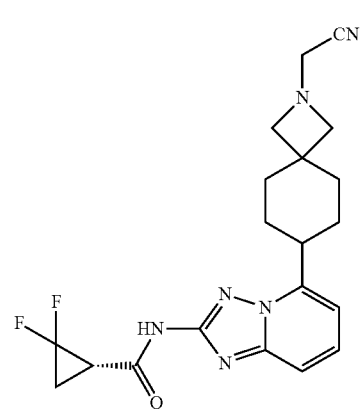

9-6

Synthesis of compound 9-6: compound 9-2 (190 mg, 525.8 μmol) was dissolved in N,N-dimethylformamide (5 mL), potassium carbonate (218 mg, 1.6 mmol) and 2-bromoacetonitrile (70 mg, 578.3 µmol) were added, and reaction solution was stirred at 10° C. for 12 hours. LC-MS showed the reaction was complete. The reaction solution was diluted with water (5 mL), and extracted with dichloromethane/methanol (10/1, 10 mL). The organic phase was washed with saturated salt water (10 mL), dried with anhydrous sodium sulfate, filtered and concentrated under reduced pressure. The residue was purified by preparative HPLC (neutral condition) to obtain compounds 9-6. $^1$H NMR (400 MHz, METHANOL-d$_4$) δ7.58-7.66 (m, 1H), 7.50 (d, J=8.53 Hz, 1H), 6.99 (d, J=7.28 Hz, 1H), 3.62 (s, 2H), 3.46 (br t, J=11.42 Hz, 1H), 3.33 (s, 2H), 3.21 (s, 2H), 2.81 (br s, 1H), 2.14 (br d, J=10.29 Hz, 5H), 1.81-1.95 (m, 1H), 1.51-1.78 (m, 4H). LCMS (ESI) m/z: 401.2[M+H]$^+$.

Example 9

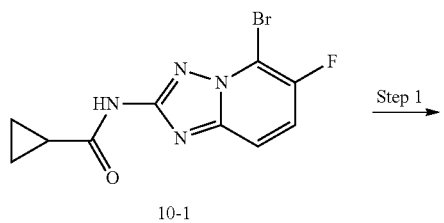

10-1

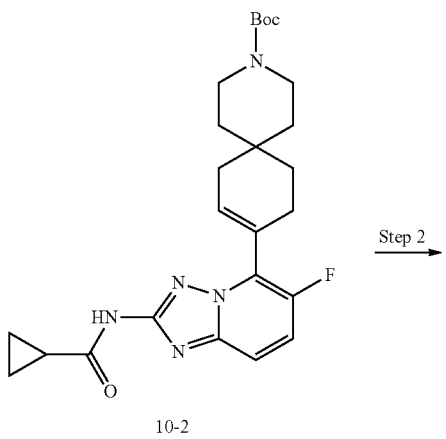

10-2

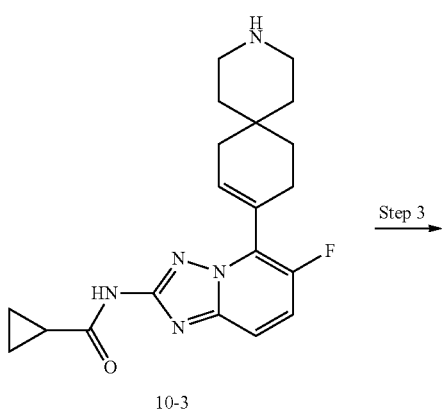

10-3

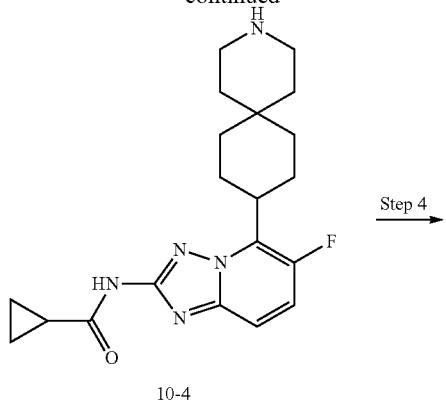

10-4

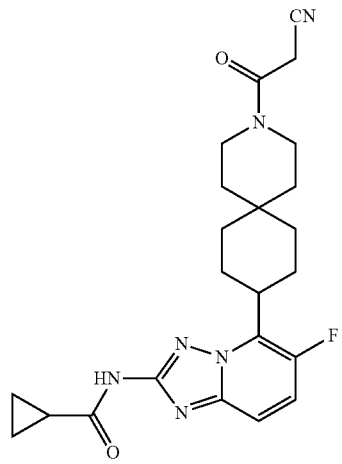

10-5

Step 1: Compound 10-1 (100 mg, 334.3 µmol), Compound 3-3 (126 mg, 334.3 µmol), Pd(dppf)Cl$_2$ (25 mg, 33.4 µmol) and potassium carbonate (139 mg, 1.00 mmol) were added into the mixed solution of dioxane (12 mL) and H$_2$O (3 mL). It was replaced with nitrogen for 3 times. The reaction solution was stirred in nitrogen atmosphere at 90° C. for 2 hours. LCMS shows that the raw materials were consumed, and the main peak was the target molecular ion peak. The reaction solution was filtered and concentrated to remove the solvent, and then subjected to preparation plate separation and purification to obtain Compound 10-2. LCMS (ESI) m/z: 470.4[M+H]$^+$.

Step 2: Dichloromethane (1 mL) solution of Compound 10-2 (130 mg, 276.9 µmol) and HCL/EtOAc (4 M, 2 mL) was stirred at 25° C. for 5 minutes. LCMS showed that the raw materials were consumed, and the main peak was the target molecular ion peak. The reaction solution was concentrated under reduced pressure to obtain yellow solid Compound 10-3 (120 mg, hydrochloride), which was directly used in the next step without purification. LCMS (ESI) m/z: 370.6[M+H]$^+$.

Step 3: under nitrogen atmosphere, MeOH (25 mL) solution of Compound 10-3 (120 mg, 295.6 µmol, hydrochloride) was added with Pd/C (20 mg, 10%). The suspension was replaced with hydrogen for 3 times, and then stirred in hydrogen atmosphere (15 Psi) at 25° C. for 12 hours. LCMS showed that the raw materials were consumed, and the main peak was the target molecular ion peak. The reaction solution was filtered and concentrated under reduced pressure to remove the solvent to obtain Compound 10-4 (130 mg, hydrochloride), which was directly used in the next step of the reaction without further purification. LCMS (ESI) m/z: 372.3[M+H]$^+$.

Step 4: Compound 10-4 (130 mg, 318.7 µmol, hydrochloride) was dissolved in DMF (5 mL) solution, 2-cyanoacetic acid (33 mg, 382.4 µmol), EDCI (92 mg, 478 µmol), HOBt (65 mg, 478 µmol) and DIEA (206 mg, 1.6 mmol, 277.6 µL) were added, the mixture was stirred at 25° C. for 12 hours. LCMS showed that the raw materials were consumed and the target molecular ion peak was monitored. The reaction solution was concentrated under reduced pressure to remove the solvent, and then subjected to preparative separation to obtain (neutral system) Compound 10-5. $^1$H NMR (400 MHz, METHANOL-d$_4$) δ=7.57-7.65 (m, 1H), 7.49-7.55 (m, 1H), 3.59-3.81 (m, 3H), 3.44-3.54 (m, 2H), 3.34-3.38 (m, 2H), 2.48 (br s, 2H), 1.81-2.04 (m, 5H), 1.64-1.77 (m, 2H), 1.36-1.58 (m, 4H), 0.86-1.12 (m, 4H). LCMS (ESI) m/z: 439.1 [M+H]$^+$.

Biological Activity Test

Experimental Example 1: In Vitro Activity Test of JAK1, JAK2, JAK3 and TYK2 Kinases Experimental Materials Recombinant human JAK1, JAK2, JAK3, TyK2 protease, main instruments and reagents were provided by Eurofins in the UK Experimental Method Diluting JAK2, JAK3 and TYK2: 20 mM 3-(N-morpholine) propanesulfonic acid (MOPS), 1 mM EDTA, 0.01% Brij-35.5% glycerol, 0.1% β-mercaptoethanol, 1 mg/mL BSA; JAK1 dilution: 20 mM Tris, 0.2 mM EDTA, 0.1% β-mercaptoethanol, and 0.01% Brij-35.5% glycerol. All compounds were prepared into a 100% DMSO solution and reached 50 times the final determined concentration. The test compound was diluted by 3 times the concentration gradient, and the final concentration was 10 µM to 0.001 µM, 9 concentrations in total, and the content of DMSO in the detection reaction was 2%. The working stock solution of the compound was added to a determination hole as the first component of the reaction, and then the remaining components were added according to the detailed scheme determination below.

JAK1 (h) Enzyme Reaction

JAK1 (h) was incubated with 20 mm Tris/HCl pH7.5, 0.2 mM EDTA, 500 µM MGEEPLYWSFPAKKK, 10 mm magnesium acetate and [γ-$^{33}$P]-ATP (activity and concentration as required) together. Mg/ATP mixture was added to start the reaction. After incubation at room temperature for 40 minutes, 0.5% phosphoric acid was added to stop the reaction. Then 10 µL of the reactant was placed on a P30 filter pad, washed three times with 0.425% phosphoric acid and once with methanol within 4 minutes, dried and counted by scintillation.

JAK2 (h) Enzyme Reaction

JAK2 (h) was incubated with 8 mM MOPS pH 7.0, 0.2 mM EDTA, 100 µM KTFCGTPEYLAPEVRREPRILSEE-EQEMFRDFDYIADWC, 10 mM magnesium acetate and [γ-$^{33}$P]-ATP (activity and concentration as required) together. Mg/ATP mixture was added to start the reaction. After incubation at room temperature for 40 minutes, 0.5% phosphoric acid was added to stop the reaction. Then add 10 µL of the reactant point was placed on the P30 filter pad, washed three times with 0.425% phosphoric acid and once with methanol within 4 minutes, dried and counted by scintillation.

JAK3 (h) Enzyme Reaction

JAK3 (h) was incubated with 8 mM MOPS pH 7.0, 0.2 mM EDTA, 500 µM GGEEEEYFELVKKKK, 10 mM magnesium acetate and [γ-$^{33}$P]-ATP (activity and concentration as required) together. Mg/ATP mixture was added to start the reaction. After incubation at room temperature for 40 minutes, 0.5% phosphoric acid was added to stop the reaction. Then 10 µL of the reactant point was placed on the P30 filter pad, washed three times with 0.425% phosphoric acid and once with methanol within 4 minutes, dried and counted by scintillation.

TYK2 (h) Enzyme Reaction

TYK2 (h) was incubated with 8 mM MOPS pH 7.0, 0.2 mM EDTA, 250 µM GGMEDIYFEFMGGKKK, 10 mM magnesium acetate and [γ-$^{33}$P]-ATP (activity and concentration as required) together. Mg/ATP mixture was added to start the reaction. After incubation at room temperature for 40 minutes, 0.5% phosphoric acid was added to stop the reaction. Then 10 µL of the reactant point was placed on the P30 filter pad, washed three times with 0.425% phosphoric acid and once with methanol within 4 minutes, dried and counted by scintillation.

Data Analysis $IC_{50}$ results were obtained by analysis using XLFIT5 (Formula 205) of IDBS company. See Table 1 for details.

TABLE 1 in vitro screening test results of compounds of the present invention

| Compounds | TYK2 ($IC_{50}$, nM) | JAK1 ($IC_{50}$, nM) | JAK2 ($IC_{50}$, nM) | JAK3 ($IC_{50}$, nM) |
|---|---|---|---|---|
| 1-7 | 38 | 6 | 60 | 3834 |
| 1-8 | 27 | 14 | 78 | 2939 |
| 1-9 | 366 | 34 | 315 | >10000 |
| 1-10 | 311 | 32 | 426 | >10000 |
| 1-11 | 18 | 15 | 198 | >10000 |
| 1-12 | 360 | 45 | 527 | >10000 |
| 1-13 | 36 | 3 | 37 | 1517 |
| 1-14 | 134 | 12 | 144 | 5035 |
| 1-15 | 106 | 20 | 208 | 9669 |
| 1-16 | 581 | 114 | 1020 | >10000 |
| 1-17 | 371 | 65 | 791 | >10000 |
| 3-7 | 26 | 3 | 40 | 1002 |
| 3-8 | 26 | 20 | 80 | 2323 |
| 3-9 | 155 | 54 | 294 | >10000 |
| 4-6 | 307 | 170 | 2008 | 8448 |
| 4-7 | 194 | 436 | 7685 | >10000 |
| 4-8 | >10000 | 244 | 3711 | 364 |
| 5-7 | 67 | 31 | 324 | 5759 |
| 5-8 | 692 | 75 | 789 | 7349 |
| 5-9 | 278 | 68 | 520 | >10000 |
| 5-10 | 1526 | 131 | 2730 | >10000 |
| 6-7 | 829 | 63 | 998 | 9391 |
| 6-8 | 570 | 381 | 1924 | >10000 |
| 7-7 | 830 | 63 | 1632 | >10000 |
| 7-8 | 404 | 176 | 2313 | >10000 |
| 8-6 | 127 | 14 | 110 | 7637 |
| 8-7 | 1032 | 63 | 5463 | >10000 |
| 8-8 | 109 | 60 | 1376 | >10000 |
| 8-9 | 1329 | 52 | 3672 | >10000 |
| 9-3 | 105 | 7 | 292 | >10000 |
| 9-4 | 1186 | 253 | 982 | >10000 |
| 9-5 | 175 | 224 | 624 | >10000 |
| 9-6 | 1388 | 432 | 1174 | >10000 |
| 10-5 | 430 | 336 | 812 | 5410 |

Conclusion: the compounds of the present invention shows good selective inhibition to Jak1 and/or TYK2 in in vitro activity test of four kinase subtypes JAK1, JAK2, JAK3 and TYK2.

Experimental Example 2: Pharmacokinetic (PK) Test

A clear solution obtained by dissolving test compounds was administered into male mice ($C_{57}BL/6$) or rats (SD) via tail vein and oral administration (overnight fasting, 7-8 weeks old). After administration of the test compounds, blood was collected from mandibular vein and centrifuged to obtain plasma, at 0.117, 0.333, 1, 2, 4, 7 and 24 hours for the tail vein injection group (2 mg/kg) and 0.25, 0.5, 1, 2, 4, 8 and 24 hours for the oral administration group (15 mg/kg). The blood drug concentration was determined by LC-MS/MS, and WinNonlin™ Version 6.3 pharmacokinetic software was used to calculate relevant pharmacokinetic parameters by non atrioventricular model linear logarithmic ladder method. The test results are as follows:

TABLE 2-1

PK test results of Compounds 1-11 in mice

| PK parameters | Results |
| --- | --- |
| $T_{1/2}$ (hr) | 2.99 |
| $C_{max}$ (nM) | 5745 |
| $AUC_{0-inf}$ (nM · hr) | 9918 |
| Bioavailability (%)$^a$ | 42.1% |

TABLE 2-2

PK test results of Compounds 1-13 in mice

| PK parameters | Results |
| --- | --- |
| $T_{1/2}$ (hr) | 1.61 |
| $C_{max}$ (nM) | 5105 |
| $AUC_{0-inf}$ (nM · hr) | 9917 |
| Bioavailability (%)$^a$ | 38.1% |

TABLE 2-3

PK test results of Compounds 3-7 in mice

| PK parameters | Results |
| --- | --- |
| $T_{1/2}$ (h) | 4.74 |
| $C_{max}$ (nM) | 7380 |
| $AUC_{0-inf}$ (nM · h) | 17969 |
| Bioavailability (%)$^a$ | 50.1% |

Note: $T_{1/2}$: half life: $C_{max}$: peak concentration;

$AUC_{0-inf}$: area under the plasma concentration time curve extrapolated from time 0 to infinity;

Bioavailability: bioavailability.

Conclusion: the compounds of the present invention have good oral bioavailability and high exposure in mice, which is conducive to producing good in vivo drug efficacy.

Experimental Example 3: In Vivo Pharmacodynamic Study of the Compounds on Inflammatory Bowel Disease (IBD)

Experiment Purpose:

Inflammatory bowl disease (IBD) is a kind of recurrent disease. It is difficult to cure, has a high recurrence rate, and has a poor prognosis, it has a certain correlation with the incidence of colon cancer. The development of drugs for the treatment of IBD will help alleviate the symptoms of ulcerative colitis and Crohn's disease and improve the quality of life of patients. The mouse inflammation model induced by dextran sulfate sodium (DSS) is similar to the human disease ulcerative colitis and Crohn's disease. It is a common classical model for preclinical evaluation of drug efficacy. The purpose of this experiment is to investigate the therapeutic effects of compounds 1-8, 1-11, 9-3 and 1-13 on DSS induced ulcerative colitis and Crohn's disease in mice, and to provide preclinical pharmacodynamic information for clinical research.

Test Method:

1. Preparation of Modeling Solution and Drugs for Intragastric Administration

Preparation method of DSS: 20 g DSS was weighed, 1000 mL drinking water was added to form 2% DSS solution, and stored in a 4° C. refrigerator. It is effective within one month.

Preparation method of a solvent: Vehicle solution is an aqueous solution containing 0.5% methylcellulose and 0.5% Tween 80. Firstly, 5 g of methylcellulose was dissolved in 990 mL of pure water, then 5 g of Tween 80 was added in small amount for many times, mixed evenly and stored at room temperature.

Preparation method of compounds: the compound was weighed, an aqueous solution with a mass ratio of 0.5% methylcellulose+0.5% Tween 80 was added, and it was processed by ultrasonic until it was dissolved. After the solution is fully mixed, it was loaded into glass bottles and stored in a 4° C. refrigerator.

2. Induction of IBD and Administration

Seventy male C57BL/6 mice were weighed and randomly divided into 7 groups with mice in each group. The grouping and dose design are shown in Table 3-1.

The adaptation period of the animals was 3 days. After adaptation, the animals were weighed every day. The blank group was given drinking water, and the other groups were given drinking water containing 2% DSS. The water volume was 5 mL/animal/day. The animals in the test drug group were administrated by gavage once a day. The blank group and DNCB group were given the same volume of vehicle, with the administration volume of 10 mL/kg. Every other day, the fecal viscosity was evaluated, feces were collected for fecal occult blood detection, and the disease activity index (DAI) score was calculated. DSS consumption was detected every day. Fresh DSS solution was replaced every two days. The dosing cycle was continuous intragastric administration for 7 days, followed by 4 days of drug withdrawal, followed by 7 days of continuous intragastric administration. Normal drinking water was changed when intragastric administration was stopped.

TABLE 3-1

Grouping and dose design

| Groups | Name of drugs to be tested | Number | Route of administration | Concentration mg/mL | Dosage mg/kg | Frequency of administration |
|---|---|---|---|---|---|---|
| Blank | Blank (solvent control group) | 10 | p.o. | N/A | N/A | qd, 14 days |
| DSS | Blank (solvent control group) | 10 | p.o. | N/A | N/A | qd, 14 days |
| DSS + 001 | Compounds 1-8 | 10 | p.o. | 1.5 | 15 | qd, 14 days |
| DSS + 002 | Compounds 1-11 | 10 | p.o. | 1.5 | 15 | qd, 14 days |
| DSS + 003 | Compounds 9-3 | 10 | p.o. | 1.5 | 15 | qd, 14 days |
| DSS + 004 | Compounds 1-13 | 10 | p.o. | 1.5 | 15 | qd, 14 days |
| DSS + 005 | Filgotinib | 10 | p.o. | 3.0 | 30 | qd, 14 days |

Note:
P.O.: oral;
dq: once a day.

3. IBD Disease Severity Test

DAI is the sum of the scores of body weight, fecal viscosity and fecal occult blood. The scoring criteria are shown in Table 3-2. Among them, the semi quantitative detection method of piramine cave was adopted for detecting fecal occult blood, including adding piramine cave to the sample first, then adding hydrogen peroxide and ethanol solution, and reading and scoring the color within 2 min. Immediately generating purple blue is marked as 4+, generating the purple blue within 10 s is marked as 3+, generating purple red within 1 min is marked as 2+, and gradually generating the purple red within 1-2 min is marked as 1+, and generating no color reaction of purple orchid or purple red within the reading time is recorded as negative (−). After the experiment, the colon and spleen were taken, and the length of colon and the weight of spleen were measured. The spleen index was the ratio of spleen weight to body weight.

TABLE 3-2

DAI scoring standard

| Scores | Weight loss | Fecal viscosity | Occult blood |
|---|---|---|---|
| 0 | <1% | Normal | — |
| 1 | 1-5% | Soft but shaped stool | 1+ |
| 2 | 6-10% | Soft and unshaped stool | 2+ |
| 3 | 11-18% | Wet stool | 3+ |
| 4 | >18% | Watery stool | 4+ |

4. Statistical Processing

The experimental data were expressed by means±standard error (Mean±SEM), and all data were statistically analyzed by one-way ANOVA, with $P<0.05$ as the statistical difference.

Experimental Results:

1. DAI Score

From the DAI score results, as shown in Table 3-3 and FIG. 1, the DAI score of DSS group increased rapidly after 4 days of administration. Compared with the blank control group, the DAI score of DSS group increased significantly on the 6th day and continued until the end of the experiment. No significant difference was found between each administration group and DSS group within 1 week of administration. Compared with before and after drug withdrawal (i.e. day 8 and day 12), the DAI of all DSS drinking water groups decreased significantly. After administration on the 12th day, the scores of Compounds 1-8, 1-13 and Filgotinib DAI began to decrease, and there were significant differences between the DSS group and the DSS group on day 16 and day 18. At the same time, on day 16 and day 18, the DAI score of Compounds 1-13 was significantly lower than that of the positive drug Filgotinib, indicating that Compounds 1-13 has a better effect on reducing DAI score than the positive drug Filgotinib, suggesting that Compounds 1-13 may have a better therapeutic effect on IBD.

TABLE 3-3

DAI scores of the present application

| Days | Blank | DSS | DSS + 001 | DSS + 002 | DSS + 003 | DSS + 004 | DSS + 005 |
|---|---|---|---|---|---|---|---|
| 2 | 0.89 ± 0.49 | 0.60 ± 0.27 | 0.90 ± 0.28 | 0.30 ± 0.15 | 0.40 ± 0.16 | 0.60 ± 0.38 | 1.20 ± 0.42 |
| 4 | 0.78 ± 0.34 | 1.10 ± 0.23 | 1.70 ± 0.42 | 1.50 ± 0.34 | 1.70 ± 0.54 | 1.50 ± 0.31 | 2.20 ± 0.61 |
| 6 | 0.89 ± 0.33 | 3.10 ± 0.60 # | 4.40 ± 0.33 | 3.50 ± 0.27 | 2.40 ± 0.37 | 2.50 ± 0.73 | 2.90 ± 0.43 |
| 8 | 0.56 ± 0.23 | 5.60 ± 0.58 ## | 4.44 ± 0.57 | 4.20 ± 0.79 | 4.70 ± 0.94 | 5.00 ± 0.69 | 6.40 ± 0.69 |
| 12 | 0.00 ± 0.00 | 2.78 ± 0.49 ## | 2.75 ± 0.50 | 3.11 ± 0.49 | 4.11 ± 0.53 | 2.43 ± 0.31 | 3.56 ± 0.82 |
| 14 | 0.22 ± 0.14 | 3.44 ± 0.51 ## | 2.63 ± 0.83 | 3.22 ± 0.79 | 4.88 ± 0.44 | 2.07 ± 0.31 | 3.00 ± 0.57 |
| 16 | 0.22 ± 0.14 | 5.78 ± 0.60 ## | 2.25 ± 0.58 ** | 4.44 ± 0.67 | 3.67 ± 0.86 * | 1.58 ± 0.44 **α | 3.00 ± 0.96 ** |
| 18 | 0.11 ± 0.10 | 6.75 ± 0.51 ## | 2.57 ± 0.51 ** | 5.89 ± 0.51 | 4.83 ± 0.68 | 1.05 ± 0.56 **αα | 3.52 ± 0.73 ** |

Figure 2:
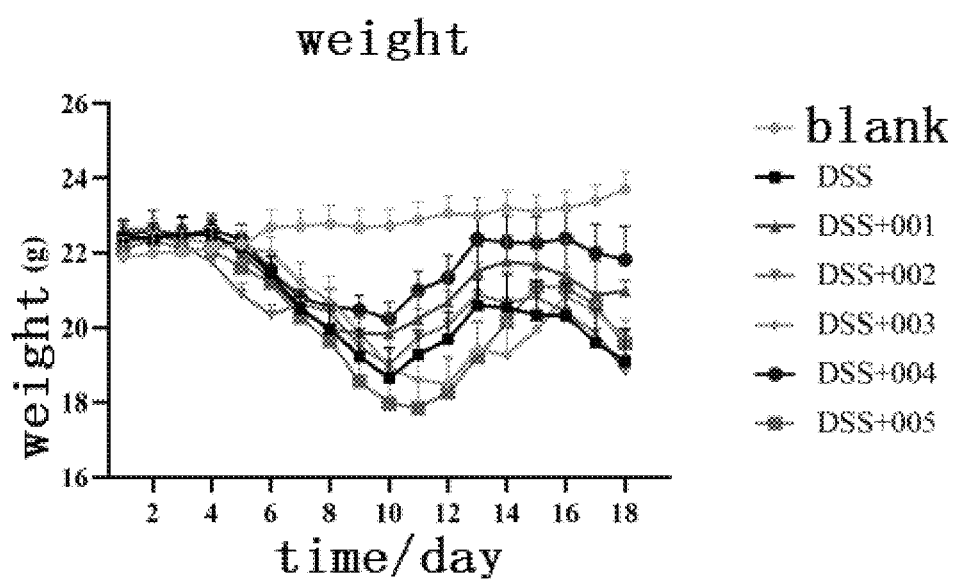
FIG. 2: curve diagram of weight change results of mice in experimental example 3.

Note:
compared with the blank group, # $P < 0.05$, ## $P < 0.01$;
compared with DSS group,
* $p < 0.05$,
** $p < 0.01$;
and compared with DSS + 005 group α $p < 0.05$ αα $p < 0.01$ 2. Weight The experimental results are shown in Table 3-4 and FIG. 2. From day 5, the weight of mice in the DSS group began to decrease. Compared with the blank control group, the weight of mice in the DSS group began to decrease on day 5, and there was a significant difference on day 7 and lasted until the end of the experiment. Compared with DSS group, Compounds 1-8 and 1-13 can reduce the weight loss caused by DSS. Compounds 1-13 showed significant difference on day 11, day 15, day 16 and day 18, while Compounds 1-8 had no significant difference. Compared with the positive drug Filgotinib, Compound 1-13 can reduce the weight loss of mice caused by DSS and significantly increase on day 9, day 10, day 14 and day 18, indicating that Compounds 1-13 had a better effect on reducing the weight loss of mice caused by DSS, suggesting that Compounds 1-13 may have a better therapeutic effect on IBD.

TABLE 3-4

Weight of mice in the invention

| Days | Blank | DSS | DSS + 001 | DSS + 002 | DSS + 003 | DSS + 004 | DSS + 005 |
|---|---|---|---|---|---|---|---|
| 1 | 21.87 ± 0.55 | 22.43 ± 0.43 | 22.30 ± 0.30 | 22.63 ± 0.29 | 22.26 ± 0.29 | 22.46 ± 0.40 | 22.10 ± 0.42 |
| 2 | 22.00 ± 0.55 | 22.40 ± 0.39 | 22.43 ± 0.25 | 22.64 ± 0.28 | 22.48 ± 0.29 | 22.60 ± 0.54 | 22.35 ± 0.41 |
| 3 | 22.03 ± 0.58 | 22.54 ± 0.41 | 22.43 ± 0.31 | 22.20 ± 0.28 | 22.39 ± 0.27 | 22.48 ± 0.51 | 22.11 ± 0.31 |
| 4 | 22.12 ± 0.58 | 22.48 ± 0.38 | 22.56 ± 0.37 | 21.75 ± 0.25 | 22.26 ± 0.31 | 22.63 ± 0.41 | 22.07 ± 0.38 |
| 5 | 22.23 ± 0.50 | 22.15 ± 0.35 | 21.99 ± 0.49 | 20.90 ± 0.30 | 22.18 ± 0.40 | 22.38 ± 0.38 | 21.61 ± 0.47 |
| 6 | 22.69 ± 0.46 | 21.47 ± 0.45 | 21.29 ± 0.60 | 20.33 ± 0.28 | 22.00 ± 0.43 | 21.54 ± 0.51 | 21.21 ± 0.55 |
| 7 | 22.71 ± 0.45 | 20.50 ± 0.52 ## | 20.48 ± 0.47 | 20.64 ± 0.38 | 21.21 ± 0.53 | 21.18 ± 0.53 | 20.28 ± 0.47 |
| 8 | 22.77 ± 0.49 | 19.97 ± 0.63 ## | 19.96 ± 0.51 | 20.44 ± 0.58 | 20.72 ± 0.67 | 20.56 ± 0.49 | 19.65 ± 0.47 |
| 9 | 22.68 ± 0.50 | 19.24 ± 0.72 ## | 19.85 ± 0.47 | 19.49 ± 0.77 | 19.89 ± 0.37 | 20.78 ± 0.39α | 18.57 ± 0.49 |
| 10 | 22.72 ± 0.46 | 18.66 ± 0.80 ## | 19.84 ± 0.50 | 19.00 ± 0.87 | 18.92 ± 0.47 | 20.24 ± 0.45α | 17.98 ± 0.62 |
| 11 | 22.87 ± 0.50 | 19.28 ± 0.66 ## | 20.23 ± 0.67 | 19.73 ± 0.77 | 18.60 ± 0.62 | 21.86 ± 0.50 * | 17.85 ± 0.80 |
| 12 | 23.06 ± 0.47 | 19.70 ± 0.71 ## | 20.69 ± 0.77 | 20.09 ± 0.90 | 18.50 ± 0.74 | 21.34 ± 0.60 | 18.27 ± 0.91 |
| 13 | 23.00 ± 0.49 | 20.59 ± 0.71 # | 21.51 ± 0.67 | 20.88 ± 0.86 | 19.42 ± 0.78 | 22.38 ± 0.69 | 19.21 ± 0.94 |
| 14 | 23.19 ± 0.47 | 20.54 ± 0.88 # | 21.77 ± 0.72 | 20.67 ± 0.84 | 19.26 ± 0.93 | 22.29 ± 0.70α | 20.16 ± 0.61 |
| 15 | 23.11 ± 0.44 | 20.34 ± 0.91 # | 21.67 ± 0.84 | 20.82 ± 0.91 | 19.96 ± 0.84 | 22.26 ± 0.69 * | 21.11 ± 0.58 |
| 16 | 23.21 ± 0.45 | 20.32 ± 0.85 # | 21.39 ± 0.94 | 20.41 ± 1.05 | 20.84 ± 0.46 | 22.39 ± 0.74 * | 21.09 ± 0.53 |
| 17 | 23.39 ± 0.43 | 19.60 ± 0.89 ## | 20.87 ± 0.92 | 19.85 ± 1.05 | 20.42 ± 0.50 | 21.02 ± 0.76 | 20.58 ± 0.38 |
| 18 | 23.71 ± 0.46 | 19.10 ± 0.88 ## | 20.99 ± 0.28 | 18.84 ± 1.06 | 19.78 ± 0.43 | 21.82 ± 0.89**α | 19.59 ± 0.34 |

Note:
compared with the blank group, # P < 0.05, ## P < 0.01;
compared with DSS group,
* p < 0.05,
**p < 0.01;
and compared with DSS + 005 group αp < 0.05 αα p < 0.01

3. Colon Length

Figure 3:
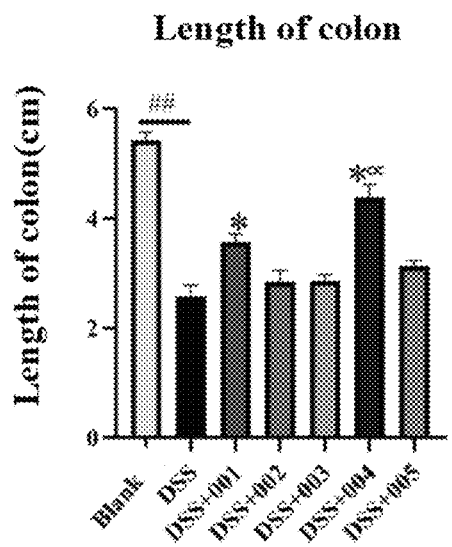
FIG. 3: histogram of colon length in experimental example 3.

The experimental results are shown in Table 3-5 and FIG. 3. Compared with the blank control group, the colon length of DSS group mice was significantly reduced. After drug intervention, compared with DSS group, Compounds 1-8, 1-13, 9-3, 1-11 and Filgotinib can reduce colon shortening in mice caused by DSS. Compounds 1-8 and 1-13 have significant effects, and the effect of Compounds 1-13 is significantly better than that of Filgotinib.

TABLE 3-5

Colon length of the present application

| Blank | DSS | DSS + 001 | DSS + 002 | DSS + 003 | DSS + 004 | DSS + 005 |
|---|---|---|---|---|---|---|
| 5.42 ± 0.15 | 2.58 ± 0.21## | 3.57 ± 0.15* | 2.84 ± 0.21 | 2.87 ± 0.11 | 4.39 ± 0.24*α | 3.13 ± 0.10 |

Note:
compared with the blank group, ##P < 0.01;
compared with DSS group *p < 0.05;
and compared with DSS + 005 group αp < 0.05

4. Spleen Index

Figure 4:
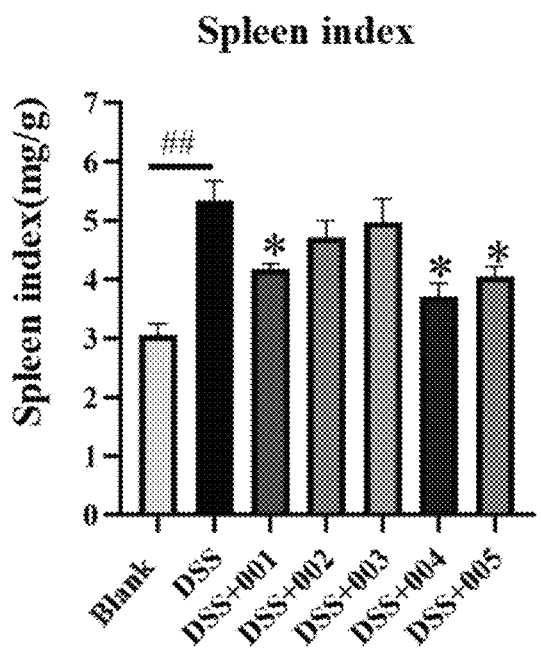
FIG. 4: histogram of spleen index in experimental example 3.

The experimental results are shown in Table 3-6 and FIG. 4. Compared with the blank control group, DSS can significantly increase the spleen index of mice (DSS group). After drug intervention, Compounds 1-8, 1-13, 9-3, 1-11 and Filgotinib could reduce the increase of spleen index in mice induced by DSS, and Compounds 1-8, 1-13 and Filgotinib had significant inhibitory effect.

TABLE 3-6

| Spleen index of the present invention | | | | | | |
|---|---|---|---|---|---|---|
| Blank | DSS | DSS + 001 | DSS + 002 | DSS + 003 | DSS + 004 | DSS + 005 |
| 3.06 ± 0.19 | 5.34 ± 0.34## | 4.17 ± 0.09* | 4.72 ± 0.28 | 4.98 ± 0.40 | 3.72 ± 0.22* | 4.04 ± 0.18* |

Note:
compared with the blank group, ##P < 0.01;
and compared with DSS group *p < 0.05

Conclusion: in the model of inflammatory bowel disease (IBD) in mice induced by DSS, the compounds of the present invention show good disease treatment effect, and have the same or even better drug effect in mice at half the dose of Filgotinib.

Experimental Example 4: In Vivo Pharmacodynamic Study of Compounds on Allergic Dermatitis (AD)

Experiment Purpose:

Atopic dermatitis (AD) is a chronic inflammatory skin disease, which is prone to recurrent attacks, its clinical manifestations include severe pruritus, pleomorphic lesions and dry skin disease like symptoms. Its pathogenesis is related to many factors such as heredity, immunity and infection. In recent years, the incidence rate of AD has been increasing year by year. The development of drugs for the treatment of AD will help to alleviate the skin symptoms and improve the quality of life of patients. The animal allergic dermatitis model induced by 1-chloro-2,4-dinitrobenzene (DNCB) is basically consistent with the clinical manifestations of AD patients. It is a classic model for preclinical evaluation of drug efficacy. The purpose of this experiment is to investigate the therapeutic effect of Compounds 1-8, 1-11, 9-3 and 1-13 on DNCB induced allergic dermatitis in mice, and to provide preclinical pharmacodynamic information for clinical research.

1. Preparation of Modeling Solution and Drugs for Intragastric Administration

Preparation method of solvent: vehicle solution is 30% PEG-400+70% (5% HP-β-CD), pH 4-5. Firstly, 35 g HP-β-CD was dissolved in 700 mL MilliQ pure water, 300 mL PEG-400 was added and mixed well, the pH was adjusted to 4-5, and stored at room temperature.

Preparation method of compounds: the compounds were weighed and added to 30% PEG-400+ 70% (5% HP-β-CD) solution (by volume), and ultrasonically processed. After the solution was fully mixed, it is load into glass bottles and stored in a 4° C. refrigerator.

2. Induction of Allergic Dermatitis and Administration

Seventy male Balb/c mice were weighed and randomly divided into 7 groups with 10 mice in each group. See Table 4-1 for detailed grouping and dose design information.

The animal adaptation period was 3 days. It was adapted to shaving on the back. After 2 days, it was sensitized with the modeling solution, coated with 20 μL 0.5% DNCB solution on the right ear of the mouse, applied with 200 μL 0.5% DNCB solution on the back, once a day for 3 days. The mice were stimulated from day 4, and applied with 10 μL 1% DNCB solution on the right ear of mice, 100 μL 1% DNCB solution on the back of mice, respectively, once every 3 days. At the same time, from day 4, the mice were given Compounds 1-8, 1-11, 9-3 and 1-13 by gavage, respectively, and the positive drug alonson was applied to the ear and back skin.

TABLE 4-1

| Grouping and dose design | | | | | | |
|---|---|---|---|---|---|---|
| Group | Names of drug to be tested | Number | Route of administration | Concentration | Dosage | Frequency of administration |
| Blank | Blank (solvent control group) | 10 | p.o. | N/A | N/A | qd, 28 days |
| DNCB | Blank (solvent control group) | 10 | p.o. | N/A | N/A | qd, 28 days |
| DNCB + Eloson | Eloson | 10 | Right ear/skin (external use) | N/A | 0.01 g/ 0.1 g | Once 3 days, 28 days |
| DNCB + A | Compounds 1-8 | 10 | p.o. | 3.0 mg/mL | 30 mg/kg | qd, 28 days |
| DNCB + B | Compounds 1-11 | 10 | p.o. | 3.0 mg/mL | 30 mg/kg | qd, 28 days |
| DNCB + C | Compounds 9-3 | 10 | p.o. | 3.0 mg/mL | 30 mg/kg | qd, 28 days |
| DNCB + D | Compounds 1-13 | 10 | p.o. | 3.0 mg/mL | 30 mg/kg | qd, 28 days |

Note:
P.O.: oral administration;
QD: once a day.

3. Disease Severity Test

Indicators of successful DNCB atopic dermatitis modeling: DNCB successfully induced BALB/c mice to produce typical atopic dermatitis like lesions such as erythema, erosion, bleeding, edema, epidermal exfoliation, epidermal thickening, etc. On days 3, 9, 15, 21, and 27, the severity of specific dermatitis was evaluated by evaluating four clinical inflammatory indicators of atopic dermatitis: Erythema/bleeding, scar/dryness, edema, and infiltration/erosion. Each evaluation index has four grades: 0, none; 1. slight; 2. moderate; 3. obvious; 4. very obvious. Sum the scores represents score of the skin. After the experiment, the thickness of the right ear of mice was measured, blood was taken from the eyes, and the serum was separated by centrifugation (3000 rpm, 15 min) to detect the concentration of LgE. The spleen was taken and the spleen index was calculated: spleen index=spleen weight (mg)/body weight (g).

4. Statistical Processing

The experimental data were expressed by means±standard error (Mean±SEM), and all data were statistically analyzed by one-way ANOVA, with P<0.05 as the statistical difference.

Experimental Results:

1. Skin Score

Figure 5:
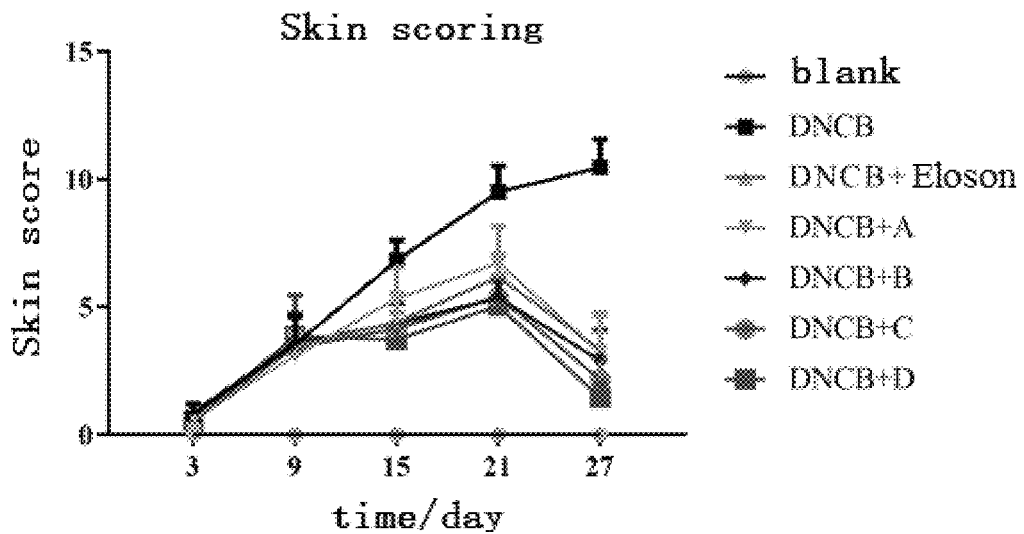
FIG. 5: curve diagram of skin score results in experimental example 4.

The skin score results showed that, as shown in Table 4-2 and FIG. 5, after DNCB induction, the skin score of DNCB group increased continuously. From day 9, the skin score was significantly higher than that of the blank control group, and continued until the end of the experiment. Compared with DNCB group, the skin score decreased gradually after drug intervention, and the Compounds 1-13 group significantly decreased at day 21 of administration, showing a better effect than the positive drug Alonson. At day 27 of administration, all treatment groups, including Compounds 1-8, 1-11, 9-3 and 1-13, and the alonson group, showed a significant reduction in skin scores.

TABLE 4-2 skin score of the present application

| Days | Blank | DNCB | DNCB + Eloson | DNCB + A | DNCB + B | DNCB + C | DNCB + D |
|---|---|---|---|---|---|---|---|
| 3 | 0.0 ± 0.0 | 0.8 ± 0.4 | 0.5 ± 0.5 | 0.6 ± 0.5 | 0.9 ± 0.3 | 0.7 ± 0.5 | 0.5 ± 0.5 |
| 9 | 0.0 ± 0.0 | 3.5 ± 1.1 ## | 3.5 ± 0.5 | 3.1 ± 0.8 | 3.6 ± 1.1 | 3.4 ± 0.7 | 3.9 ± 1.6 |
| 15 | 0.0 ± 0.0 | 6.8 ± 0.8 ## | 4.4 ± 1.1 | 5.3 ± 1.2 | 4.4 ± 0.8 | 4.2 ± 0.6 | 3.7 ± 0.6 |
| 21 | 0.0 ± 0.0 | 9.5 ± 1.0 ## | 6.2 ± 0.9 | 6.7 ± 1.4 | 5.4 ± 0.7 | 5.4 ± 0.9 | 5.0 ± 1.0 * |
| 27 | 0.0 ± 0.0 | 10.5 ± 1.1 ## | 3.3 ± 1.3 ** | 3.2 ± 1.5 ** | 2.9 ± 1.2 ** | 2.2 ± 0.9 ** | 1.5 ± 0.5 ** |

Note:

compared with the blank group, ## P < 0.01;

and compared with DNCB group, * p < 0.05, ** p < 0.01

2. Thickness of Right Ear

Figure 6:
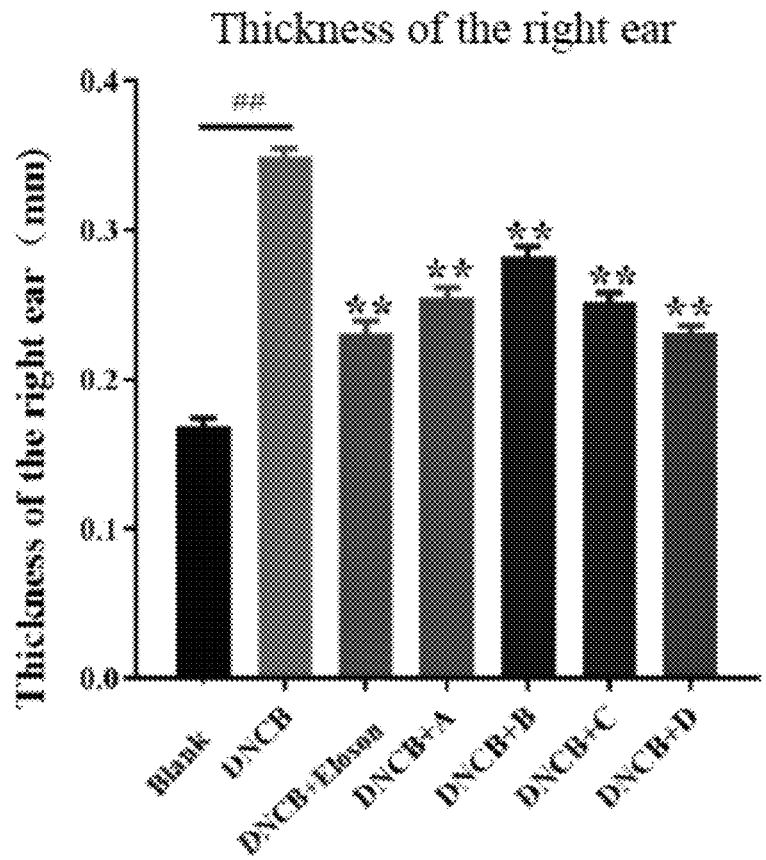
FIG. 6: right ear thickness histogram in experimental example 4.

The experimental results showed that (as shown in Table 4-3 and FIG. 6), the thickness of the right ear of mice after DNCB induction (DNCB group) significantly increased, and the thickness of the right ear of mice after drug intervention (including Compounds 1-8, 1-11, 9-3 and 1-13 and Eloson group) significantly decreased, indicating that Compounds 1-8, 1-11, 9-3 and 1-13 have a significant therapeutic effect on allergic dermatitis in mice induced by DNCB, which is equivalent to the effect of Eloson. Four compounds (compounds 1-8, 1-11, 9-3 and 1-13) had the strongest effect on the reduction of right ear thickness, but there was no significant difference between the groups.

TABLE 4-3 thickness of the right ear of the present application

| Blank | DNCB | DNCB + Eloson | DNCB + A | DNCB + B | DNCB + C | DNCB + D |
|---|---|---|---|---|---|---|
| 0.169 ± 0.005 | 0.349 ± 0.006 ## | 0.231 ± 0.008 ** | 0.254 ± 0.007 ** | 0.283 ± 0.006 ** | 0.252 ± 0.006 ** | 0.232 ± 0.004 ** |

Note:

compared with the blank group, ## P < 0.01;

and compared with DNCB group ** p < 0.01

3. Spleen Index

Figure 7:
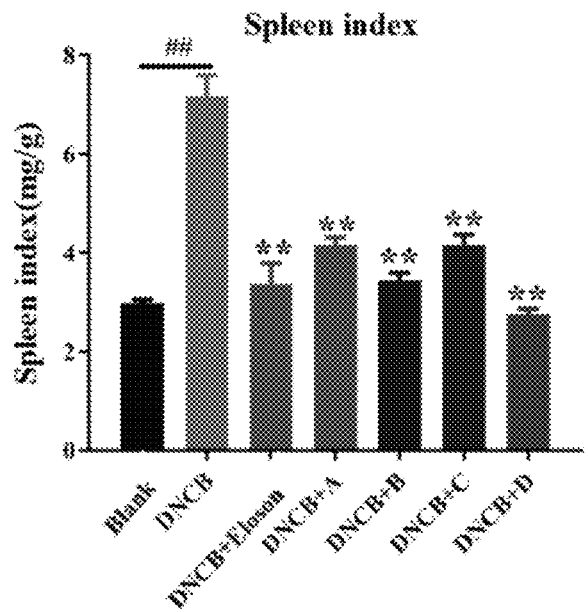
FIG. 7: histogram of spleen index in experimental example 4.

The experimental results showed that (as shown in Table 4-4 and FIG. 7), the spleen of mice after DNCB induction (DNCB group) was enlarged, which showed that the spleen index was significantly increased, and the spleen index of mice was significantly decreased through drug intervention (including Compounds 1-8, 1-11, 9-3 and 1-13 and elosone group), which showed that Compounds 1-8, 1-11, 9-3 and 1-13 have a significant therapeutic effect on allergic dermatitis in mice induced by DNCB, which is equivalent to the effect of elosone. The four compounds (Compounds 1-8, 1-11, 9-3 and 1-13) had the strongest effect on the reduction of spleen index, but there was no significant difference between the groups.

TABLE 4-4 spleen index of the present application

| Blank | DNCB | DNCB + Eloson | DNCB + A | DNCB + B | DNCB + C | DNCB + D |
|---|---|---|---|---|---|---|
| 2.98 ± 0.23 | 7.16 ± 1.37 ## | 3.37 ± 1.34 ** | 4.16 ± 0.48 ** | 3.45 ± 0.48 ** | 4.17 ± 0.65 ** | 2.76 ± 0.33 ** |

Figure 8:
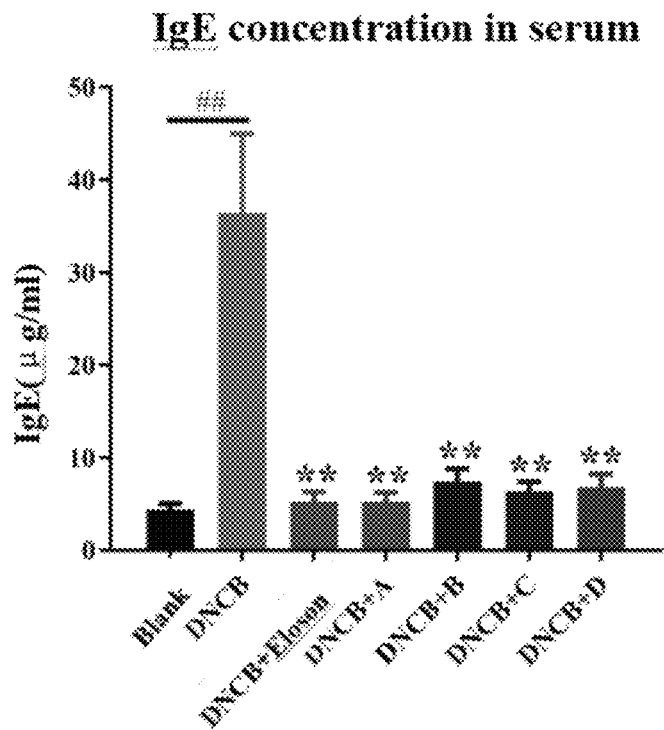
FIG. 8: histogram of serum IgE concentration in experimental example 4.

Note:
compared with the blank group, ## $P < 0.01$;
and compared with DNCB group ** $p < 0.01$ 4. IgE Concentration in Serum The experimental results showed that (as shown in Table 4-5 and FIG. 8), after DNCB induction (DNCB group), the concentration of IgE in serum of mice significantly increased, and the concentration of IgE in serum of mice significantly decreased through drug intervention (including Compounds 1-8, 1-11, 9-3 and 1-13 and Eloson group), indicating that Compounds 1-8, 1-11, 9-3 and 1-13 have significant therapeutic effect on allergic dermatitis in mice induced by DNCB.

TABLE 4-5

IgE concentration of the present application in serum

| Blank | DNCB | DNCB + Eloson | DNCB + A | DNCB + B | DNCB + C | DNCB + D |
|---|---|---|---|---|---|---|
| 4.39 ± 0.66 | 36.44 ± 8.53 ## | 5.26 ± 1.07 ** | 5.25 ± 0.99 ** | 7.46 ± 1.34 ** | 6.39 ± 1.04 ** | 6.79 ± 1.46 ** |

Figure 9:
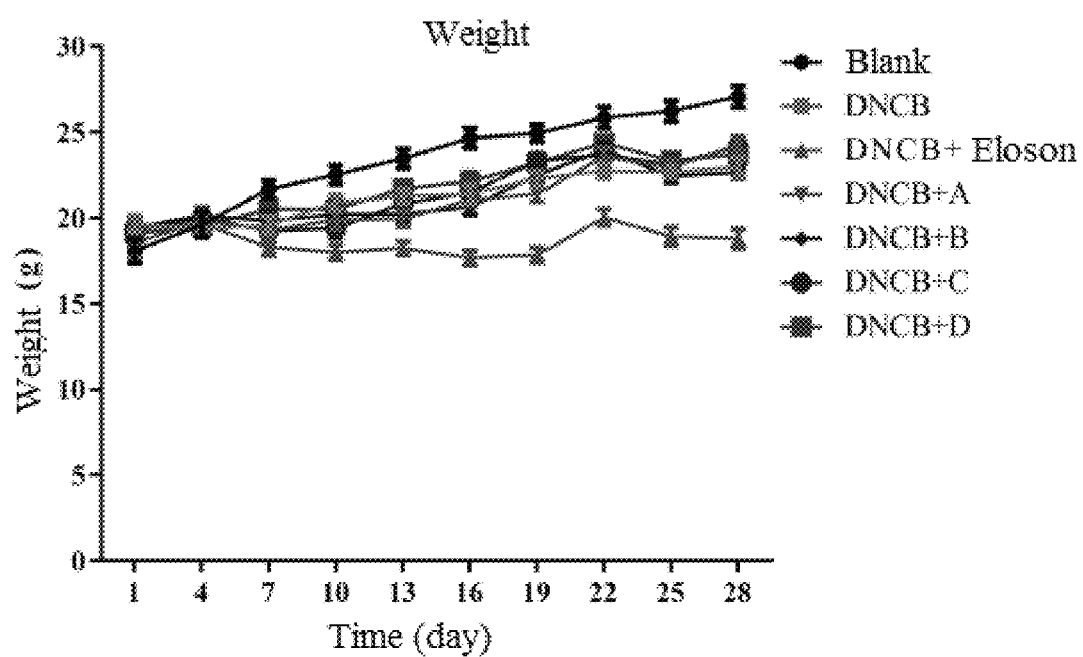
FIG. 9: curve diagram of weight change of mice in experimental example 4.

Note:
compared with the blank group, ## $P < 0.01$;
and compared with DNCB group ** $p < 0.01$ 5. Weight The experimental results showed that (as shown in Table 4-6 and FIG. 9), the weight of mice in the blank group and DNCB group increased slowly, and the weight of mice in DNCB group was slightly lower than that in the blank group, and there was no statistical difference between the groups. The weight of the four compounds (Compounds 1-8, 1-11, 9-3 and 1-13) group was the same as that of the DNCB group and higher than that of the alonson group, but there was no statistical difference between the groups, indicating that Compounds 1-8, 1-11, 9-3 and 1-13 had no significant effect on the weight of mice.

TABLE 4-6 weight of mice in the invention

| Days | Blank | DNCB | DNCB + Eloson | DNCB + A | DNCB + B | DNCB + C | DNCB + D |
|---|---|---|---|---|---|---|---|
| 1  | 18.08 ± 0.70 | 19.69 ± 0.44 | 19.42 ± 0.45 | 18.55 ± 0.83 | 19.45 ± 0.59 | 19.32 ± 0.46 | 19.11 ± 0.62 |
| 4  | 19.62 ± 0.76 | 19.36 ± 0.42 | 19.68 ± 0.45 | 19.84 ± 0.70 | 20.15 ± 0.46 | 20.02 ± 0.41 | 19.50 ± 0.50 |
| 7  | 21.68 ± 0.54 | 19.60 ± 0.49 | 18.29 ± 0.48 | 19.29 ± 0.84 | 19.84 ± 0.55 | 19.24 ± 0.47 | 20.52 ± 0.58 |
| 10 | 22.53 ± 0.55 | 20.91 ± 0.43 | 18.02 ± 0.42 | 19.89 ± 0.51 | 20.21 ± 0.62 | 19.41 ± 0.58 | 20.49 ± 0.48 |
| 13 | 23.48 ± 0.55 | 21.27 ± 0.41 | 18.24 ± 0.39 | 19.95 ± 0.45 | 20.24 ± 0.41 | 20.83 ± 0.42 | 21.72 ± 0.48 |
| 16 | 24.66 ± 0.58 | 21.41 ± 0.52 | 17.67 ± 0.41 | 21.05 ± 0.36 | 20.63 ± 0.43 | 21.49 ± 0.45 | 22.14 ± 0.53 |
| 19 | 24.95 ± 0.51 | 22.30 ± 0.43 | 17.85 ± 0.42 | 21.40 ± 0.44 | 22.50 ± 0.40 | 23.36 ± 0.38 | 23.24 ± 0.44 |
| 22 | 25.85 ± 0.61 | 22.76 ± 0.42 | 20.03 ± 0.47 | 23.60 ± 0.42 | 23.97 ± 0.42 | 23.67 ± 0.37 | 24.38 ± 0.42 |
| 25 | 26.24 ± 0.60 | 22.68 ± 0.33 | 18.92 ± 0.52 | 22.96 ± 0.46 | 22.45 ± 0.36 | 23.14 ± 0.42 | 23.35 ± 0.36 |
| 28 | 27.08 ± 0.62 | 22.97 ± 0.57 | 18.79 ± 0.55 | 24.28 ± 0.47 | 22.66 ± 0.34 | 24.15 ± 0.50 | 23.70 ± 0.33 |

Conclusion: in the mouse allergic dermatitis (AD) model induced by DNCB, Compounds 1-8, 1-11, 9-3 and 1-13 of the present invention can significantly reduce the skin score, right ear thickness, spleen index and serum IgE concentration of mice, and have no significant effect on body weight, showing a good disease treatment effect, which is equivalent to the effect of glucocorticoid alonson.

What is claimed is:

1. A method for the treatment of systemic lupus erythematosus, inflammatory bowel disease, atopic dermatitis, anti-acute rejection, anti-chronic rejection or induction of immune tolerance, comprising administering to a patient in need thereof a JAK inhibitors [1,2,4]triazolo [1,5-a]pyridine compound of formula (I), isomers, or pharmaceutically acceptable salts thereof:

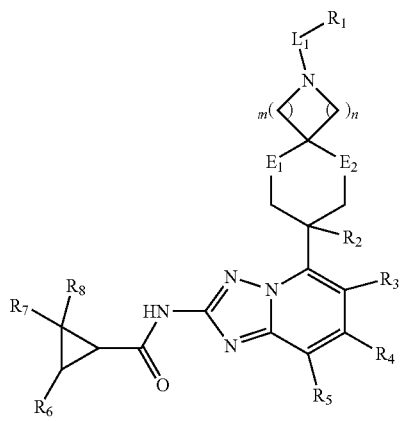

(I)

wherein, $E_1$ and $E_2$ are independently selected from single bond, —$CH_2$— or —$(CH_2)_2$—, respectively;

$L_1$ is selected from single bond, —$(CH_2)_g$—, —C(=O)— or —C(=O)—$(CH_2)_h$—;

m is 1 or 2;

n is 1 or 2;

g is 1, 2 or 3;

h is 1, 2 or 3;

$R_1$ is selected from H, CN, $C_{1-6}$ alkyl or 3- to 6-membered cycloalkyl, wherein the $C_{1-6}$ alkyl and 3- to 6-membered cycloalkyl are optionally substituted by 1, 2 or 3 $R_a$;

$R_2$ is selected from H, F, Cl, Br, I or $C_{1-3}$ alkyl, wherein the $C_{1-3}$ alkyl is optionally substituted by 1, 2 or 3 $R_b$;

$R_3$, $R_4$ and $R_5$ are independently selected from H, F, Cl, Br, I or $C_{1-3}$ alkyl, respectively, wherein the $C_{1-3}$ alkyl is optionally substituted by 1, 2 or 3 $R_c$;

$R_6$, $R_7$ and $R_8$ are independently selected from H, F, Cl, Br, I or $C_{1-3}$ alkyl, respectively, wherein the $C_{1-3}$ alkyl is optionally substituted by 1, 2 or 3 $R_d$;

Each $R_a$ is independently selected from H, F, Cl, Br, I, CN or $C_{1-3}$ alkyl, respectively, wherein the $C_{1-3}$ alkyl is optionally substituted by 1, 2 or 3 R;

Each $R_b$ is independently selected from F, Cl, Br or I, respectively;

Each $R_c$ is independently selected from F, Cl, Br or I, respectively;

Each $R_d$ is independently selected from F, Cl, Br or I, respectively; and

Each R is independently selected from F, Cl, Br or I, respectively.

2. The method according to claim 1, wherein each $R_a$ in the compounds of formula (I) is independently selected from H, F, Cl, Br, I or CN, respectively.

3. The method according to claim 1, wherein $R_1$ in the compounds of formula (I) is selected from H, CN, $C_{1-3}$ alkyl or 3- to 5-membered cycloalkyl, wherein the $C_{1-3}$ alkyl and 3- to 5-membered cycloalkyl are optionally replaced by 1, 2 or 3 $R_a$.

4. The method according to claim 1, wherein $R_2$ in the compounds of formula (I) is selected from H, F, Cl, Br or I.

5. The method according to claim 1, wherein $R_3$, $R_4$ and $R_5$ in the compounds of formula (I) are independently selected from H, F, Cl, Br or I, respectively.

6. The method according to claim 1, wherein $R_6$, $R_7$ and $R_8$ in the compounds of formula (I) are independently selected from H, F, Cl, Br or I, respectively.

7. The method according to claim 1, wherein $L_1$ in the compounds of formula (I) is selected from single bond, —$CH_2$—, —$(CH_2)_2$—, —C(=O)— or —C(=O)—$(CH_2)$—.

8. The method according to claim 1, wherein the structural unit

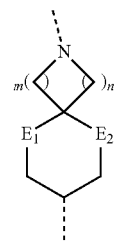

in the compounds of formula (I) is selected from
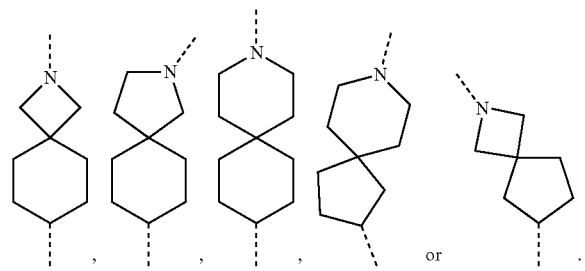
9. The according to claim 1, wherein the structural unit
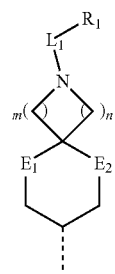
in the compounds of formula (I) is selected from
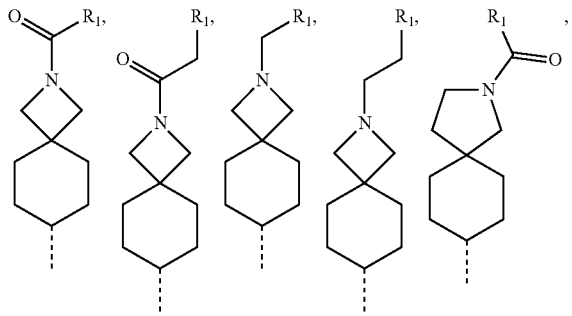
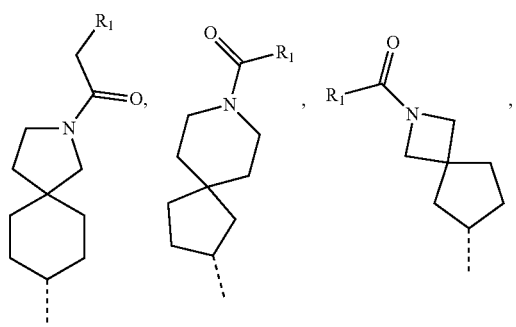
-continued
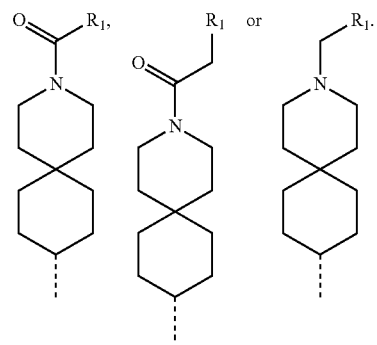
10. The method according to claim 1, wherein the structural unit
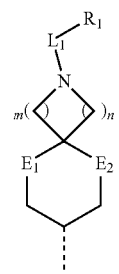
in the compounds of formula (I) is selected from
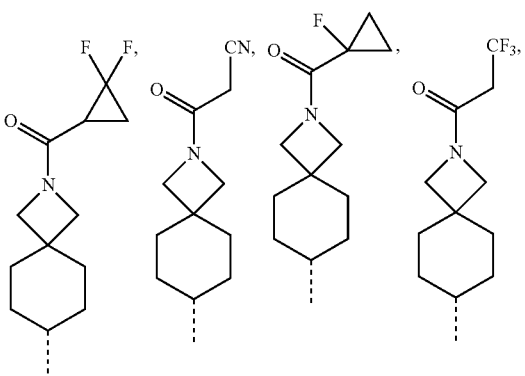
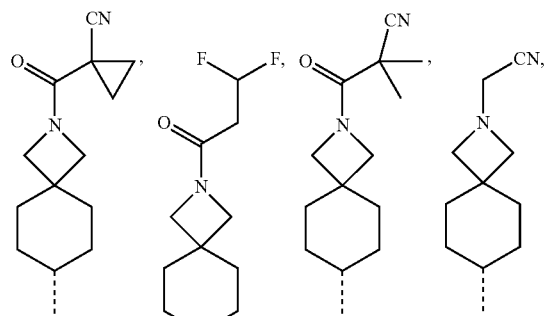

-continued
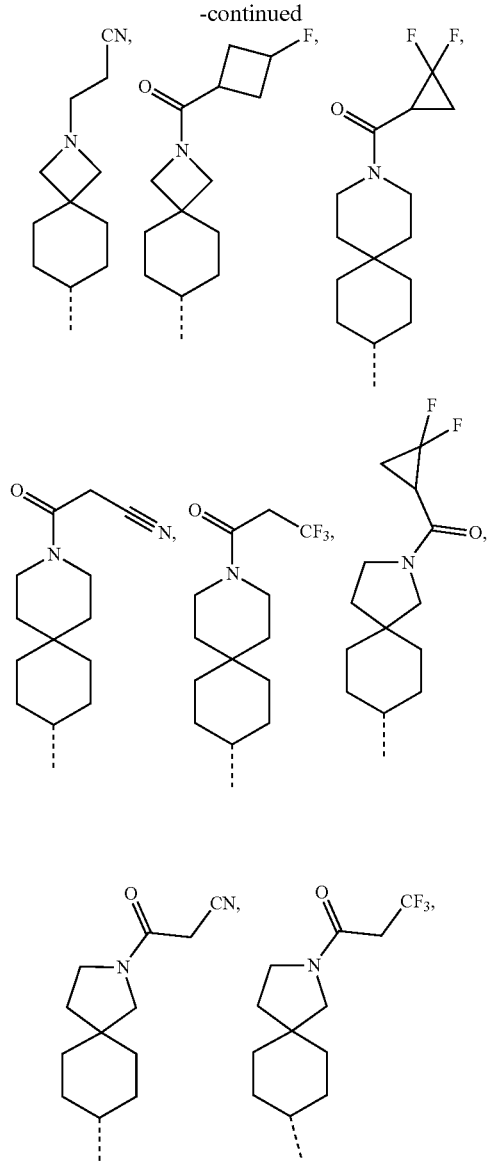
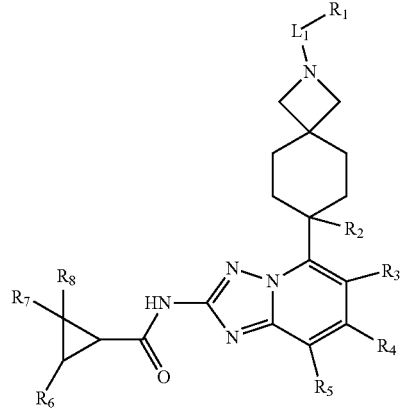
(I-1)
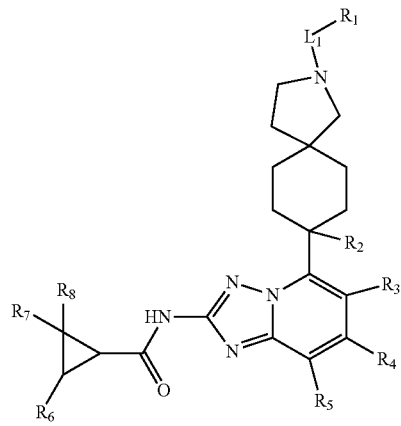
(I-2)
11. The method according to claim 1, wherein the compounds of formula (I), their isomers or their pharmaceutically acceptable salts are selected from
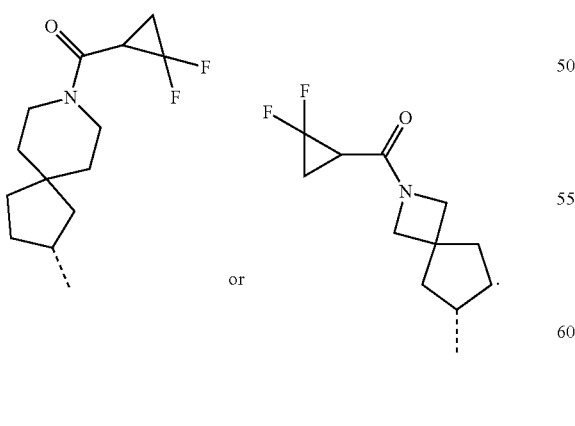
(I-3)

85
-continued
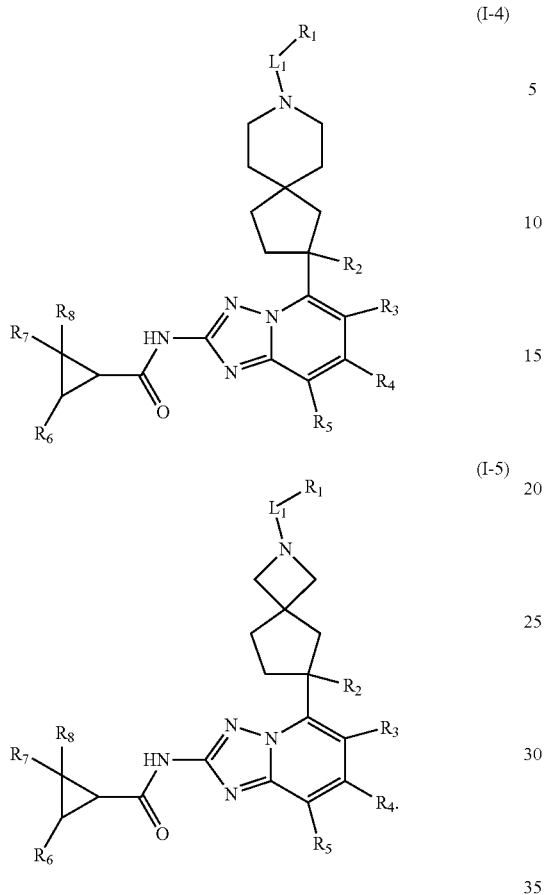
(I-4)
(I-5)
12. The method according to claim 11, wherein the compounds of formula (I), their isomers or their pharmaceutically acceptable salts are selected from
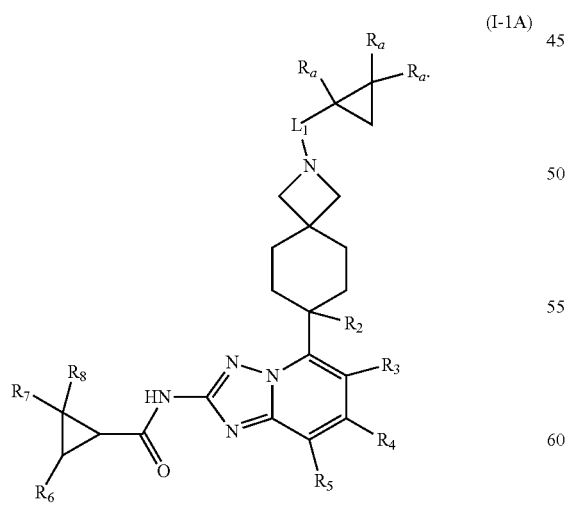
(I-1A)
13. The method according to claim 1, wherein the compounds of formula (I), their isomers or their pharmaceutically acceptable salts are selected from:
86
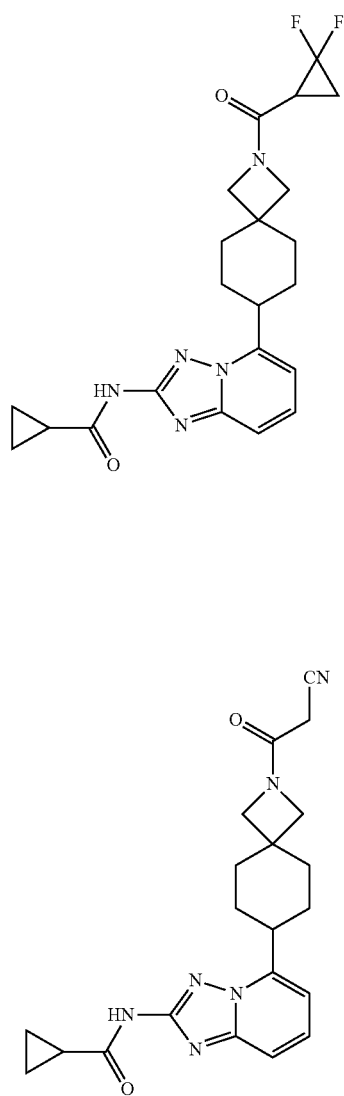
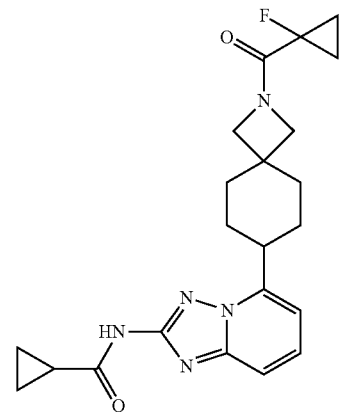

87
-continued
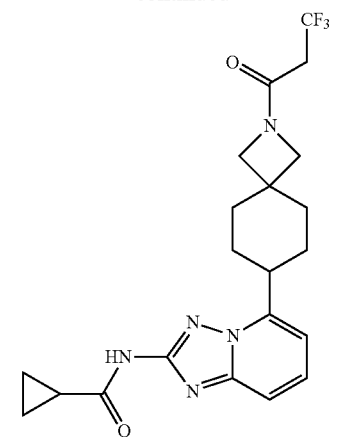
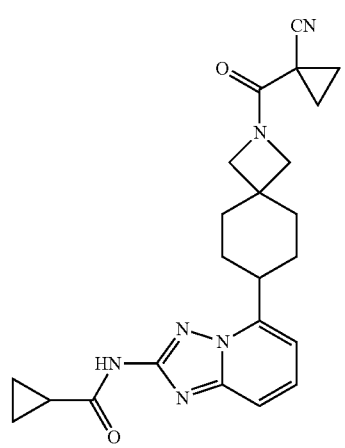
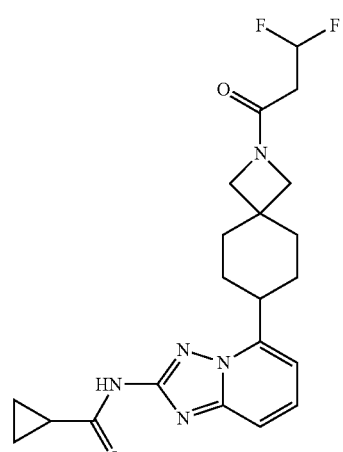
88
-continued
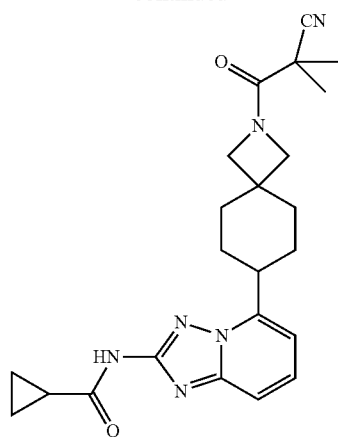
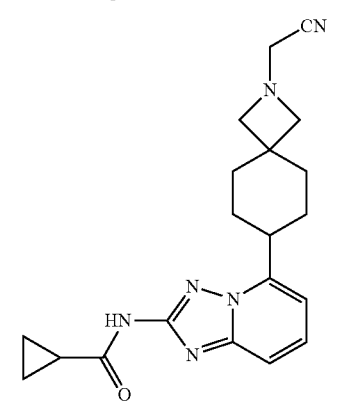
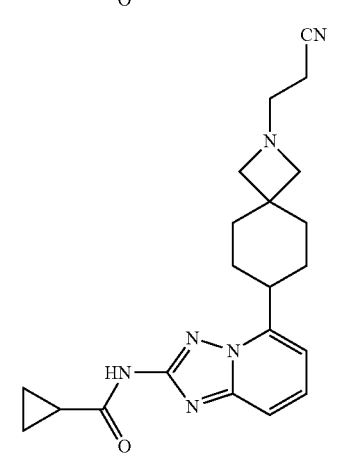
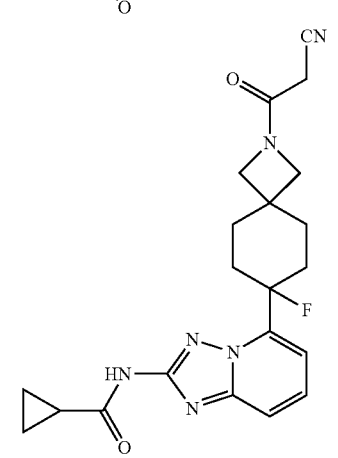

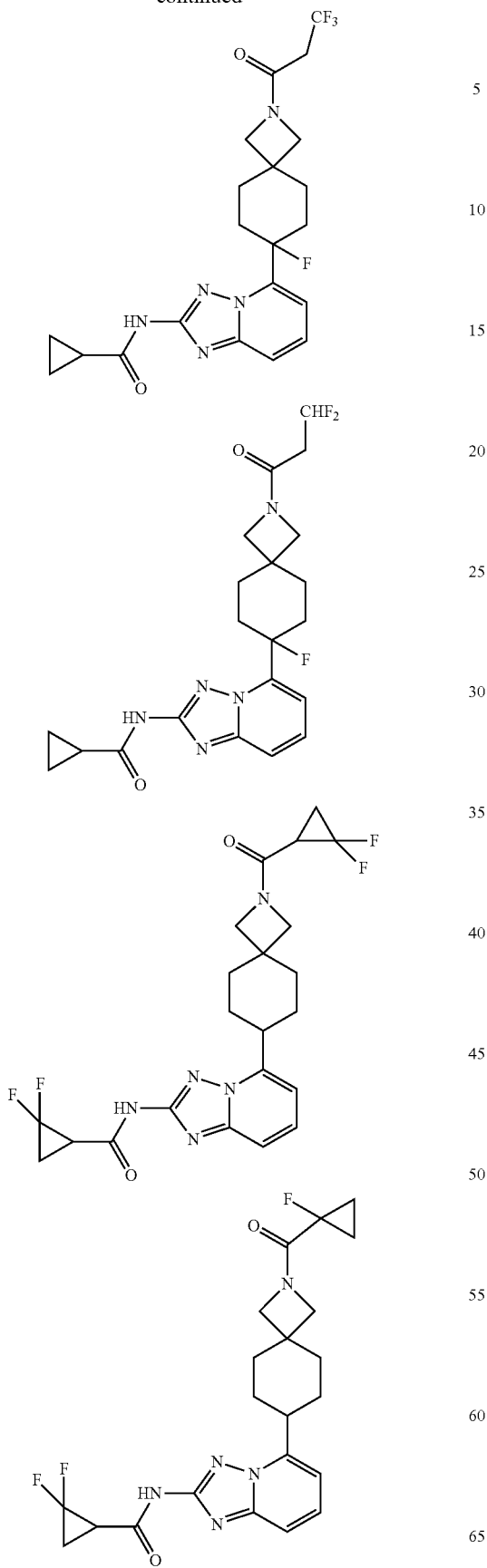
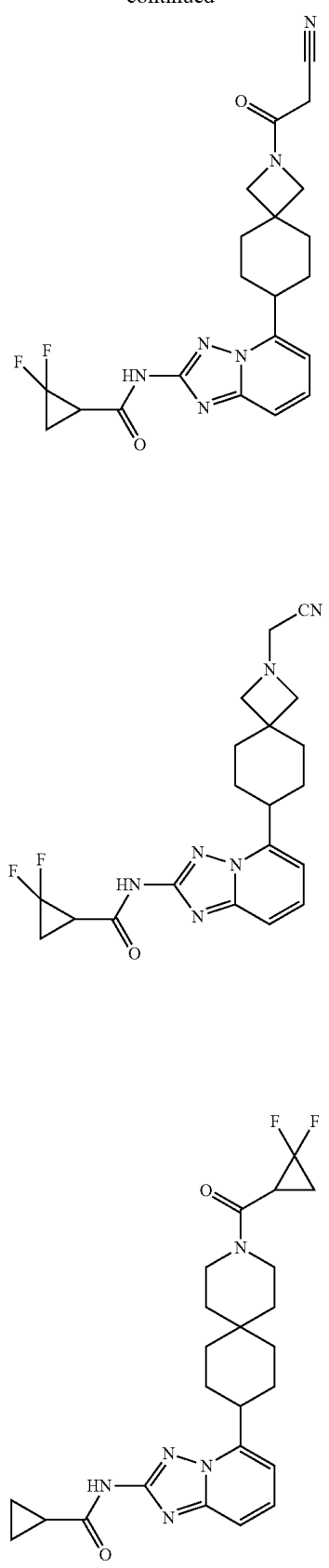

-continued
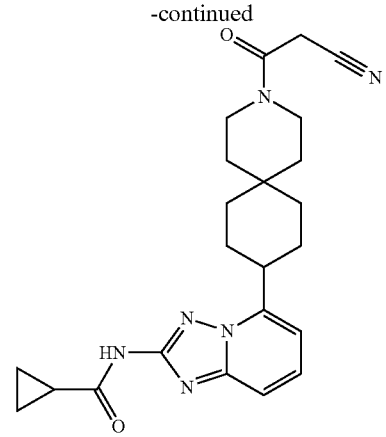
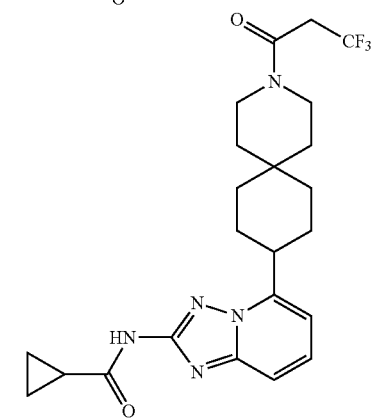
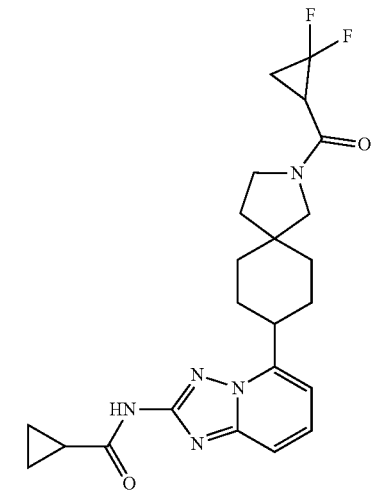
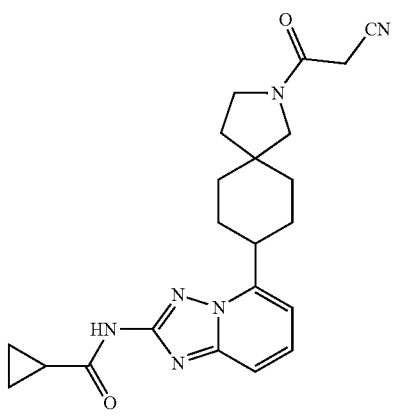
-continued
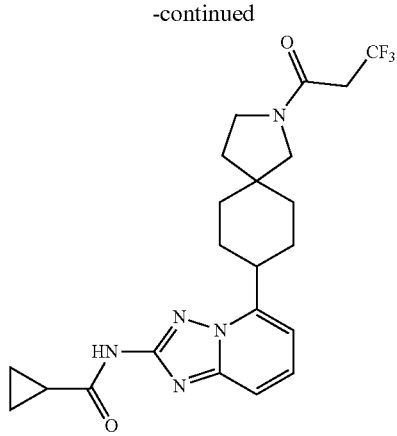
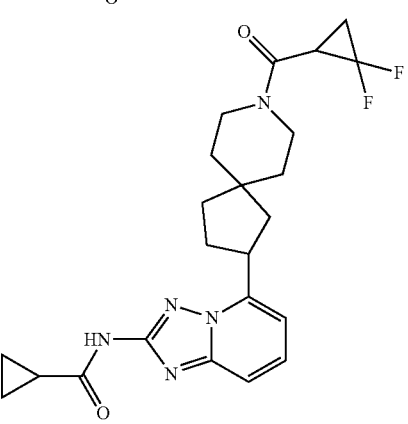
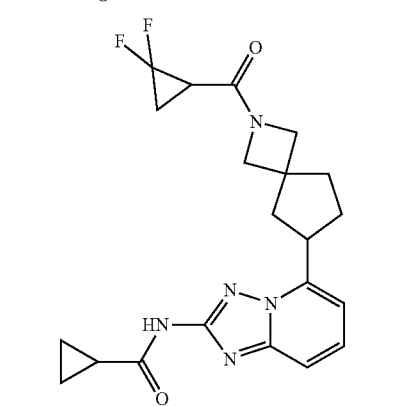
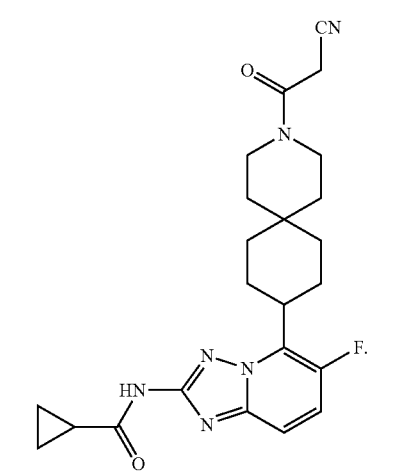 [SMILES: N#CCC(=O)N1CCC2(CCC(c3c(F)ccc4nc(NC(=O)C5CC5)nn34)CC2)CC1]

14. The method according to claim 13, wherein the compounds of formula (I), their isomers or their pharmaceutically acceptable salts are selected from:
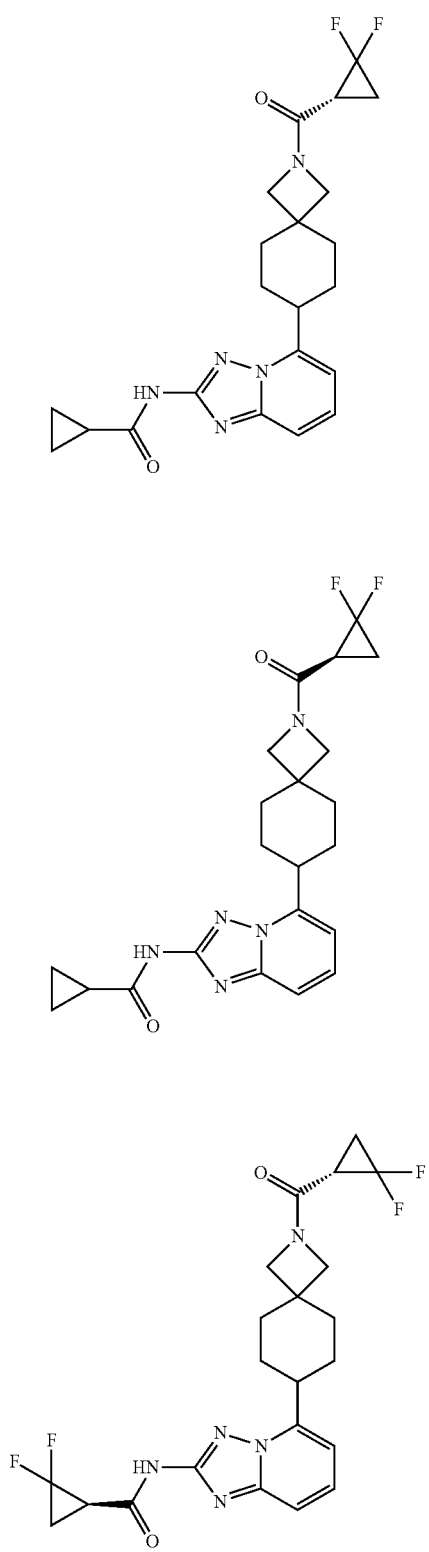
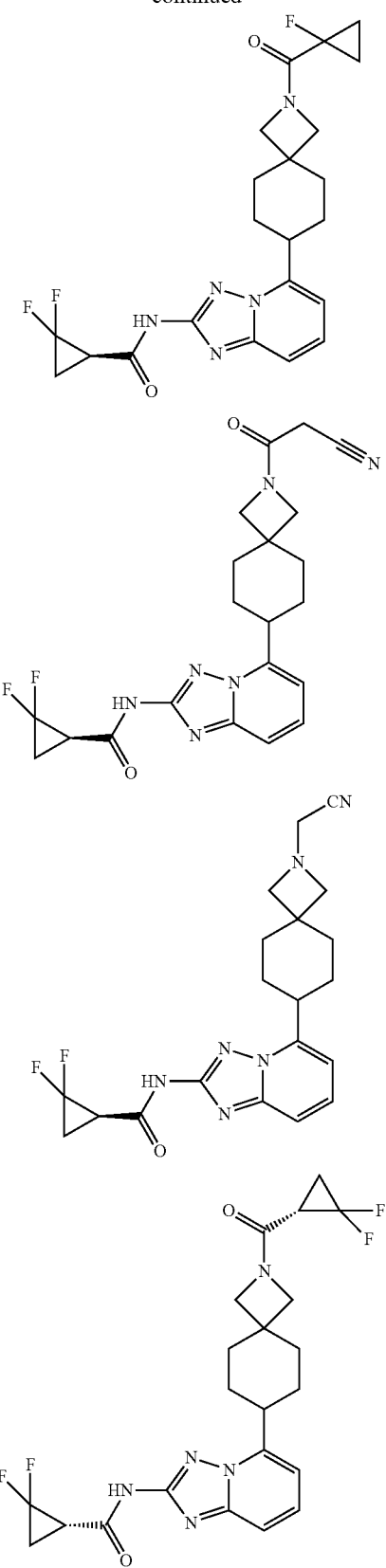

95
-continued
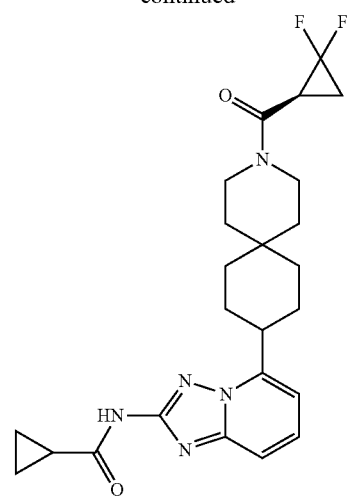
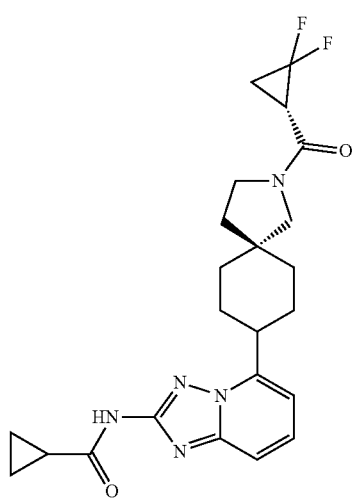
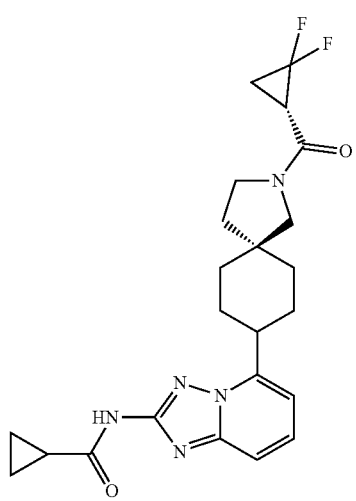
96
-continued
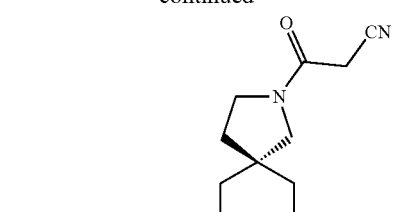
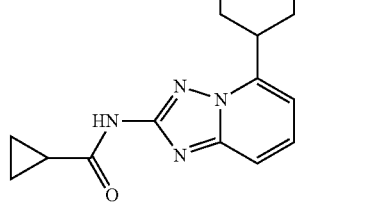
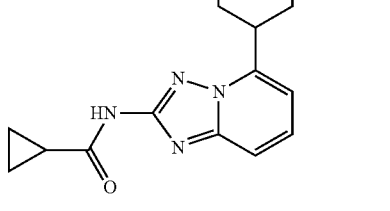
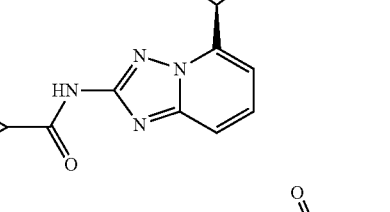

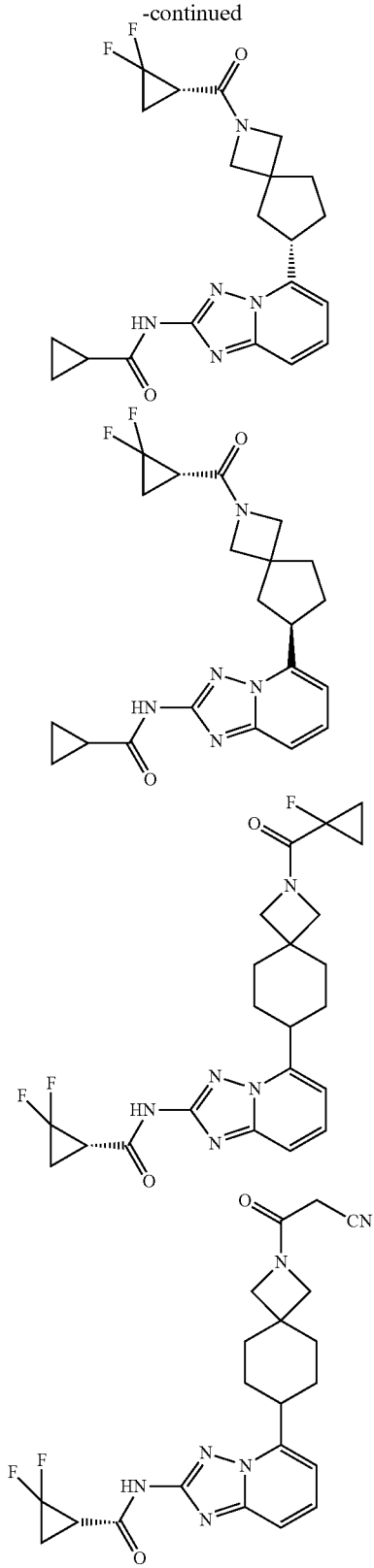
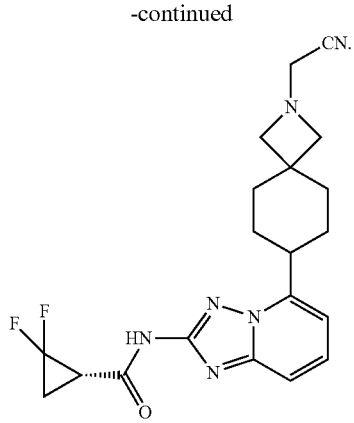
15. The method according to claim 3, wherein R₁ in the compounds of formula (I) is selected from H, CN, CH₃,
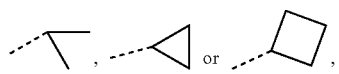
wherein the CH₃,
are optionally replaced by 1, 2 or 3 Rₐ.
16. The method according to claim 15, wherein R₁ in the compounds of formula (I) is selected from H, CN, CF₃, CHF₂,
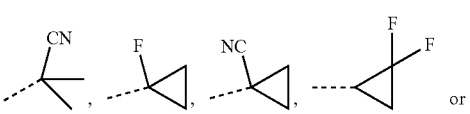
* * * * *